US008435976B2

(12) United States Patent
Wang et al.

(10) Patent No.: US 8,435,976 B2
(45) Date of Patent: May 7, 2013

(54) 4-SUBSTITUTED PYRIDIN-3-YL-CARBOXAMIDE COMPOUNDS AND METHODS OF USE

(75) Inventors: Xiaojing Wang, Foster City, CA (US); Allen J. Ebens, Jr., San Carlos, CA (US)

(73) Assignee: F. Hoffmann-La Roche, Basel (CH)

( * ) Notice: Subject to any disclaimer, the term of this patent is extended or adjusted under 35 U.S.C. 154(b) by 269 days.

(21) Appl. No.: 12/877,202

(22) Filed: Sep. 8, 2010

(65) Prior Publication Data

US 2011/0059961 A1     Mar. 10, 2011

Related U.S. Application Data

(60) Provisional application No. 61/240,474, filed on Sep. 8, 2009.

(51) Int. Cl.
| A01N 43/00 | (2006.01) |
| A01N 43/40 | (2006.01) |
| A61K 31/33 | (2006.01) |
| A61K 31/497 | (2006.01) |
| A61K 31/445 | (2006.01) |
| A61K 31/44 | (2006.01) |
| C07D 403/00 | (2006.01) |
| C07D 405/00 | (2006.01) |
| C07D 409/00 | (2006.01) |
| C07D 417/00 | (2006.01) |

(52) U.S. Cl.
USPC ........ 514/183; 514/253.1; 514/318; 514/342; 544/364; 546/270.7

(58) Field of Classification Search ............. 514/183, 514/253.1, 318, 342; 544/364; 546/270.7
See application file for complete search history.

(56) References Cited

U.S. PATENT DOCUMENTS

| 5,990,109 | A | 11/1999 | Chen et al. |
| 6,605,624 | B1 | 8/2003 | Lee et al. |
| 7,511,062 | B2 | 3/2009 | Kuang et al. |
| 7,781,433 | B2 * | 8/2010 | Chuckowree et al. ..... 514/234.5 |
| 2004/0029920 | A1 | 2/2004 | Kuduk et al. |
| 2006/0252807 | A1 | 11/2006 | Severance et al. |
| 2007/0037807 | A1 | 2/2007 | Oi et al. |
| 2009/0203715 | A1 | 8/2009 | Bothe et al. |
| 2009/0274655 | A1 | 11/2009 | Grimes et al. |
| 2009/0286766 | A1 | 11/2009 | Sugasawa et al. |
| 2010/0055090 | A1 | 3/2010 | Shipps et al. |
| 2010/0130465 | A1 | 5/2010 | Shipps et al. |
| 2010/0136136 | A1 | 6/2010 | Galan et al. |
| 2010/0249030 | A1 | 9/2010 | Basso-Porcaro et al. |
| 2010/0249088 | A1 | 9/2010 | Sugasawa et al. |
| 2010/0331313 | A1 | 12/2010 | Reddy et al. |
| 2011/0129440 | A1 | 6/2011 | Tadikonda et al. |

FOREIGN PATENT DOCUMENTS

| WO | 2008/054702 A1 | 5/2008 |
| WO | 2008/106692 A1 | 9/2008 |
| WO | 2009/058730 A1 | 5/2009 |
| WO | 2009/109576 A1 | 9/2009 |

OTHER PUBLICATIONS

Morgan, S. What are the differences between mutilple lymphoma and Myeloid Leukemia, 2011, pp. 1-7.*
International Search Report of WO 2008/054749, 2008.
International Search Report of EP 2009005, 2008.
International Search Report of WO 2005/116009, 2005.
Norris et al., "Synthesis of imidazo[1,5-a]quinoxalin-4(5H)—one template via a novel intramolecular cyclization process" Tetrahedron Letters 42:4297-4299 (2001).

* cited by examiner

*Primary Examiner* — Samira Jean-Louis
(74) *Attorney, Agent, or Firm* — Alex Andrus; Genentech, Inc.

(57) ABSTRACT

The invention relates to compounds of formula (I) which are useful as kinase inhibitors, more specifically useful as PIM kinase inhibitors, thus useful as cancer therapeutics. The invention also relates to compositions, more specifically pharmaceutical compositions comprising these compounds and methods of using the same, either alone or in combination, to treat various forms of cancer and hyperproliferative disorders, as well as methods of using the compounds for in vitro, in situ, and in vivo diagnosis or treatment of mammalian cells, or associated pathological conditions.

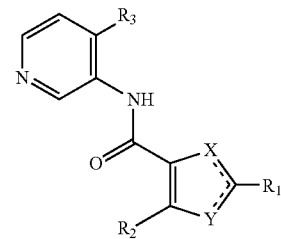

formula (I)

4 Claims, 8 Drawing Sheets

4-SUBSTITUTED PYRIDIN-3-YL-CARBOXAMIDE COMPOUNDS AND METHODS OF USE

CROSS REFERENCE TO RELATED APPLICATIONS

This non-provisional application filed under 37 CFR §1.53 (b), claims the benefit under 35 USC §119(e) of U.S. Provisional Application Ser. No. 61/240,474 filed on 8 Sep. 2009, which is incorporated by reference in entirety

FIELD OF THE INVENTION

The invention relates to 4-substituted N-(pyridin-3-yl) carboxamides of formula (I) which are useful as kinase inhibitors, more specifically useful as Pim kinase (Pim-1, Pim-2, and/or Pim-3) inhibitors, thus useful as cancer therapeutics. The invention also relates to compositions, more specifically pharmaceutical compositions comprising these compounds and methods of using the same, either alone or in combination, to treat various forms of cancer and hyperproliferative disorders, as well as methods of using the compounds for in vitro, in situ, and in vivo diagnosis or treatment of mammalian cells, or associated pathological conditions.

BACKGROUND OF THE INVENTION

Pim kinases are family of three highly-related serine and threonine protein kinases encoded by the genes Pim-1, Pim-2, and Pim-3. The gene names are derived from seminal experiments by Anton Berns et al., seeking oncogenes causing lymphoma, and the names are derived from the phrase Proviral Insertion, Moloney, as they were discovered as frequent integration sites for murine moloney virus wherein the insertions lead to overexpression of Pim's and either de novo T-cell lymphomas, or dramatic acceleration of tumorigenesis in a transgenic Myc-driven lymphoma model, revealing not only a strong synergy with the oncogene c-Myc, but also a functional redundancy among Pim kinase family members and suggesting that inhibition of the Pim's may have therapeutic benefit. (Cuypers et al (1984) Cell vol. 37 (1) pp. 141-50; Selten et al (1985) EMBO J vol. 4 (7) pp. 1793-8; van der Lugt et al (1995) EMBO J vol. 14 (11) pp. 2536-44; Mikkers et al (2002) Nature Genetics vol. 32 (1) pp. 153-9; van Lohuizen et al (1991) Cell vol. 65 (5) pp. 737-52).

Mouse genetics suggest that antagonizing Pim kinases should have an acceptable safety profile; a Pim 1–/–; Pim-2–/–, Pim-3–/– mouse knockout is viable although slightly smaller than wild type littermates (Mikkers et al (2004) Mol Cell Biol vol. 24 (13) pp. 6104-154). The three genes give rise to six protein isoforms that are little more than a protein kinase domain. In particular, they are without recognizable regulatory domains. All six isoforms are constitutively active protein kinases that do not require post-translational modification for activity, thus Pim kinases are regulated primarily at the transcriptional level (Qian et al (2005) J Biol Chem vol. 280 (7) pp. 6130-7). Pim kinase expression is highly inducible by cytokines and growth factors receptors and Pim's are direct transcriptional targets of the Stat proteins, including Stat3 and Stat5. Pim-1, for example, is required for the gp130-mediated Stat3 proliferation signal (Aksoy et al (2007) Stem Cells vol. 25 (12) pp. 2996-3004; Hirano et al (2000) Oncogene vol. 19 (21) pp. 2548-56; Shirogane et al (1999) Immunity vol. 11 (6) pp. 709-19).

Pim kinases have been shown to function in cellular proliferation and survival pathways parallel to the PI3K/Akt/mTOR signaling axis (Hammerman et al (2005) Blood vol. 105 (11) pp. 4477-83). Indeed, several of the phosphorylation targets of the PI3k axis including Bad and eIF4E-BP1 are cell growth and apoptosis regulators and are also phosphorylation targets of the Pim kinases (Fox et al (2003) Genes Dev vol. 17 (15) pp. 1841-54; Macdonald et al (2006) Cell Biol vol. 7 pp. 1). Pim-1 kinase promotes inactivation of the pro-apoptotic Bad protein by phosphorylating it on the Ser112 gatekeeper site, suggesting a role for the Pim kinase in cell survival since phosphorylation of Bad increases Bcl-2 activity and therefore promotes cell survival (Aho et al BMC FEBS Letters (2004) vol. 571 (1-3) pp. 43-9; Tamburini et al (2009) Blood vol. 114 (8) pp. 1618-27). Likewise, phosphorylation of eIF4E-BP1 by mTOR or Pim kinases causes depression of eIF4E, promoting mRNA translation and cellular growth. In addition, Pim-1 has been recognized to promote cell cycle progression through phosphorylation of CDC25A, p21, and Cdc25C (Mochizuki et al (1999) J Biol Chem vol. 274 (26) pp. 18659-66; Bachmann et al (2006) Int J Biochem Cell Biol vol. 38 (3) pp. 430-43; Wang et al (2002) Biochim Biophys Acta vol. 1593 (1) pp. 45-55).

Pim kinases have been implicated in multiple human oncology indications. Pim kinases show strong synergy with transgenic mouse models with c-Myc-driven and Akt-driven tumors (Verbeek et al (1991) Mol Cell Biol vol. 11 (2) pp. 1176-9; Allen et al (1997) Oncogene vol. 15 (10) pp. 1133-41; Hammerman et al (2005) Blood vol. 105 (11) pp. 4477-83). Pim Kinases are required for the transforming activity of oncogenes identified in acute myeloid leukemia (AML) including Flt3-ITD, BCR-ab1, and Tel-Jak2. Expression of these oncogenes in BaF3 cells results in strong upregulation of Pim-1 and Pim-2 expression, resulting in IL-3 independent growth, and subsequent pim inhibition results in apoptosis and cell growth arrest (Adam et al (2006) Cancer Research vol. 66 (7) pp. 3828-35). Pim overexpression and dysregulation has also been noted as a frequent event in many hematopoetic cancers, including leukemias and lymphoma (Amson et al (1989) Proc Natl Acad Sci USA vol. 86 (22) pp. 8857-61); Cohen et al (2004) Leuk Lymphoma vol. 45 (5) pp. 951-5; Hüttmann et al (2006) Leukemia vol. 20 (10) pp. 1774-82), as well as multiple myeloma (Claudio et al (2002) Blood vol. 100 (6) pp. 2175-86).

In prostate cancer, Pim-1 has been shown to be overexpressed and correlated to disease progression (Cibull et al (2006) J Clin Pathol vol. 59 (3) pp. 285-8; Dhanasekaran et al (2001) Nature vol. 412 (6849) pp. 822-6). Pim 1 expression increases with disease progression in mouse models of prostate cancer progression (Kim et al (2002) Proc Natl Acad Sci USA vol. 99 (5) pp. 2884-9). Pim-1 has been reported to be the most highly overexpressed mRNA in the subset of human prostate tumor samples which have a c-Myc-driven gene signature (Ellwood-Yen et al (2003) Cancer Cell vol. 4 (3) pp. 223-38). Pim-3 has been also been shown to be overexpressed and to have a functional role in pancreatic cancer and Hepatocellular Carcinoma (Li et al. (2006) Cancer Research vol. 66 (13) pp. 6741-7; Fujii et al (2005) Int J Cancer vol. 114 (2) pp. 209-18).

Therefore, multiple lines of evidence exist to support the possible therapeutic value of Pim kinase inhibition in oncology. Beyond these applications, Pim kinases could play an important role in normal immune system function and Pim inhibition could be therapeutic for a number of different immunologic pathologies including inflammation, autoimmune conditions, allergy, and immune suppression for organ transplantation (Aho et al (2005) Immunology vol. 116 (1) pp. 82-8).

SUMMARY OF THE INVENTION

The invention relates generally to 4-substituted N-(pyridin-3-yl) carboxamides of formula (I) (and/or solvates, hydrates and/or salts thereof) with Pim kinase (Pim-1, Pim-2, and/or Pim-3) inhibitory activity. The compounds of the present invention are useful as inhibitors of Pim kinase. Accordingly, the compounds of the invention and compositions thereof are useful in the treatment of hyperproliferative disorders such as cancer.

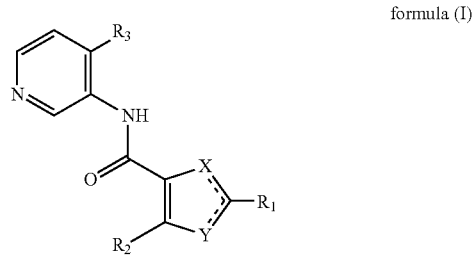

formula (I)

wherein:

X is N, S, or O;

Y is NH, N, S, or O; provided that X and Y are not S or O at the same time;

$R_1$ is H, halo, hydroxyl, nitro, cyano, alkyl, alkenyl, $OR_4$, $SR_4$, $SO_2R_4$, $SO_3R_4$, —$N(R_4)_2$, —$C(O)N(R_4)_2$, —$NR_4C(O)R_4$, —$C(S)N(R_4)_2$, —$NR_4C(S)R_4$, —$NR_4C(O)N(R_4)_2$, —$NR_4C(S)N(R_4)_2$, —$OC(O)N(R_4)_2$, —$SO_2N(R_4)_2$, —$N(R_4)SO_2R_4$, —$N(R_4)SO_2N(R_4)_2$, $NR_4C(=NH)R_4$, —$C(O)OR_4$, —$OC(O)OR_4$, cycloalkyl, heterocycloalkyl, aryl, or heteroaryl, wherein said alkyl, alkenyl, cycloalkyl, heterocycloalkyl, aryl, or heteroaryl is optionally substituted with one to three $R^4$ groups;

$R_2$ is hydrogen, halo, alkyl, cycloalkyl, —CN, —$NO_2$, and —$NHR_5$;

$R_3$ is —$N(R_4)_2$, $OR_4$, halo, cycloalkyl, heterocycloalkyl, aryl, or heteroaryl, wherein said cycloalkyl, heterocycloalkyl, aryl, or heteroaryl is optionally substituted with one to three $R^7$ groups; provided that when X is N and Y is S, then $R_3$ is not N-piperazinyl;

each $R_4$ is independently H, alkyl, cycloalkyl, heterocycloalkyl, aryl, heteroaryl, halo, CN, $CF_3$, —$OCF_3$, —$NO_2$, oxo, —$C(=Z)R_7$, —$C(=Z)OR_7$, —$C(=Z)N(R_7)_2$, —$N(R_7)_2$, —$OR_7$, —$SR_7$, —$NR_7C(=Z)R_7$, —$NR_7C(=Z)OR_7$, —$NR_7C(=Z)N(R_7)_2$, —$NR_7SO_2R_7$, —$OC(=Z)R_7$, —$OC(=Z)N(R_7)_2$, —$S(O)R_B$, —$S(O)_2R_7$, or —$S(O)_2NR_7$, wherein said alkyl, cycloalkyl, heterocycloalkyl, aryl, or heteroaryl is optionally substituted with one to three $R_7$ groups; and wherein two $R_4$s attached to the same N atom are optionally taken together with the attached N atom to form a 5-7 membered ring having additional 0-2 heteroatoms selected from O, S, and N, said ring being optionally substituted with one to three $R_7$ groups;

$R_5$ is H, —$COR_6$, alkyl, cycloalkyl, heterocyclyl, aryl, or heteroaryl, wherein said alkyl, cycloalkyl, heterocyclyl, aryl, or heteroaryl is optionally substituted with one to three $R_7$ groups;

$R_6$ is alkyl, $OR_4$, or —$N(R_4)_2$;

each $R_7$ is independently H, alkyl, cycloalkyl, heterocyclyl, aryl, heteroaryl, halo, CN, $CF_3$, —$OCF_3$, —$NO_2$, oxo, —$C(=Z)R_8$, —$C(=Z)OR_8$, —$C(=Z)N(R_8)_2$, —$N(R_8)_2$, —$OR_8$, —$SR_8$, —$NR_8C(=Z)R_8$, —$NR_8C(=Z)OR_8$, —$NR_8C(=Z)N(R_8)_2$, —$NR_8SO_2R_8$, —$OC(=Z)R_8$, —$OC(=Z)N(R_8)_2$, —$S(O)R_8$—$S(O)_2R_8$, or —$S(O)_2NR_8$, wherein said alkyl, cycloalkyl, heterocyclyl, aryl and heteroaryl are optionally substituted with one to three $R_8$ groups; and wherein two $R_8$s attached to the same N atom are optionally taken together with the attached N atom to form a 5-7 membered ring having additional 0-2 heteroatoms selected from O, S, and N, said ring being optionally substituted with one to three $R_8$ groups;

each $R_8$ is independently H, alkyl, cycloalkyl, heterocyclyl, aryl, or heteroaryl, halo, —CN, —$OCF_3$, —$CF_3$, —$NO_2$, —$C_1$-$C_6$ alkyl, —OH, oxo, —SH, —$O(C_1$-$C_6$ alkyl), —$S(C_1$-$C_6$ alkyl), —$NH_2$, —$NH(C_1$-$C_6$ alkyl), —$N(C_1$-$C_6$ alkyl)$_2$, —$SO_2(C_1$-$C_6$ alkyl), —$CO_2H$, —$CO_2(C_1$-$C_6$ alkyl), —$C(O)NH_2$, —$C(O)NH(C_1$-$C_6$ alkyl), —$C(O)N(C_1$-$C_6$ alkyl)$_2$, —$N(C_1$-$C_6$ alkyl)$C(O)(C_1$-$C_6$ alkyl), —$NHC(O)(C_1$-$C_6$ alkyl), —$NHSO_2(C_1$-$C_6$ alkyl), —$N(C_1$-$C_6$ alkyl)$SO_2(C_1$-$C_6$ alkyl), —$SO_2NH_2$, —$SO_2NH(C_1$-$C_6$ alkyl), —$SO_2N(C_1$-$C_6$ alkyl)$_2$, —$OC(O)NH_2$, —$OC(O)NH(C_1$-$C_6$ alkyl), —$OC(O)N(C_1$-$C_6$ alkyl)$_2$, —$NHC(O)NH(C_1$-$C_6$ alkyl), —$NHC(O)N(C_1$-$C_6$ alkyl)$_2$, —$N(C_1$-$C_6$ alkyl)$C(O)NH(C_1$-$C_6$ alkyl), —$N(C_1$-$C_6$ alkyl)$C(O)N(C_1$-$C_6$ alkyl)$_2$, —$NHC(O)NH(C_1$-$C_6$ alkyl), —$NHC(O)N(C_1$-$C_6$ alkyl)$_2$, —$NHC(O)O(C_1$-$C_6$ alkyl), or —$N(C_1$-$C_6$ alkyl)$C(O)O(C_1$-$C_6$ alkyl), wherein said alkyl, cycloalkyl, heterocyclyl, aryl, or heteroaryl is optionally substituted with one to three groups selected from halo, —CN, —$OCF_3$, —$CF_3$, —$NO_2$, —$C_1$-$C_6$ alkyl, —OH, oxo, —SH, —$O(C_1$-$C_6$ alkyl), —$S(C_1$-$C_6$ alkyl), —$NH_2$, —$NH(C_1$-$C_6$ alkyl), —$N(C_1$-$C_6$ alkyl)$_2$, —$SO_2(C_1$-$C_6$ alkyl), —$CO_2H$, —$CO_2(C_1$-$C_6$ alkyl), —$C(O)NH_2$, —$C(O)NH(C_1$-$C_6$ alkyl), —$C(O)N(C_1$-$C_6$ alkyl)$_2$, —$N(C_1$-$C_6$ alkyl)$C(O)(C_1$-$C_6$ alkyl), —$NHC(O)(C_1$-$C_6$ alkyl), —$NHSO_2(C_1$-$C_6$ alkyl), —$N(C_1$-$C_6$ alkyl)$SO_2(C_1$-$C_6$ alkyl), —$SO_2NH_2$, —$SO_2NH(C_1$-$C_6$ alkyl), —$SO_2N(C_1$-$C_6$ alkyl)$_2$, —$OC(O)NH_2$, —$OC(O)NH(C_1$-$C_6$ alkyl), —$OC(O)N(C_1$-$C_6$ alkyl)$_2$, —$NHC(O)NH(C_1$-$C_6$ alkyl), —$NHC(O)N(C_1$-$C_6$ alkyl)$_2$, —$N(C_1$-$C_6$ alkyl)$C(O)NH(C_1$-$C_6$ alkyl), —$N(C_1$-$C_6$ alkyl)$C(O)N(C_1$-$C_6$ alkyl)$_2$, —$NHC(O)NH(C_1$-$C_6$ alkyl), —$NHC(O)N(C_1$-$C_6$ alkyl)$_2$, —$NHC(O)O(C_1$-$C_6$ alkyl), and —$N(C_1$-$C_6$ alkyl)$C(O)O(C_1$-$C_6$ alkyl); and wherein two R8s attached to the same N atom are optionally taken together with the attached N atom to form a 5-7 membered ring having additional 0-2 heteroatoms selected from O, S, and N, said ring being optionally substituted with one to three groups selected from halo, —CN, —$OCF_3$, —$CF_3$, —$NO_2$, —$C_1$-$C_6$ alkyl, —OH, oxo, —SH, —$O(C_1$-$C_6$ alkyl), —$S(C_1$-$C_6$ alkyl), —$NH_2$, —$NH(C_1$-$C_6$ alkyl), —$N(C_1$-$C_6$ alkyl)$_2$, —$SO_2(C_1$-$C_6$ alkyl), —$CO_2H$, —$CO_2(C_1$-$C_6$ alkyl), —$C(O)NH_2$, —$C(O)NH(C_1$-$C_6$ alkyl), —$C(O)N(C_1$-$C_6$ alkyl)$_2$, —$N(C_1$-$C_6$ alkyl)$C(O)(C_1$-$C_6$ alkyl), —$NHC(O)(C_1$-$C_6$ alkyl), —$NHSO_2(C_1$-$C_6$ alkyl), —$N(C_1$-$C_6$ alkyl)$SO_2(C_1$-$C_6$ alkyl), —$SO_2NH_2$, —$SO_2NH(C_1$-$C_6$ alkyl), —$SO_2N(C_1$-$C_6$ alkyl)$_2$, —$OC(O)NH_2$, —$OC(O)NH(C_1$-$C_6$ alkyl), —$OC(O)N(C_1$-$C_6$ alkyl)$_2$, —$NHC(O)NH(C_1$-$C_6$ alkyl), —$NHC(O)N(C_1$-$C_6$ alkyl)$_2$, —$N(C_1$-$C_6$ alkyl)$C(O)NH(C_1$-$C_6$ alkyl), —$N(C_1$-$C_6$ alkyl)$C(O)N(C_1$-$C_6$ alkyl)$_2$, —$NHC(O)NH(C_1$-$C_6$ alkyl), —$NHC(O)N(C_1$-$C_6$ alkyl)$_2$, —$NHC(O)O(C_1$-$C_6$ alkyl), and —$N(C_1$-$C_6$ alkyl)$C(O)O(C_1$-$C_6$ alkyl);

each Z is independently O or S.

The present invention includes a composition (for example, a pharmaceutical composition) comprising a compound of formula (I), (II), (III), (IV), and/or (V) (and/or solvates, hydrates and/or salts thereof) and a carrier (a pharmaceutically acceptable carrier). The present invention also includes a composition (for example, a pharmaceutical composition) comprising a compound of formula (I), (II), (III), (IV), and/or (V) (and/or solvates, hydrates and/or salts thereof) and a carrier (a pharmaceutically acceptable carrier), further comprising a second chemotherapeutic agent. The present compositions are therefore useful for inhibiting abnormal cell growth or treating a hyperproliferative disorder in a mammal (for example, human), such as cancer.

The present invention includes a method of inhibiting abnormal cell growth or treating a hyperproliferative disorder in a mammal (for example, human) such as cancer comprising administering to said mammal a therapeutically effective amount of a compound of formula (I), (II), (III), (IV), and/or (V) (and/or solvates, hydrates and/or salts thereof) or a composition thereof, alone or in combination with a second chemotherapeutic agent.

The present invention includes a method of using the present compounds for in vitro, in situ, and in vivo diagnosis or treatment of mammalian cells, organisms, or associated pathological conditions. The compositions and methods of the invention may be useful in the treatment of a hematopoietic malignancy, such as non-Hodgkin's lymphoma, diffuse large hematopoietic lymphoma, follicular lymphoma, mantle cell lymphoma, chronic lymphocytic leukemia, multiple myeloma, AML, and MCL. The compositions may inhibit tumor growth in mammals and may be useful for treating human cancer patients.

In one aspect, the invention includes a method for the treatment of a hematopoietic malignancy comprising administering a therapeutic combination as a combined formulation or by alternation to a mammal, wherein the therapeutic combination comprises a therapeutically effective amount of a compound having formula (I), (II), (III), (IV), and/or (V), and a therapeutically effective amount of a chemotherapeutic agent selected from a PI3K inhibitor such as 4-(2-(1H-indazol-4-yl)-6-((4-(methylsulfonyl)piperazin-1-yl)methyl)thieno[3,2-d]pyrimidin-4-yl)morpholine (US 2008/0076768; U.S. Pat. No. 7,750,002; Folkes et al (2008) Jour. of Med. Chem. 51(18):5522-5532), also known as GDC-0941 (Genentech, Inc.) and having Formula A, or (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (US 2008/0242665) having Formula B.

DETAILED DESCRIPTION

Figure 1:
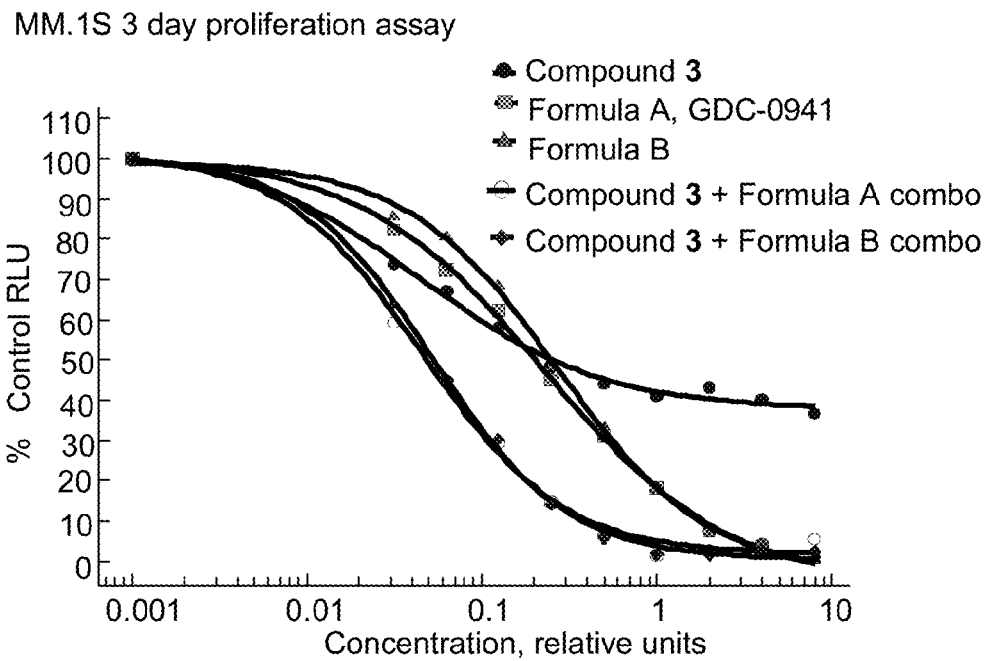
FIG. 1 shows the effect of PIM single agent inhibitor, (S)-5-amino-N-(4-(3-aminopiperidin-1-yl)pyridin-3-yl)-2-(2,6-difluorophenyl)thiazole-4-carboxamide (Compound 3, Example 3), and in combinations with GDC-0941 Formula A and Formula B on multiple myeloma cell line MM.1S in a 3 day proliferation assay. The in vitro cell survival and proliferation assay (Cell-Titer Glo, Promega) measured viable cells over varying inhibitor concentrations ($10^{-3}$ to 10 Relative Units, wherein a Relative Unit equals 0.3 micromolar for Compound 3, 0.3 micromolar for Formula A, and 0.1 micromolar for Formula B).

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

The term "alkyl" as used herein refers to a saturated linear or branched-chain monovalent hydrocarbon radical of one to twelve carbon atoms. Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (1-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, 1-heptyl, 1-octyl, and the like.

The term "alkenyl" refers to linear or branched-chain monovalent hydrocarbon radical of two to twelve carbon atoms with at least one site of unsaturation, i.e., a carbon-carbon, sp$^2$ double bond, wherein the alkenyl radical includes radicals having "cis" and "trans" orientations, or alternatively, "E" and "Z" orientations. Examples include, but are not limited to, ethylenyl or vinyl (—CH═CH$_2$), allyl (—CH$_2$CH═CH$_2$), and the like.

The term "alkynyl" refers to a linear or branched monovalent hydrocarbon radical of two to twelve carbon atoms with at least one site of unsaturation, i.e., a carbon-carbon, sp triple bond. Examples include, but are not limited to, ethynyl (—C≡CH), propynyl (propargyl, —CH$_2$C≡CH), and the like.

The term "cycloalkyl" refers to a monovalent non-aromatic, saturated or partially unsaturated ring having 3 to 12 carbon atoms as a monocyclic ring or 6 to 12 carbon atoms as a bicyclic ring. Bicyclic carbocycles having 6 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-14 carbon atoms derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronaphthalene, 1,2,3,4-tetrahydronaphthyl, and the like.

The terms "heterocycle," "heterocyclyl" and "heterocyclic ring" are used interchangeably herein and refer to a saturated or a partially unsaturated (i.e., having one or more double bonds within the ring) carbocyclic radical of 3 to 14 ring atoms in which at least one ring atom is a heteroatom selected from nitrogen, oxygen and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, and S) or a bicycle having 6 to 10 ring members (4 to 9 carbon atoms and 1 to 6 heteroatoms selected from N, O, and S), for example: a bicyclo [4,5], [5,5], [5,6], or [6,6] system or a bridged [2.1.1], [2.2.1], [2.2.2] or [3.2.2] system.

Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidinyl, morpholinyl, thiomorpholinyl, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, pyrazolidinylimidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (=O) moieties are pyrimidinonyl and 1,1-dioxo-thiomorpholinyl.

The term "heteroaryl" refers to a monovalent aromatic radical of 5- or 6-membered rings, and includes fused ring systems (at least one of which is aromatic) of 5-16 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiophene, tetrahydrothiophene, pyrrole or pyrrolidine, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, 2-oxo-1,2-dihydropyridine, or 4-oxo-1,4-dihydropyridine; position 2 of a isoindole, or isoindoline; position 4 of a morpholine; and position 9 of a carbazole, or β-carboline.

The term "halo" refers to F, Cl, Br or I. The heteroatoms present in heteroaryl or heterocyclyl include the oxidized forms such as $N^+ \rightarrow O^-$, $S(O)$ and $S(O)_2$.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "abnormal cell growth" and "hyperproliferative disorder" are used interchangeably in this application. "Abnormal cell growth", as used herein, unless otherwise indicated, refers to cell growth that is independent of normal regulatory mechanisms. This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells. Tumors include solid and liquid tumors. Examples of cancer include, but are not limited to, carcinoma, lymphoma, blastoma, sarcoma, myeloma, and hematopoietic malignancies including leukemia and lymphoid. More particular examples of such cancers include squamous cell cancer (for example, epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, malignant brain tumors, melanoma, endometrial or uterine carcinoma, salivary gland carcinoma, kidney or renal cancer, prostate cancer, vulval cancer, thyroid cancer, hepatic carcinoma, anal carcinoma, penile carcinoma, head and neck cancer, acute myelogenous leukemia (AML), chronic myelogenous leukemia (CML), acute lymphoblastic leukemia (ALL), chronic lymphocytic leukemia (CLL), T-cell lymphoma, and B-cell lymphoma including all of the B-cell lymphoma subtypes including but not limited to follicular lymphoma (FL), diffuse large B-cell lymphoma (DL-BCL), marginal zone lymphoma (MZ), mucosal-associated lymphoid tissue lymphoma (MALT), mantle cell lymphoma (MCL), other less frequent subtypes of lymphoma, and plasma cell disorders including multiple myeloma (MM) and Waldenstrom's macroglobulinemia.

A subject or mammal is successfully "treated" for a hematopoietic malignancy, such as non-Hodgkin's lymphoma, if after receiving a therapeutic amount of the therapeutic combination according to the methods of the invention, the patient shows one or more of: (i) observable and/or measurable reduction in the number of cancer cells or absence of the cancer cells; (ii) reduction in the tumor size; inhibition (i.e., slow to some extent and preferably stop) of cancer cell infiltration into peripheral organs including the spread of cancer into soft tissue and bone; (iii) inhibition (i.e., slow to some extent and preferably stop) of tumor metastasis; (iv) inhibition, to some extent, of tumor growth; or (v) relief to some extent, of one or more of the symptoms associated with the specific cancer, including reduced morbidity and mortality and improvement in quality of life. To the extent the therapeutic combination may prevent growth and/or kill existing cancer cells, it may be cytostatic and/or cytotoxic. Reduction of these signs or symptoms may also be felt by the patient. The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively.

The term "hematopoietic malignancy" refers to a cancer or hyperproliferative disorder generated during hematopoiesis involving cells such as leukocytes, lymphocytes, natural killer cells, plasma cells, and myeloid cells such as neutrophils and monocytes. Hematopoietic malignancies include the diseases listed below (I-IX), the WHO classification of Human Hematopoietic Malignancies; Tumors of Hematopoietic and Lymphoid Tissues (Jaffe E. S., Harris N. L., Stein H., Vardiman J. W. (Eds.) (2001): World Health Organization Classification of Tumours. Pathology and Genetics of Tumours of Hematopoietic and Lymphoid Tissues. IARC Press: Lyon) with the morphology code of the International Classification of Diseases (ICD-O). Behavior is coded/3 for malignant tumors and /1 for lesions of low or uncertain malignant potential.

I. Chronic Myeloproliferative Diseases
Chronic myelogenous leukemia—ICD-O 9875/3
Chronic neutrophilic leukemia—ICD-O 9963/3
Chronic eosinophilic leukemia/hypereosinophilic syndrome—ICD-O 9964/3
Polycythemia vera—ICD-O 9950/3
Chronic idiopathic myelofibrosis—ICD-O 9961/3
Essential thrombocytemia—ICD-O 9962/3 Chronic Myeloproliferative disease, unclassifiable—ICD-O 9975/3

II. Myelodysplastic/Myeloproliferative Diseases
Chronic myelomonocytic leukemia—ICD-O 9980/3
Atypical chronic myelogenous leukemia—ICD-O 9876/3
Juvenile myelomonocytic leukemia—ICD-O 9946/3
Myelodysplastic/myeloproliferative diseases, unclassifiable—ICD-O 9975/3

III. Myelodysplastic Syndromes
Refractory anemia—ICD-O 9980/3
Refractory anemia with ringed sideroblasts—ICD-O 9982/3
Refractory cytopenia with multilineage dysplasia—ICD-O 9985/3
Refractory anemia with excess blasts—ICD-O 9983/3
Myelodysplastic syndrome associated with isolated del (5q) chromosome abnormality—ICD-O 9986/3
Myelodysplastic syndrome, unclassifiable 9989/3

IV. Acute Myeloid Leukemias
Acute myeloid leukemias with recurrent cytogenetic abnormalities
AML with t(8;21)(q22;q22), AML1/ETO—ICD-O 9896/3
AML with inv(16)(p13q22) or t(16;16)(p13;q22), CBFb/MYH11—ICD-O 9871/3
Acute promyelocytic leukemia (AML with t(15;17)(q22;q12), PML-RARa and variants)—ICD-O 9866/3
AML with 11q23 (MLL) abnormalities—ICD-O 9897/3
Acute myeloid leukemia multilineage dysplasia—ICD-O 9895/3
Acute myeloid leukemia and myelodysplastic syndrome, therapy related—ICD-O 9920/3
Acute myeloid leukemia not otherwise categorised
Acute myeloid leukemia, minimally differentiated—ICD-O 9872/3
Acute myeloid leukemia, without maturation—ICD-O 9873/3
Acute myeloid leukemia, with maturation—ICD-O 9874/3
Acute myelomonocytic leukemia—ICD-O 9867/3
Acute monoblastic and monocytic leukemia—ICD-O 9891/3
Acute erythroid leukemia—ICD-O 9840/3
Acute megakaryoblastic leukemia—ICD-O 9910/3
Acute basophilic leukemia—ICD-O 9870/3
Acute panmyelosis with myelofibrosis—ICD-O 9931/3
Myeloid sarcoma—ICD-O 9930/3
Acute leukemia of ambiguous lineage—ICD-O 9805/3

V. B-Cell Neoplasms
Precursor hematopoietic neoplasm
Precursor B lymphoblastic leukemia/—ICD-O 9835/3
lymphoma—ICD-O 9728/3
Mature hematopoietic neoplasm
Chronic lymphocytic leukemia/—ICD-O 9823/3
small lymphocytic lymphoma—ICD-O 9670/3
hematopoietic prolymphocytic leukemia—ICD-O 9833/3
Lymphoplasmacytic lymphoma—ICD-O 9671/3
Splenic marginal zone lymphoma—ICD-O 9689/3
Hairy cell leukemia—ICD-O 9940/3
Plasma cell myeloma—ICD-O 9732/3
Solitary plasmacytoma of bone—ICD-O 9731/3
Extraosseous plasmacytoma—ICD-O 9734/3
Extranodal marginal zone hematopoietic lymphoma of mucosa-associated lymphoid tissue (MALT-lymphoma)—ICD-O 9699/3
Nodal marginal zone hematopoietic lymphoma—ICD-O 9699/3
Follicular lymphoma—ICD-O 9690/3

Mantle cell lymphoma—ICD-O 9673/3
Diffuse large hematopoietic lymphoma—ICD-O 9680/3
Mediastinal (thymic) large cell lymphoma—ICD-O 9679/3
Intravascular large hematopoietic lymphoma—ICD-O 9680/3
Primary effusion lymphoma—ICD-O 9678/3
Burkitt lymphoma/—ICD-O 9687/3
leukemia—ICD-O 9826/3
hematopoietic proliferations of uncertain malignant potential
Lymphomatoid granulomatosis—ICD-O 9766/1
Post-transplant lymphoproliferative disorder, pleomorphic—ICD-O 9970/1
VI. T-Cell and NK-Cell Neoplasms
Precursor T-cell neoplasms
Precursor T lymphoblastic leukemia/—ICD-O 9837/3
lymphoma—ICD-O 9729/3
Blastic NK cell lymphoma—ICD-O 9727/3
Mature T-cell and NK-cell neoplasms
T-cell prolymphocytic leukemia—ICD-O 9834/3
T-cell large granular lymphocytic leukemia—ICD-O 9831/3
Aggressive NK cell leukemia—ICD-O 9948/3
Adult T-cell leukemia/lymphoma—ICD-O 9827/3
Extranodal NK/T cell lymphoma, nasal type—ICD-O 9719/3
Enteropathy type T-cell lymphoma—ICD-O 9717/3
Hepatosplenic T-cell lymphoma—ICD-O 9716/3
Subcutaneous panniculitis-like T-cell lymphoma—ICD-O 9708/3
Mycosis fungoides—ICD-O 9700/3
Sezary Syndrome—ICD-O 9701/3
Primary cutaneous anaplastic large cell lymphoma—ICD-O 9718/3
Peripheral T-cell lymphoma, unspecified—ICD-O 9702/3
Angioimmunoblastic T-cell lymphoma—ICD-O 9705/3
Anaplastic large cell lymphoma—ICD-O 9714/3
T-cell proliferation of uncertain malignant potential
Lymphomatoid papulosis—ICD-O 9718/1
VII. Hodgkin Lymphoma
Nodular lymphocyte predominant Hodgkin lymphoma—ICD-O 9659/3
Classical Hodgkin lymphoma—ICD-O 9650/3
Nodular sclerosis classical Hodgkin lymphoma—ICD-O 9663/3
Lymphocyte-rich classical Hodgkin lymphoma—ICD-O 9651/3
Mixed cellularity classical Hodgkin lymphoma—ICD-O 9652/3
Lymphocyte-depleted classical Hodgkin lymphoma—ICD-O 9653/3
VIII. Histiocytic and Dendritic-Cell Neoplasms
Macrophage/histiocytic neoplasm
Histiocytic sarcoma—ICD-O 9755/3
Dendritic cell neoplasms
Langerhans cell histiocytosis—ICD-O 9751/1
Langerhans cell sarcoma—ICD-O 9756/3
Interdigitating dendritic cell sarcoma/tumor—ICD-O 9757/3/1
Follicular dendritic cell sarcoma/tumor—ICD-O 9758/3/1
Dendritic cell sarcoma, not otherwise specified—ICD-O 9757/3
IX. Mastocytosis
Cutaneous mastocytosis
Indolent systemic mastocytosis—ICD-O 9741/1
Systemic mastocytosis with associated clonal, hematological non-mast cell lineage disease—ICD-O 9741/3
Aggressive systemic mastocytosis—ICD-O 9741/3
Mast cell leukemia—ICD-O 9742/3
Mast cell sarcoma—ICD-O 9740/3
Extracutaneous mastocytoma—ICD-O 9740/1

A "B cell" is a lymphocyte that matures within the bone marrow, and includes a naïve B cell, memory B cell, or effector B cell (plasma cell). The B cell herein is a normal or non-malignant B cell.

A "chemotherapeutic agent" is a chemical compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; bestrabucil; bisantrene; edatraxate; defofamine; demecolcine; diaziquone; elformithine; elliptinium acetate; an epothilone; etoglucid; gallium nitrate; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; dacarbazine; mannomustine; mitobronitol; mitolactol; pipobroman; gacytosine; arabinoside ("Ara-C"); chloranmbucil; 6-thioguanine; mercaptopurine; ifosfamide; mitoxantrone; novantrone; edatrexate; daunomycin; aminopterin; capecitabine (XELODA®); ibandronate; CPT-11; difluoromethylornithine (DMFO); and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (for example, ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

Examples of a "chemotherapeutic agent" also include a DNA damaging agent such as thiotepa and CYTOXAN® cyclosphosphamide; alkylating agents (for example cis-platin; carboplatin; cyclophosphamide; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; busulphan; nitrosoureas such as carmustine, chlorozotocin, fotemustine, lomustine, nimustine, and ranimnustine; and temozolomide); antimetabolites (for example antifolates such as fluoropyrimidines like 5-fluorouracil (5-FU) and tegafur, raltitrexed, methotrexate, cytosine arabinoside, hydroxyurea and GEMZAR® (gemcitabine); antitumour antibiotics such as the enediyne antibiotics (for example, calicheamicin, especially calicheamicin gamma1I and calicheamicin omega1I (Angew Chem. Intl. Ed. Engl. (1994) 33:183-186); anthracyclines like adriamycin; dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin, epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; antimitotic agents (for example vinca alkaloids like vincristine, vinblastine, vindesine and NAVELBINE® (vinorelbine) and taxoids like taxoids, for example, TAXOL® (paclitaxel; Bristol-Myers Squibb Oncology, Princeton, N.J.), ABRAXANE™ (Cremophor-free), albumin-engineered nanoparticle formulations of paclitaxel (American Pharmaceutical Partners, Schaumberg, Ill.), and TAXOTERE® (doxetaxel; Rhône-Poulenc Rorer, Antony, France); topoisomerase inhibitors (for example RFS 2000, epipodophyllotoxins like etoposide and teniposide, amsacrine, a camptothecin (including the synthetic analog topotecan), and irinotecan and SN-38) and cytodifferentiating agents (for example retinoids such as all-trans retinoic acid, 13-cis retinoic acid and fenretinide); and pharmaceutically acceptable salts, acids and derivatives of any of the above.

A "chemotherapeutic agent" also includes an agent that modulates the apoptotic response including inhibitors of IAP (inhibitor of apoptosis proteins) such as AEG40826 (Aegera Therapeutics); and inhibitors of bcl-2 such as GX15-070 (Gemin X Biotechnologies), CNDO103 (Apogossypol; Coronado Biosciences), HA14-1 (ethyl 2-amino-6-bromo-4-(1-cyano-2-ethoxy-2-oxoethyl)-4H-chromene-3-carboxylate), AT101 (Ascenta Therapeutics), ABT-737 and ABT-263 (Abbott); and pharmaceutically acceptable salts, acids and derivatives of any of the above.

A "chemotherapeutic agent" that can be used in combination with the present compounds also includes inhibitors of MEK (MAP kinase kinase), such as GDC0973/XL518 (Genentech, Inc./Exelixis, Inc.) and AZD6244 (Astrazeneca); inhibitors of mTor (mammalian target of rapamycin), such as rapamycin, AP23573 (Ariad Pharmaceuticals), temsirolimus (Wyeth Pharmaceuticals) and RAD001 (Novartis); inhibitors of PI3K (phosphoinositide-3 kinase), such as SF-1126 (PI3K inhibitor, Semafore Pharmaceuticals), BEZ-235 (PI3K inhibitor, Novartis), XL-147 (PI3K inhibitor, Exelixis, Inc.), GDC-0980 (Genentech), and GDC-0941 (Genentech); inhibitors of Akt; and pharmaceutically acceptable salts, acids and derivatives of any of the above.

The term "prodrug" as used in this application refers to a precursor or derivative form of a compound of the invention that is capable of being enzymatically or hydrolytically activated or converted into the more active parent form. See, for example, Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, ester-containing prodrugs, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

A "metabolite" is a product produced through metabolism in the body of a specified compound or salt thereof. Metabolites of a compound may be identified using routine techniques known in the art and their activities determined using tests such as those described herein. Such products may result for example from the oxidation, hydroxylation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

A "liposome" is a small vesicle composed of various types of lipids, phospholipids and/or surfactant which is useful for delivery of a drug (such as chk inhibitors disclosed herein and, optionally, a chemotherapeutic agent) to a mammal. The components of the liposome are commonly arranged in a bilayer formation, similar to the lipid arrangement of biological membranes.

The term "chiral" refers to molecules which have the property of non-superimposability of the mirror image partner, while the term "achiral" refers to molecules which are superimposable on their mirror image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, for example melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons. For example, any reference to a structure of 2-hydroxypyridine include its tautomer 2-oxo-1,2-dihydropyridine, also known as 2-pyridone, and vice versa.

The phrase "pharmaceutically acceptable salt" as used herein, refers to pharmaceutically acceptable organic or inorganic salts of a compound of the invention. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 1,1'-methylene-bis-(2-hydroxy-3-naphthoate)) salts, alkali metal (for example, sodium and potassium) salts, alkaline earth metal (for example, magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, methanesulfonic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ),2-(trimethylsilyl) ethoxymethyl (SEM) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and t-butyldimethylsilyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "compound of this invention," and "compounds of the present invention", and "compounds of formula (I), (II), (III), (IV), or (V)", "compounds of formula (I), (II), (III), (IV), and/or (V)", unless otherwise indicated, include compounds of formula (I), (II), (III), (IV), and/or (V), and stereoisomers, geometric isomers, tautomers, solvates, metabolites, salts (for example, pharmaceutically acceptable salts) and prodrugs thereof. Unless otherwise stated, structures depicted herein are also meant to include compounds that differ only in the presence of one or more isotopically enriched atoms. For example, compounds of formula (I), (II), (III), (IV), or (V), wherein one or more hydrogen atoms are replaced deuterium or tritium, or one or more carbon atoms are replaced by a $^{13}$C- or $^{14}$C-enriched carbon are within the scope of this invention.

4-Substituted N-(pyridin-3-yl)carboxamides

The present invention provides 4-substituted N-(pyridin-3-yl) carboxamides of formula (I) (and/or solvates, hydrates and/or salts thereof) as described above with Pim kinase inhibitory activity, such as Pim-1, Pim-2 and/or Pim-3 inhibitory activities. The present compounds are particularly useful as pan-Pim kinase inhibitors.

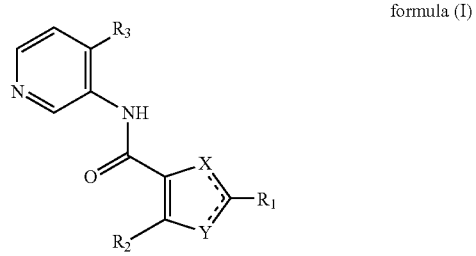

formula (I)

wherein:

X is N, S, or O;

Y is NH, N, S, or O; provided that X and Y are not S or O at the same time;

$R_1$ is H, halo, hydroxyl, nitro, cyano, alkyl, alkenyl, $OR_4$, $SR_4$, $SO_2R_4$, $SO_3R_4$, —$N(R_4)_2$, —$C(O)N(R_4)_2$, —$NR_4C(O)R_4$, —$C(S)N(R_4)_2$, —$NR_4C(S)R_4$, —$NR_4C(O)N(R_4)_2$, —$NR_4C(S)N(R_4)_2$, —$OC(O)N(R_4)_2$, —$SO_2N(R_4)_2$, —$N(R_4)SO_2R_4$, —$N(R_4)SO_2N(R_4)_2$, $NR_4C(=NH)R_4$, —$C(O)OR_4$, —$OC(O)OR_4$, cycloalkyl, heterocycloalkyl, aryl, or heteroaryl, wherein said alkyl, alkenyl, cycloalkyl, heterocycloalkyl, aryl, or heteroaryl is optionally substituted with one to three $R^4$ groups;

$R_2$ is hydrogen, halo, alkyl, cycloalkyl, —CN, —$NO_2$, and —$NHR_5$;

$R_3$ is —$N(R_4)_2$, $OR_4$, halo, cycloalkyl, heterocycloalkyl, aryl, or heteroaryl, wherein said cycloalkyl, heterocycloalkyl, aryl, or heteroaryl is optionally substituted with one to three $R^7$ groups; provided that when X is N and Y is S, then $R_3$ is not N-piperazinyl;

each $R_4$ is independently H, alkyl, cycloalkyl, heterocycloalkyl, aryl, heteroaryl, halo, CN, $CF_3$, —$OCF_3$, —$NO_2$, oxo, —C(=Z)$R_7$, —C(=Z)$OR_7$, —C(=Z)N($R_7$)$_2$, —N($R_7$)$_2$, —$OR_7$, —$SR_7$, —$NR_7C$(=Z)$R_7$, —$NR_7C$(=Z)$OR_7$, —$NR_7C$(=Z)N($R_7$)$_2$, —$NR_7SO_2R_7$, —OC(=Z)$R_7$, —OC(=Z)N($R_7$)$_2$, —S(O)$R_7$, —S(O)$_2R_7$, or —S(O)$_2NR_7$, wherein said alkyl, cycloalkyl, heterocycloalkyl, aryl, or heteroaryl is optionally substituted with one to three $R_7$ groups; and wherein two $R_4$s attached to the same N atom are optionally taken together with the attached N atom to form a 5-7 membered ring having additional 0-2 heteroatoms selected from O, S, and N, said ring being optionally substituted with one to three $R_7$ groups;

$R_5$ is H, —$COR_6$, alkyl, cycloalkyl, heterocyclyl, aryl, or heteroaryl, wherein said alkyl, cycloalkyl, heterocyclyl, aryl, or heteroaryl is optionally substituted with one to three $R_7$ groups;

$R_6$ is alkyl, $OR_4$, or —$N(R_4)_2$;

each $R_7$ is independently H, alkyl, cycloalkyl, heterocyclyl, aryl, heteroaryl, halo, CN, $CF_3$, —$OCF_3$, —$NO_2$, oxo, —C(=Z)$R_8$, —C(=Z)$OR_8$, —C(=Z)N($R_8$)$_2$, —N($R_8$)$_2$, —$OR_8$, —$SR_8$, —$NR_8C$(=Z)$R_8$, —$NR_8C$(=Z)$OR_8$, —$NR_8C$(=Z)N($R_8$)$_2$, —$NR_8SO_2R_8$, —OC(=Z)$R_8$, —OC(=Z)N($R_8$)$_2$, —S(O)$R_8$—S(O)$_2R_8$, or —S(O)$_2NR_8$, wherein said alkyl, cycloalkyl, heterocyclyl, aryl and heteroaryl are optionally substituted with one to three $R_8$ groups; and wherein two $R_8$s attached to the same N atom are optionally taken together with the attached N atom to form a 5-7 membered ring having additional 0-2 heteroatoms selected from O, S, and N, said ring being optionally substituted with one to three $R_8$ groups;

each $R_8$ is independently H, alkyl, cycloalkyl, heterocyclyl, aryl, or heteroaryl, halo, —CN, —$OCF_3$, —$CF_3$, —$NO_2$, —$C_1$-$C_6$ alkyl, —OH, oxo, —SH, —O($C_1$-$C_6$ alkyl), —S($C_1$-$C_6$ alkyl), —$NH_2$, —NH($C_1$-$C_6$ alkyl), —N($C_1$-$C_6$ alkyl)$_2$, —$SO_2$($C_1$-$C_6$ alkyl), —$CO_2H$, —$CO_2$($C_1$-$C_6$ alkyl), —C(O)$NH_2$, —C(O)NH($C_1$-$C_6$ alkyl), —C(O)N($C_1$-$C_6$ alkyl)$_2$, —N($C_1$-$C_6$ alkyl)C(O)($C_1$-$C_6$ alkyl), —NHC(O)($C_1$-$C_6$ alkyl), —$NHSO_2$($C_1$-$C_6$ alkyl), —N($C_1$-$C_6$ alkyl)$SO_2$($C_1$-$C_6$ alkyl), —$SO_2NH_2$, —$SO_2NH$($C_1$-$C_6$ alkyl), —$SO_2N$($C_1$-$C_6$ alkyl)$_2$, —OC(O)$NH_2$, —OC(O)NH($C_1$-$C_6$ alkyl), —OC(O)N($C_1$-$C_6$ alkyl)$_2$, —NHC(O)NH($C_1$-$C_6$ alkyl), —NHC(O)N($C_1$-$C_6$ alkyl)$_2$, —N($C_1$-$C_6$ alkyl)C(O)NH($C_1$-$C_6$ alkyl), —N($C_1$-$C_6$ alkyl)C(O)N($C_1$-$C_6$ alkyl)$_2$, —NHC(O)NH($C_1$-$C_6$ alkyl), —NHC(O)N($C_1$-$C_6$ alkyl)$_2$, —NHC(O)O($C_1$-$C_6$ alkyl), or —N($C_1$-$C_6$ alkyl)C(O)O($C_1$-$C_6$ alkyl), wherein said alkyl, cycloalkyl, heterocyclyl, aryl, or heteroaryl is optionally substituted with one to three groups selected from halo, —CN, —$OCF_3$, —$CF_3$, —$NO_2$, —$C_1$-$C_6$ alkyl, —OH, oxo, —SH, —O($C_1$-$C_6$ alkyl), —S($C_1$-$C_6$ alkyl), —$NH_2$, —NH($C_1$-$C_6$ alkyl), —N($C_1$-$C_6$ alkyl)$_2$, —$SO_2$($C_1$-$C_6$ alkyl), —$CO_2H$, —$CO_2$($C_1$-$C_6$ alkyl), —C(O)$NH_2$, —C(O)NH($C_1$-$C_6$ alkyl), —C(O)N($C_1$-$C_6$ alkyl)$_2$, —N($C_1$-$C_6$ alkyl)C(O)($C_1$-$C_6$ alkyl), —NHC(O)($C_1$-$C_6$ alkyl), —$NHSO_2$($C_1$-$C_6$ alkyl), —N($C_1$-$C_6$ alkyl)$SO_2$($C_1$-$C_6$ alkyl), —$SO_2NH_2$, —$SO_2NH$($C_1$-$C_6$ alkyl), —$SO_2N$($C_1$-$C_6$ alkyl)$_2$, —OC(O)$NH_2$, —OC(O)NH($C_1$-$C_6$ alkyl), —OC(O)N($C_1$-$C_6$ alkyl)$_2$, —NHC(O)NH($C_1$-$C_6$ alkyl), —NHC(O)N($C_1$-$C_6$ alkyl)$_2$, —N($C_1$-$C_6$ alkyl)C(O)NH($C_1$-$C_6$ alkyl), —N($C_1$-$C_6$ alkyl)C(O)N($C_1$-$C_6$ alkyl)$_2$, —NHC(O)NH($C_1$-$C_6$ alkyl), —NHC(O)N($C_1$-$C_6$ alkyl)$_2$, —NHC(O)O($C_1$-$C_6$ alkyl), and —N($C_1$-$C_6$ alkyl)C(O)O($C_1$-$C_6$ alkyl); and wherein two R8s attached to the same N atom are optionally taken together with the attached N atom to form a 5-7 membered ring having additional 0-2 heteroatoms selected from O, S, and N, said ring being optionally substituted with one to three groups selected from halo, —CN, —OCF$_3$, —CF$_3$, —NO$_2$, —C$_1$-C$_6$ alkyl, —OH, oxo, —SH, —O(C$_1$-C$_6$ alkyl), —S(C$_1$-C$_6$ alkyl), —NH$_2$, —NH(C$_1$-C$_6$ alkyl), —N(C$_1$-C$_6$ alkyl)$_2$, —SO$_2$(C$_1$-C$_6$ alkyl), —CO$_2$H, —CO$_2$(C$_1$-C$_6$ alkyl), —C(O)NH$_2$, —C(O)NH(C$_1$-C$_6$ alkyl), —C(O)N(C$_1$-C$_6$ alkyl)$_2$, —N(C$_1$-C$_6$ alkyl)C(O)(C$_1$-C$_6$ alkyl), —NHC(O)(C$_1$-C$_6$ alkyl), —NHSO$_2$(C$_1$-C$_6$ alkyl), —N(C$_1$-C$_6$ alkyl)SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —OC(O)NH$_2$, —OC(O)NH(C$_1$-C$_6$ alkyl), —OC(O)N(C$_1$-C$_6$ alkyl)$_2$, —NHC(O)NH(C$_1$-C$_6$ alkyl), —NHC(O)N(C$_1$-C$_6$ alkyl)$_2$, —N(C$_1$-C$_6$ alkyl)C(O)NH(C$_1$-C$_6$ alkyl), —N(C$_1$-C$_6$ alkyl)C(O)N(C$_1$-C$_6$ alkyl)$_2$, —NHC(O)NH(C$_1$-C$_6$ alkyl), —NHC(O)N(C$_1$-C$_6$ alkyl)$_2$, —NHC(O)O(C$_1$-C$_6$ alkyl), and —N(C$_1$-C$_6$ alkyl)C(O)O(C$_1$-C$_6$ alkyl);

each Z is independently O or S.

In certain embodiments of the present invention, X is N or S; and all other variables are as defined for formula (I). In certain embodiments of the present invention, X is N; and all other variables are as defined for formula (I). In certain embodiments of the present invention, X is S; and all other variables are as defined for formula (I). The dashed lines ----- between X, Y, and the carbon atom bearing X and Y indicate the inclusion of formula (Ia) and (Ib) isomers as compounds of the invention. Each ----- represents a single bond or a double bond; and with the proviso that these bonds between X, Y, and the carbon atom bearing X and Y are not both double bonds and are not both single bonds.

In certain embodiments, formula (I) compounds have the structure of formula (Ia) or formula (Ib):

formula (Ia)

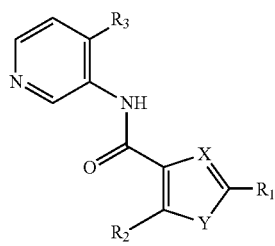

formula (Ib)

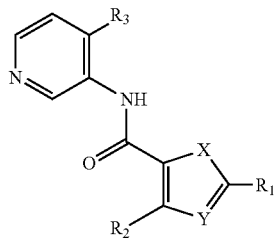

where all other variables are as defined for formula (I).

In certain embodiments of the present invention, Y is NH; and all other variables are as defined for formula (I) or as defined in one of the embodiments described above. In certain embodiments of the present invention, Y is S; and all other variables are as defined for formula (I) or as defined in one of the embodiments described above. In certain embodiments of the present invention, Y is O; and all other variables are as defined for formula (I) or as defined in one of the embodiments described above.

In certain embodiments of the present invention, a compound is of formula (II), (III), (IV) or (V), and all other variables are as defined for formula (I).

(II)

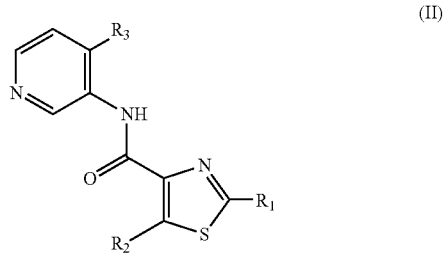

(III)

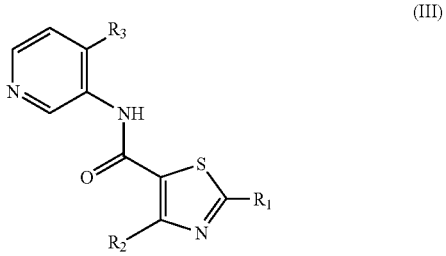

(IV)

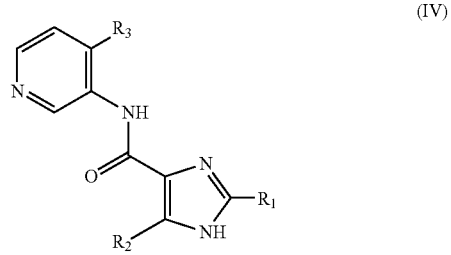

(V)

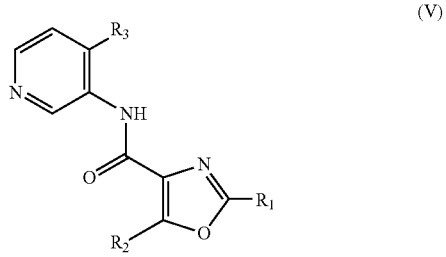

In certain embodiments of the present invention, R$_1$ is H, alkyl, cycloalkyl, aryl, or heteroaryl, wherein said alkyl, cycloalkyl, aryl, or heteroaryl is optionally substituted with one to three R$^4$ groups, and all other variables are as defined in formula (I), (II), (III), (IV), or (V) or as defined in any one of the embodiments described above.

In certain embodiments of the present invention, R$_1$ is:

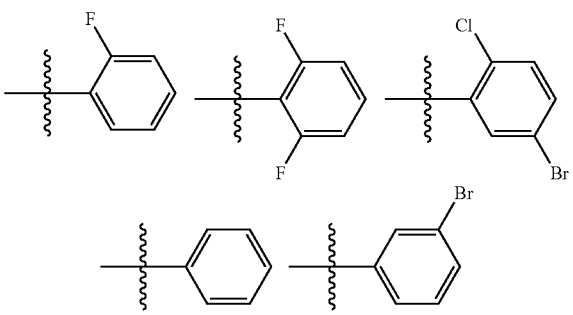

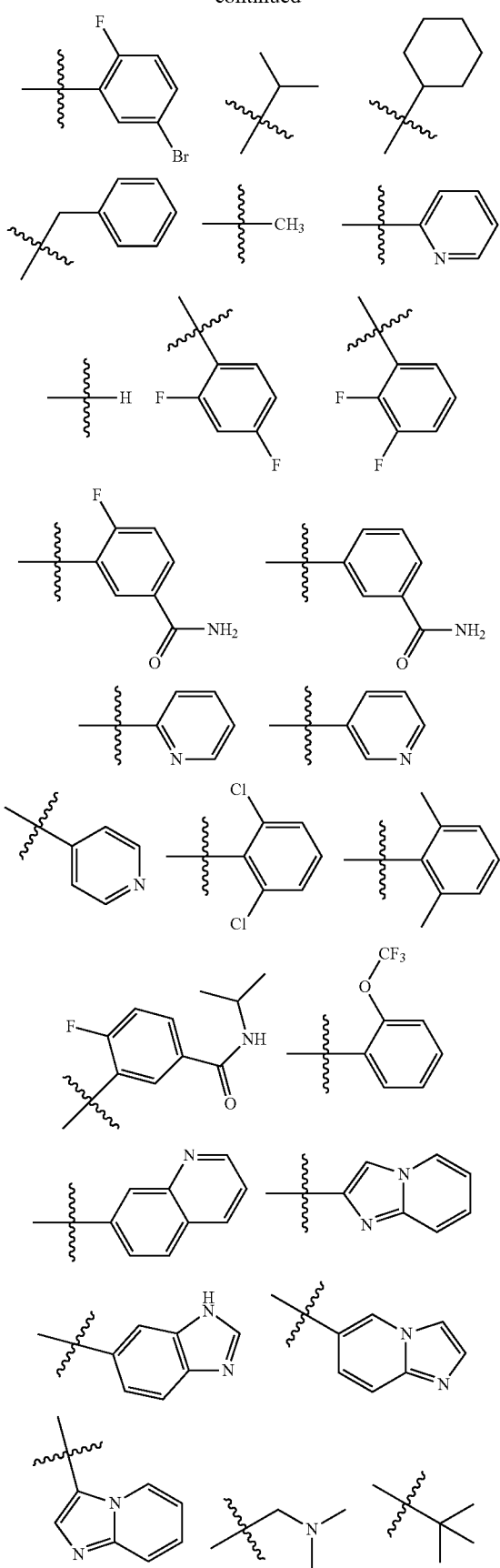
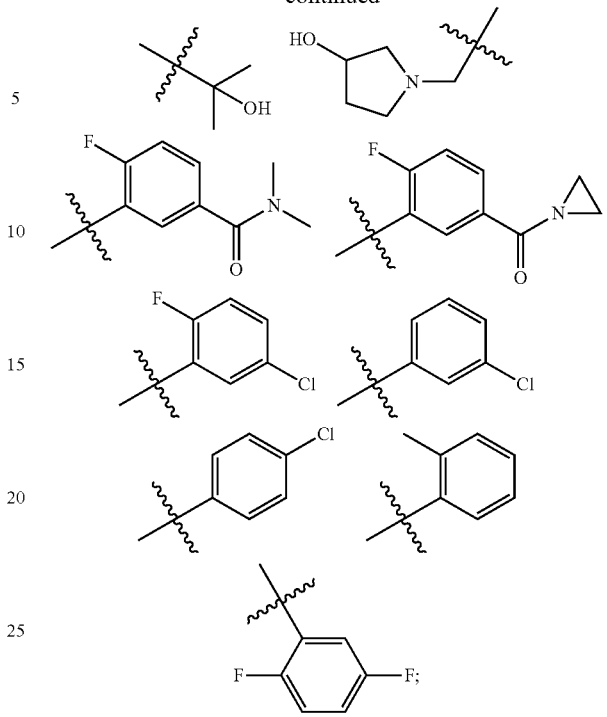

and all other variables are as defined in formula (I), (II), (III), (IV), or (V) or as defined in any one of the embodiments described above.

In certain embodiments of the present invention, $R_2$ is H or $NH_2$, and all other variables are as defined in formula (I), (II), (III), (IV), or (V) or as defined in any one of the embodiments described above.

In certain embodiments of the present invention, $R_2$ is H, and all other variables are as defined in formula (I), (II), (III), (IV), or (V) or as defined in any one of the embodiments described above. In certain embodiments of the present invention, $R_2$ is $NH_2$, and all other variables are as defined in formula (I), (II), (III), (IV), or (V) or as defined in any one of the embodiments described above.

In certain embodiments of the present invention, $R_3$ is halo or $N(R_4)_2$ wherein two $R_4$ groups are taken care to the attached N atom to form a 5-6 membered ring having additional 0-2 heteroatoms selected from O, S, and N, said ring being optionally substituted with one to three $R_7$ groups, and all other variables are as defined in formula (I), (II), (III), (IV), or (V) or as defined in any one of the embodiments described above.

In certain embodiments of the present invention, $R_3$ is halo, and all other variables are as defined in formula (I), (II), (III), (IV), or (V) or as defined in any one of the embodiments described above. In certain embodiments of the present invention, $R_3$ is Cl, and all other variables are as defined in formula (I), (II), (III), (IV), or (V) or as defined in any one of the embodiments described above.

In certain embodiments of the present invention, $R_3$ is $N(R_4)_2$ wherein two $R_4$ groups are taken care to the attached N atom to form a 5-6 membered ring having additional 0-2 heteroatoms selected from O, S, and N, said ring being optionally substituted with one to three $R_7$ groups, and all other variables are as defined in formula (I), (II), (III), (IV), or (V) or as defined in any one of the embodiments described above.

In certain embodiments of the present invention, $R_3$ is:

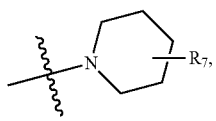

and all other variables are as defined in formula (I), (II), (III), (IV), or (V) or as defined in any one of the embodiments described above.

In certain embodiments of the present invention, $R_3$ is:

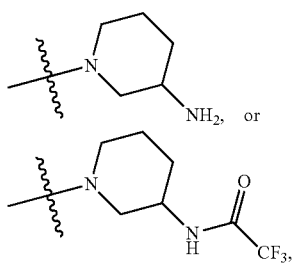

and all other variables are as defined in formula (I), (II), (III), (IV), or (V) or as defined in any one of the embodiments described above.

In certain embodiments of the present invention, $R_3$ is:

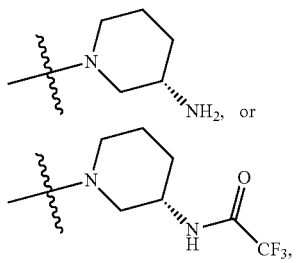

and all other variables are as defined in formula (I), (II), (III), (IV), or (V) or as defined in any one of the embodiments described above.

Another embodiment of the present invention includes title compounds described in EXAMPLES 1-66 below.

The present compounds are prepared according to the procedures described below in the schemes and examples, or by methods known in the art. The starting materials and various intermediates may be obtained from commercial sources, prepared from commercially available compounds, or prepared using well known synthetic methods. Accordingly, methods for making the present compounds of formula (I) according to Schemes 1-5 are within the scope of the present invention.

Scheme 1

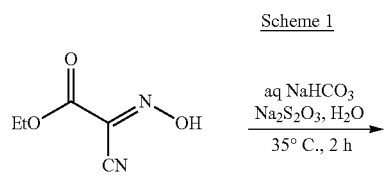

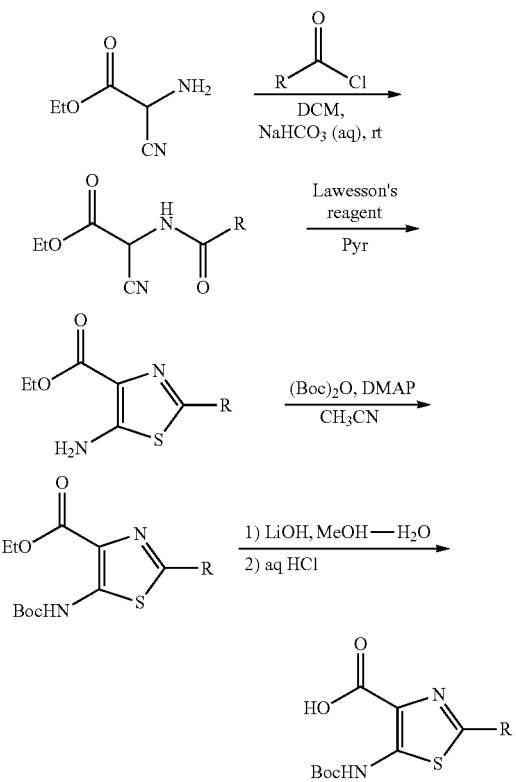

Scheme 2

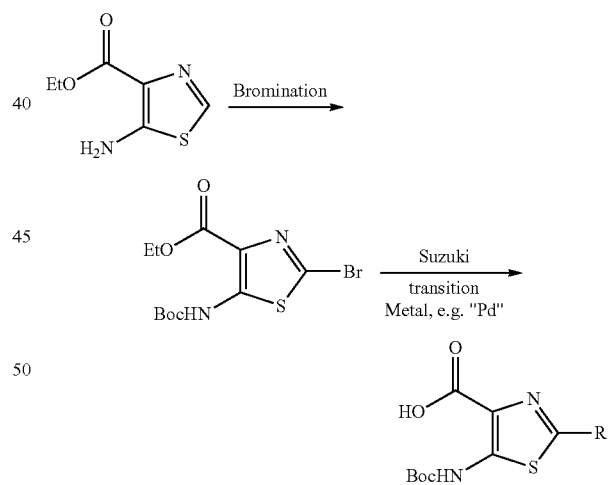

Scheme 3

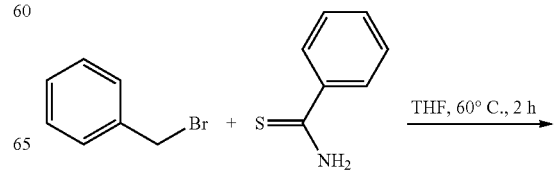

27
-continued
28
Scheme 4
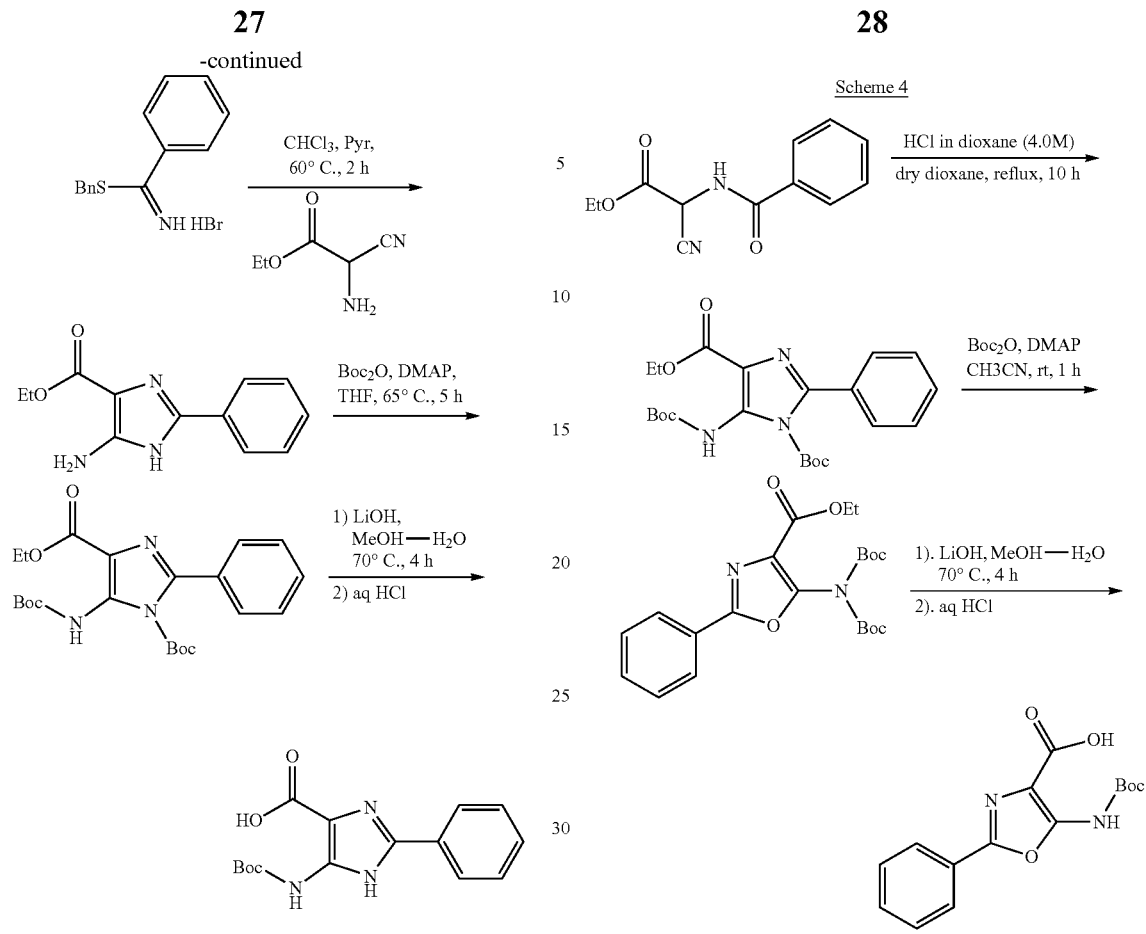
Scheme 5
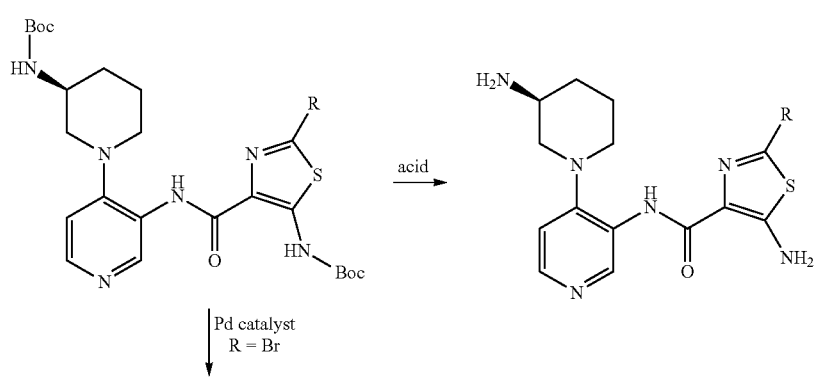

-continued

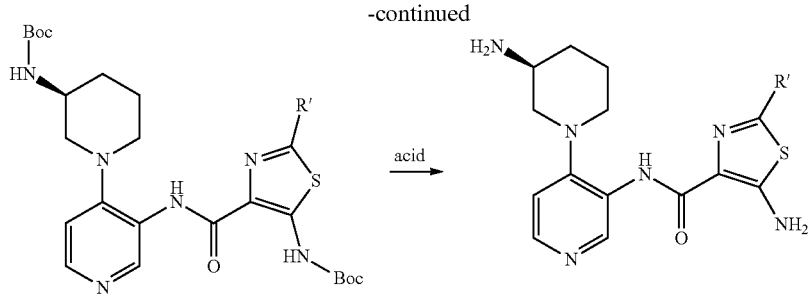

The compounds of the present invention are tested for their capacity to inhibit Pim kinase activity and for their biological effects on growing cells as described below in EXAMPLES i and ii. The compounds having $Ki/IC_{50}/EC_{50}$ of less than 10 μM (preferably less than 1 μM, more preferably less than 0.1 μM, even more preferably less than 0.01 μM, most preferably less than 0.001 μM) in assays described in EXAMPLES i and ii, are useful as Pim kinase inhibitors (Pim-1, Pim-2 and/or Pim-3).

Exemplary Formula I compounds in Table 1 were made, characterized, and tested for inhibition of Pim kinase according to the methods of this invention, and have the following structures and corresponding names (ChemDraw Ultra, Version 9.0.1, CambridgeSoft Corp., Cambridge Mass.).

TABLE 1

| Ex. | Structure | Name |
|---|---|---|
| 1 | 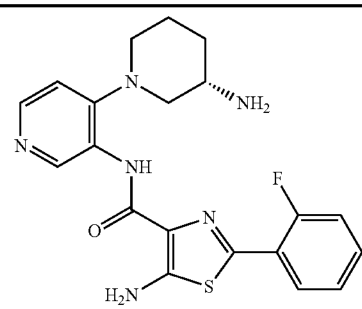 | (S)-5-amino-N-(4-(3-aminopiperidin-1-yl)pyridin-3-yl)-2-(2-fluorophenyl)thiazole-4-carboxamide |
| 2 | 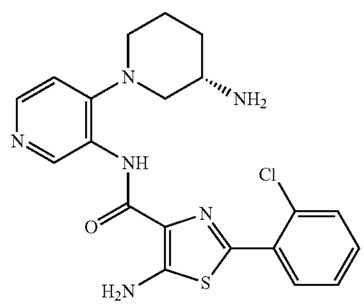 [SMILES: Nc1sc(-c2ccccc2Cl)nc1C(=O)Nc1cnccc1N1CCC[C@H](N)C1] | (S)-5-amino-N-(4-(3-aminopiperidin-1-yl)pyridin-3-yl)-2-(2-chlorophenyl)thiazole-4-carboxamide |
| 3 | 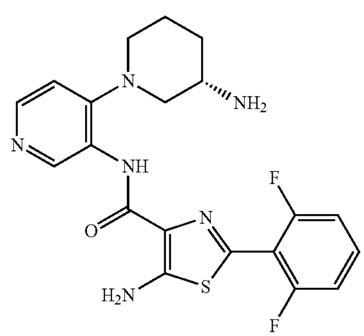 [SMILES: Nc1sc(-c2c(F)cccc2F)nc1C(=O)Nc1cnccc1N1CCC[C@H](N)C1] | (S)-5-amino-N-(4-(3-aminopiperidin-1-yl)pyridin-3-yl)-2-(2,6-difluorophenyl)thiazole-4-carboxamide |

TABLE 1-continued

| Ex. | Structure | Name |
|---|---|---|
| 4 | 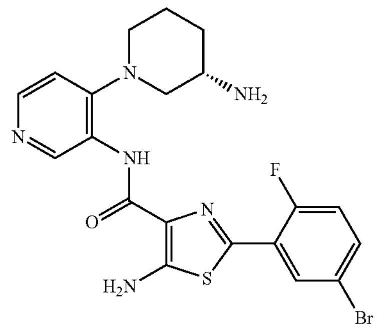 [SMILES: Nc1sc(-c2cc(Br)ccc2F)nc1C(=O)Nc1cnccc1N1CCC[C@H](N)C1] | (S)-5-amino-N-(4-(3-aminopiperidin-1-yl)pyridin-3-yl)-2-(5-bromo-2-fluorophenyl)thiazole-4-carboxamide |
| 5 | 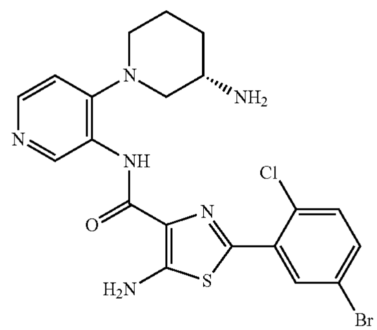 [SMILES: Nc1sc(-c2cc(Br)ccc2Cl)nc1C(=O)Nc1cnccc1N1CCC[C@H](N)C1] | (S)-5-amino-N-(4-(3-aminopiperidin-1-yl)pyridin-3-yl)-2-(5-bromo-2-chlorophenyl)thiazole-4-carboxamide |
| 6 | 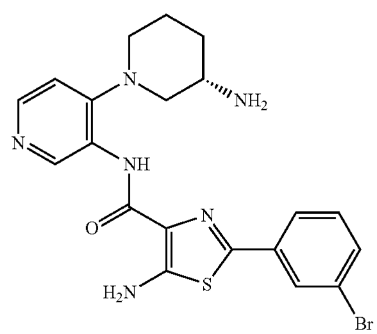 [SMILES: Nc1sc(-c2cccc(Br)c2)nc1C(=O)Nc1cnccc1N1CCC[C@H](N)C1] | (S)-5-amino-N-(4-(3-aminopiperidin-1-yl)pyridine-3-yl)-2-(3-bromophenyl)thiazole-4-carboxamide |
| 7 | 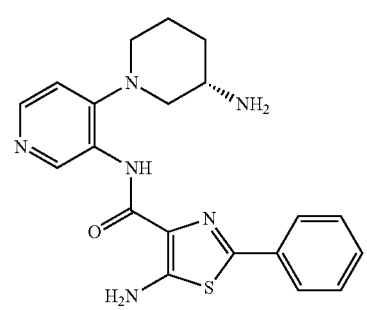 [SMILES: Nc1sc(-c2ccccc2)nc1C(=O)Nc1cnccc1N1CCC[C@H](N)C1] | (S)-5-amino-N-(4-(3-aminopiperidin-1-yl)pyridin-3-yl)-2-phenylthiazole-4-carboxamide |
| 8 | 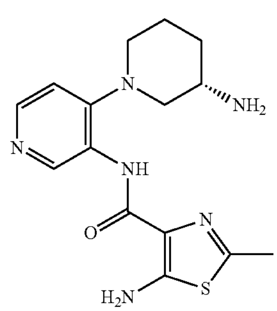 [SMILES: Cc1nc(C(=O)Nc2cnccc2N2CCC[C@H](N)C2)c(N)s1] | (S)-5-amino-N-(4-(3-aminopiperidin-1-yl)pyridin-3-yl)-2-methylthiazole-4-carboxamide |

TABLE 1-continued

| Ex. | Structure | Name |
|---|---|---|
| 9 | 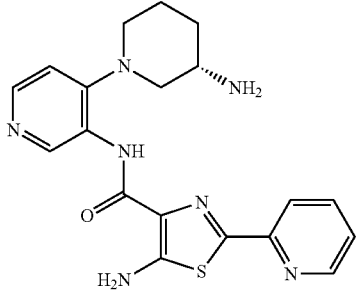 | (S)-5-amino-N-(4-(3-aminopiperidin-1-yl)pyridin-3-yl)-2-(pyridin-2-yl)thiazole-4-carboxamide |
| 10 | 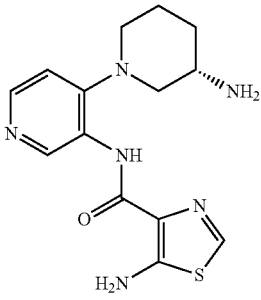 [SMILES: Nc1scnc1C(=O)Nc1cnccc1N1CCC[C@H](N)C1] | (S)-5-amino-N-(4-(3-aminopiperidin-1-yl)pyridin-3-yl)thiazole-4-carboxamide |
| 11 | 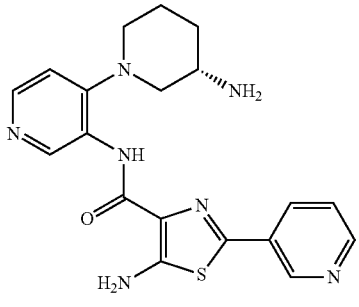 [SMILES: Nc1sc(-c2cccnc2)nc1C(=O)Nc1cnccc1N1CCC[C@H](N)C1] | (S)-5-amino-N-(4-(3-aminopiperidin-1-yl)pyridin-3-yl)-2-(pyridin-3-yl)thiazole-4-carboxamide |
| 12 | 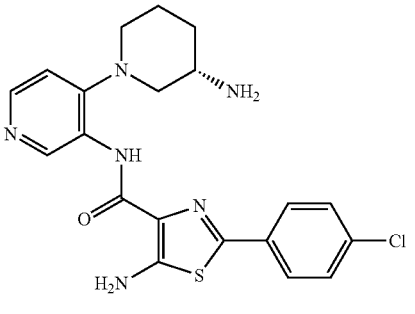 [SMILES: Nc1sc(-c2ccc(Cl)cc2)nc1C(=O)Nc1cnccc1N1CCC[C@H](N)C1] | (S)-5-amino-N-(4-(3-aminopiperidin-1-yl)pyridin-3-yl)-2-(4-chlorophenyl)thiazole-4-carboxamide |
| 13 | 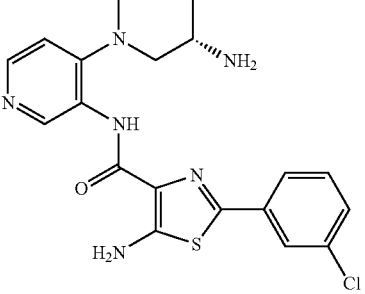 | (S)-5-amino-N-(4-(3-aminopiperidin-1-yl)pyridin-3-yl)-2-(3-chlorophenyl)thiazole-4-carboxamide |

TABLE 1-continued

| Ex. | Structure | Name |
|---|---|---|
| 14 | 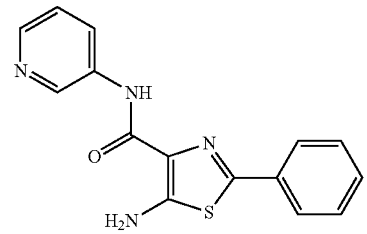 [SMILES: Nc1sc(-c2ccccc2)nc1C(=O)Nc1cccnc1] | 5-amino-2-phenyl-N-(pyridine-3-yl)thiazole-4-carboxamide |
| 15 | 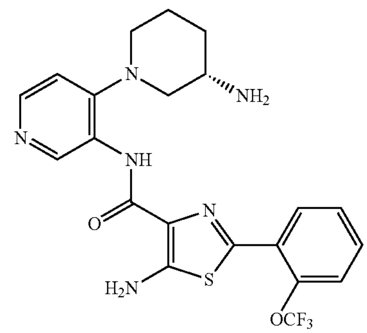 [SMILES: Nc1sc(-c2ccccc2OC(F)(F)F)nc1C(=O)Nc1cnccc1N1CCC[C@H](N)C1] | (S)-5-amino-N-(4-(3-aminopiperidin-1-yl)pyridine-3-yl)-2-(trifluoromethoxy)phenyl)thiazole-4-carboxamide |
| 16 | 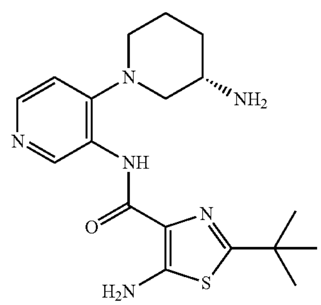 [SMILES: CC(C)(C)c1nc(C(=O)Nc2cnccc2N2CCC[C@H](N)C2)c(N)s1] | (S)-5-amino-N-(4-(3-aminopiperidin-1-yl)pyridin-3-yl)-2-tert-butylthiazole-4-carboxamide |
| 17 | 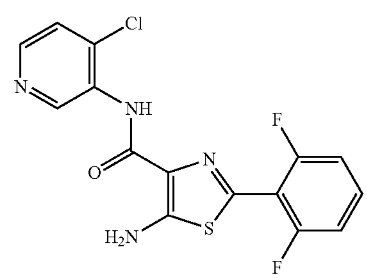 [SMILES: Nc1sc(-c2c(F)cccc2F)nc1C(=O)Nc1cnccc1Cl] | 5-amino-N-(4-chloropyridin-3-yl)-2-(2,6-difluorophenyl)thiazole-4-carboxamide |
| 18 | 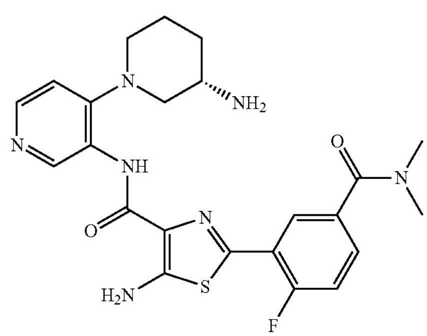 [SMILES: CN(C)C(=O)c1ccc(F)c(-c2nc(C(=O)Nc3cnccc3N3CCC[C@H](N)C3)c(N)s2)c1] | (S)-5-amino-N-(4-(3-aminopiperidin-1-yl)pyridine-3-yl)-2-(5-(dimethylcarbamoyl)-2-fluorophenyl)thiazole-4-carboxamide |

TABLE 1-continued

| Ex. | Structure | Name |
|---|---|---|
| 19 | 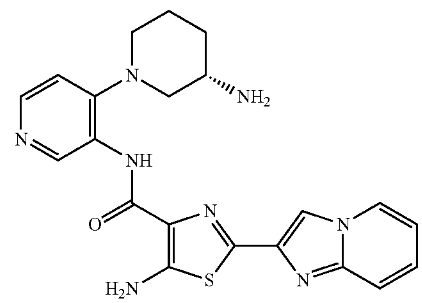 [SMILES: Nc1sc(-c2cn3ccccc3n2)nc1C(=O)Nc1cnccc1N1CCC[C@H](N)C1] | (S)-5-amino-N-(4-(3-aminopiperidin-1-yl)pyridine-3-yl)-2-(imidazo[1,2-a]pyridine-2-yl)thiazole-4-carboxamide |
| 20 | 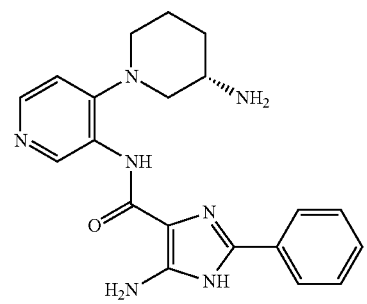 [SMILES: Nc1[nH]c(-c2ccccc2)nc1C(=O)Nc1cnccc1N1CCC[C@H](N)C1] | (S)-5-amino-N-(4-(3-aminopiperidin-1-yl)pyridin-3-yl)-2-phenyl-1H-imidazole-4-carboxamide |
| 21 | 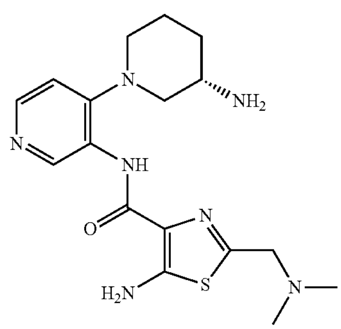 [SMILES: CN(C)Cc1nc(C(=O)Nc2cnccc2N2CCC[C@H](N)C2)c(N)s1] | (S)-5-amino-N-(4-(3-aminopiperidin-1-yl)pyridine-3-yl)-2-((dimethylamino)methyl)thiazole-4-carboxamide |
| 22 | 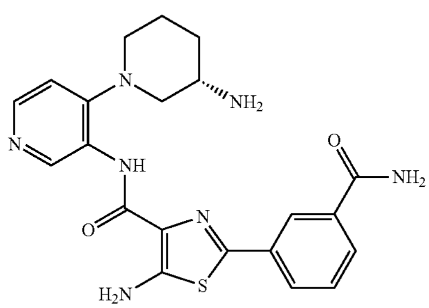 [SMILES: NC(=O)c1cccc(-c2nc(C(=O)Nc3cnccc3N3CCC[C@H](N)C3)c(N)s2)c1] | (S)-5-amino-N-(4-(3-aminopiperidin-1-yl)pyridin-3-yl)-2-(3-carbamoylphenyl)thiazole-4-carboxamide |
| 23 | 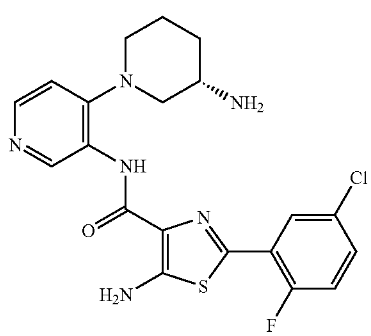 [SMILES: Nc1sc(-c2cc(Cl)ccc2F)nc1C(=O)Nc1cnccc1N1CCC[C@H](N)C1] | (S)-5-amino-N-(4-(3-aminopiperidin-1-yl)pyridin-3-yl)-2-(5-chloro-2-fluorophenyl)thiazole-4-carboxamide |

TABLE 1-continued

| Ex. | Structure | Name |
|---|---|---|
| 24 | 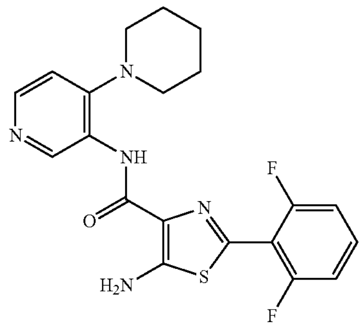 [SMILES: Nc1sc(-c2c(F)cccc2F)nc1C(=O)Nc1cnccc1N1CCCCC1] | 5-amino-2-(2,6-difluorophenyl)-N-(4-(piperidin-1-yl)pyridin-3-yl)thiazole-4-carboxamide |
| 25 | 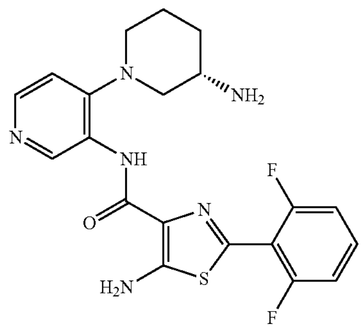 [SMILES: Nc1sc(-c2c(F)cccc2F)nc1C(=O)Nc1cnccc1N1CCC[C@H](N)C1] | (S)-5-amino-N-(4-(3-aminopiperidin-1-yl)pyridine-3-yl)-2-(2,6-difluorophenyl)thiazole-4-carboxamide |
| 26 | 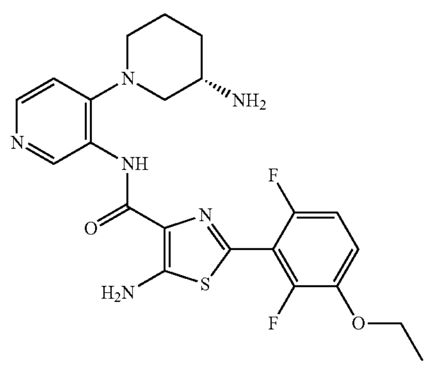 [SMILES: CCOc1ccc(F)c(-c2nc(C(=O)Nc3cnccc3N3CCC[C@H](N)C3)c(N)s2)c1F] | (S)-5-amino-N-(4-(3-aminopiperidin-1-yl)pyridine-3-yl)-2-(3-ethoxy-2,6-difluorophenyl)thiazole-4-carboxamide |
| 27 | 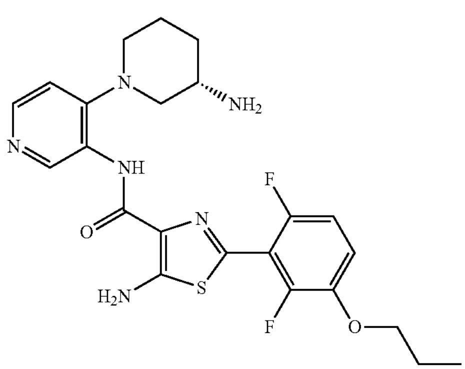 [SMILES: CCCOc1ccc(F)c(-c2nc(C(=O)Nc3cnccc3N3CCC[C@H](N)C3)c(N)s2)c1F] | (S)-5-amino-N-(4-(3-aminopiperidin-1-yl)pyridin-3-yl)-2-(3-propyloxy-2,6-difluorophenyl)thiazole-4-carboxamide |

TABLE 1-continued

| Ex. | Structure | Name |
|---|---|---|
| 28 | 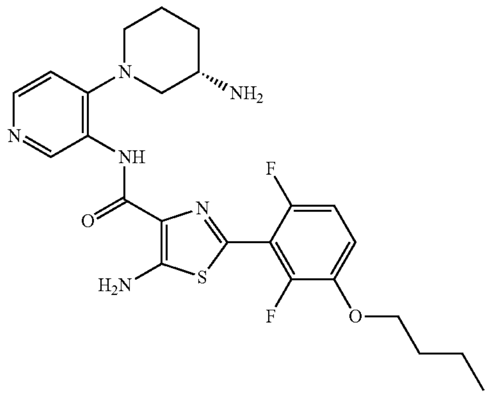 [SMILES: CCCCOc1ccc(F)c(-c2nc(C(=O)Nc3cnccc3N3CCC[C@H](N)C3)c(N)s2)c1F] | (S)-5-amino-N-(4-(3-aminopiperidin-1-yl)pyridin-3-yl)-2-(3-butyloxy-2,6-difluorophenyl)thiazole-4-carboxamide |
| 29 | 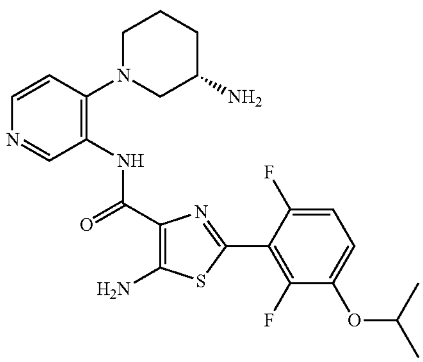 [SMILES: CC(C)Oc1ccc(F)c(-c2nc(C(=O)Nc3cnccc3N3CCC[C@H](N)C3)c(N)s2)c1F] | (S)-5-amino-N-(4-(3-aminopiperidin-1-yl)pyridine-3-yl)-2-(3-isopropyloxy-2,6-difluorophenyl)thiazole-4-carboxamide |
| 30 | 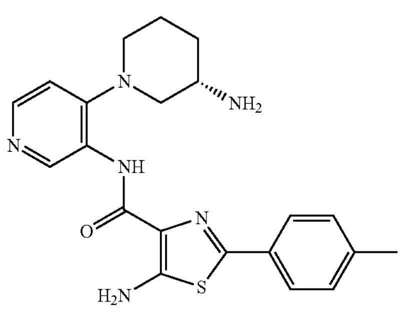 [SMILES: Cc1ccc(-c2nc(C(=O)Nc3cnccc3N3CCC[C@H](N)C3)c(N)s2)cc1] | (S)-5-amino-N-(4-(3-aminopiperidin-1-yl)pyridine-3-yl)-2-(4-tolylthiazole)-4-carboxamide |
| 31 | 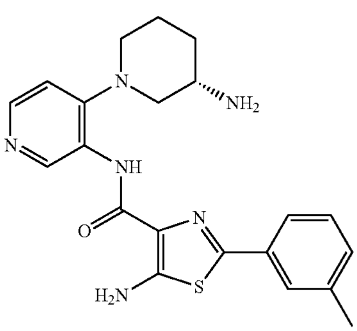 [SMILES: Cc1cccc(-c2nc(C(=O)Nc3cnccc3N3CCC[C@H](N)C3)c(N)s2)c1] | (S)-5-amino-N-(4-(3-aminopiperidin-1-yl)pyridine-3-yl)-2-(3-tolylthiazole)-4-carboxamide |

TABLE 1-continued

| Ex. | Structure | Name |
|---|---|---|
| 32 | 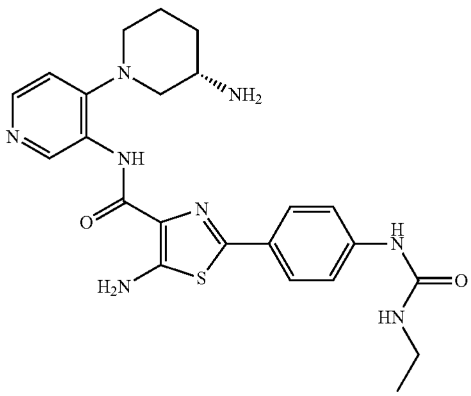 [SMILES: CCNC(=O)Nc1ccc(-c2nc(C(=O)Nc3cnccc3N3CCC[C@H](N)C3)c(N)s2)cc1] | (S)-5-amino-N-(4-(3-aminopiperidin-1-yl)pyridin-3-yl)-2-(4-(3-ethylureido)phenyl)thiazole-4-carboxamide |
| 33 | 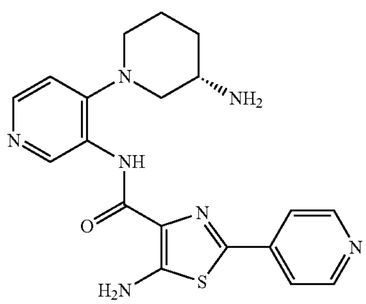 [SMILES: Nc1sc(-c2ccncc2)nc1C(=O)Nc1cnccc1N1CCC[C@H](N)C1] | (S)-5-amino-N-(4-(3-aminopiperidin-1-yl)pyridine-3-yl)-2-(pyridine-4-yl)thiazole-4-carboxamide |
| 34 | 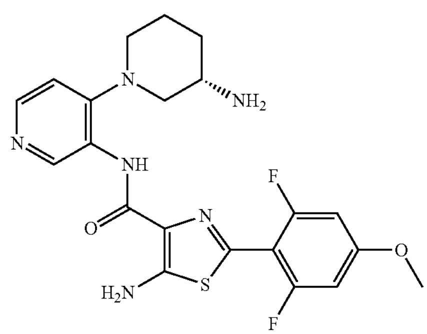 [SMILES: COc1cc(F)c(-c2nc(C(=O)Nc3cnccc3N3CCC[C@H](N)C3)c(N)s2)c(F)c1] | (S)-5-amino-N-(4-(3-aminopiperidin-1-yl)pyridine-3-yl)-2-(2,6-difluoro-4-methoxyphenyl)thiazole-4-carboxamide |
| 35 | 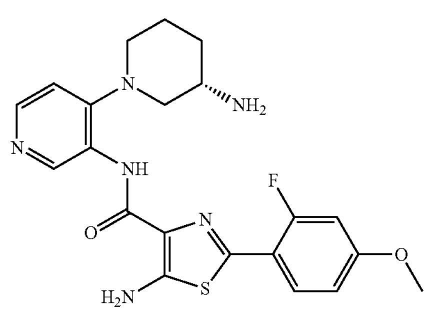 [SMILES: COc1ccc(-c2nc(C(=O)Nc3cnccc3N3CCC[C@H](N)C3)c(N)s2)c(F)c1] | (S)-5-amino-N-(4-(3-aminopiperidin-1-yl)pyridine-3-yl)-2-(2-fluoro-4-methoxyphenyl)thiazole-4-carboxamide |

TABLE 1-continued

| Ex. | Structure | Name |
|---|---|---|
| 36 | 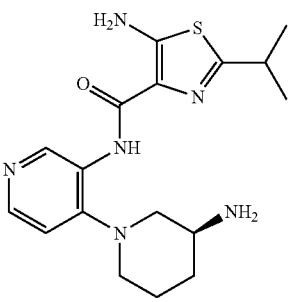 [SMILES: CC(C)c1nc(C(=O)Nc2cnccc2N2CCC[C@H](N)C2)c(N)s1] | (S)-5-amino-N-(4-(3-aminopiperidin-1-yl)pyridine-3-yl)-2-isopropylthiazole-4-carboxamide |
| 37 | 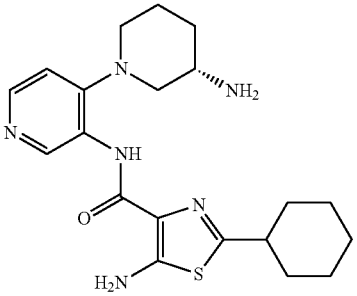 [SMILES: Nc1sc(C2CCCCC2)nc1C(=O)Nc1cnccc1N1CCC[C@H](N)C1] | (S)-5-amino-N-(4-(3-aminopiperidin-1-yl)pyridin-3-yl)-2-cyclohexylthiazole-4-carboxamide |
| 38 | 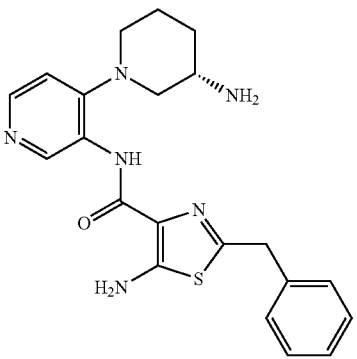 [SMILES: Nc1sc(Cc2ccccc2)nc1C(=O)Nc1cnccc1N1CCC[C@H](N)C1] | (S)-5-amino-N-(4-(3-aminopiperidin-1-yl)pyridine-3-yl)-2-benzylthiazole-4-carboxamide |
| 39 | 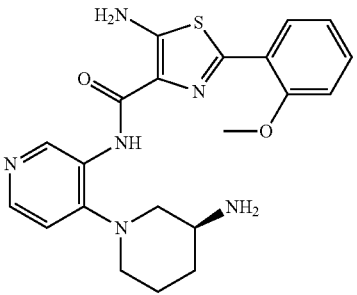 [SMILES: COc1ccccc1-c1nc(C(=O)Nc2cnccc2N2CCC[C@H](N)C2)c(N)s1] | (S)-5-amino-N-(4-(3-aminopiperidin-1-yl)pyridine-3-yl)-2-(2-methoxyphenyl)thiazole-4-carboxamide |
| 40 | 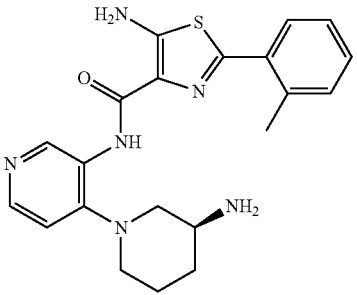 [SMILES: Cc1ccccc1-c1nc(C(=O)Nc2cnccc2N2CCC[C@H](N)C2)c(N)s1] | (S)-5-amino-N-(4-(3-aminopiperidin-1-yl)pyridine-3-yl)-2-o-tolylthiazole-4-carboxamide |

| Ex. | Structure | Name |
|---|---|---|
| 41 | 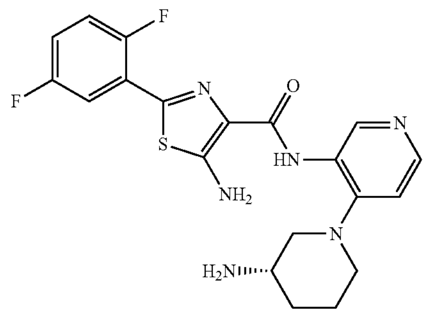 [SMILES: Nc1sc(-c2cc(F)ccc2F)nc1C(=O)Nc1cnccc1N1CCC[C@H](N)C1] | (S)-5-amino-N-(4-(3-aminopiperidin-1-yl)pyridine-3-yl)-2-(2,5-difluorophenyl)thiazole-4-carboxamide |
| 42 | 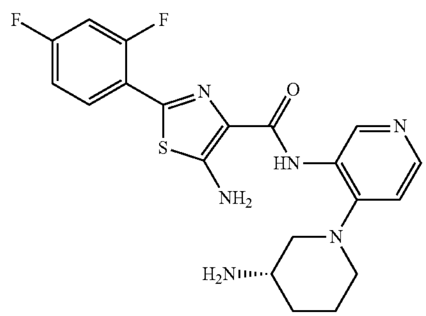 [SMILES: Nc1sc(-c2ccc(F)cc2F)nc1C(=O)Nc1cnccc1N1CCC[C@H](N)C1] | (S)-5-amino-N-(4-(3-aminopiperidin-1-yl)pyridin-3-yl)-2-(2,4-difluorophenyl)thiazole-4-carboxamide |
| 43 | 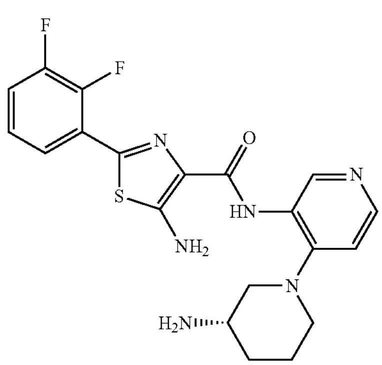 [SMILES: Nc1sc(-c2cccc(F)c2F)nc1C(=O)Nc1cnccc1N1CCC[C@H](N)C1] | (S)-5-amino-N-(4-(3-aminopiperidin-1-yl)pyridine-3-yl)-2-(2,3-difluorophenyl)thiazole-4-carboxamide |
| 44 | 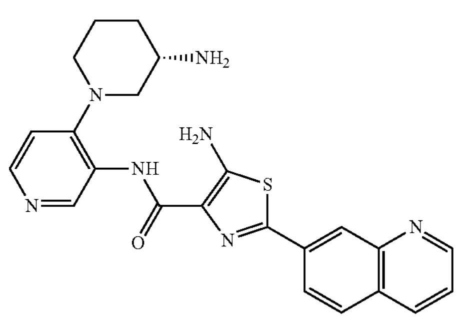 [SMILES: Nc1sc(-c2ccc3cccnc3c2)nc1C(=O)Nc1cnccc1N1CCC[C@H](N)C1] | (S)-5-amino-N-(4-(3-aminopiperidin-1-yl)pyridine-3-yl)-2-(quinolin-7-yl)thiazole-4-carboxamide |

TABLE 1-continued

| Ex. | Structure | Name |
|---|---|---|
| 45 | 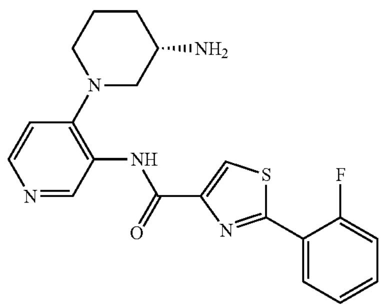 [SMILES: N[C@H]1CCCN(c2ccncc2NC(=O)c2csc(-c3ccccc3F)n2)C1] | (S)-N-(4-(3-aminopiperidin-1-yl)pyridine-3-yl)-2-(2-fluorophenyl)thiazole-4-carboxamide |
| 46 | 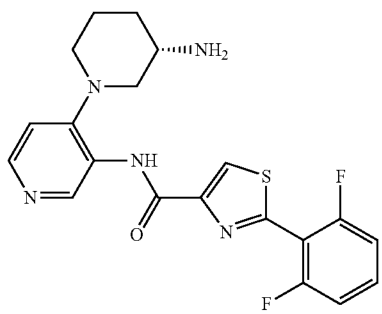 [SMILES: N[C@H]1CCCN(c2ccncc2NC(=O)c2csc(-c3c(F)cccc3F)n2)C1] | (S)-N-(4-(3-aminopiperidin-1-yl)pyridine-3-yl)-2-(2,6-difluorophenyl)thiazole-4-carboxamide |
| 47 | 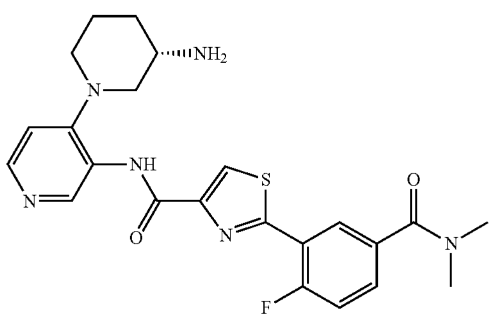 [SMILES: CN(C)C(=O)c1ccc(F)c(-c2nc(C(=O)Nc3cnccc3N3CCC[C@H](N)C3)cs2)c1] | (S)-N-(4-(3-aminopiperidin-1-yl)pyridin-3-yl)-2-(5-(dimethylcarbamoyl)-2-fluorophenyl)thiazole-4-carboxamide |
| 48 | 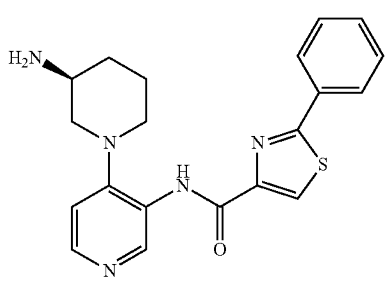 [SMILES: N[C@H]1CCCN(c2ccncc2NC(=O)c2csc(-c3ccccc3)n2)C1] | (S)-N-(4-(3-aminopiperidin-1-yl)pyridine-3-yl)-2-phenylthiazole-4-carboxamide |
| 49 | 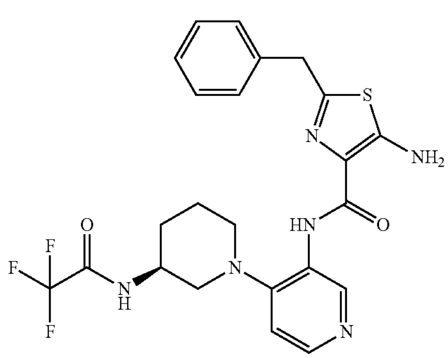 [SMILES: Nc1sc(Cc2ccccc2)nc1C(=O)Nc1cnccc1N1CCC[C@H](NC(=O)C(F)(F)F)C1] | (S)-5-amino-2-benzyl-N-(4-(3-(2,2,2-trifluoroacetamido)piperidin-1-yl)yridine-3-yl)thiazole-4-carboxamide |

TABLE 1-continued

| Ex. | Structure | Name |
|---|---|---|
| 50 | 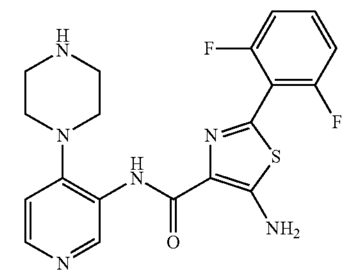 [SMILES: Nc1sc(-c2c(F)cccc2F)nc1C(=O)Nc1cnccc1N1CCNCC1] | 5-amino-2-(2,6-difluorophenyl)-N-(4-(piperazin-1-yl)pyridin-3-yl)thiazole-4-carboxamide |
| 51 | 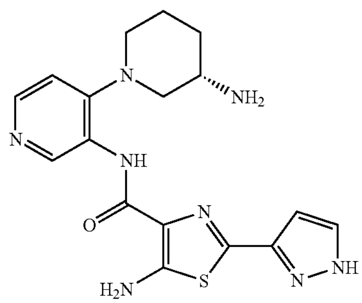 [SMILES: Nc1sc(-c2cc[nH]n2)nc1C(=O)Nc1cnccc1N1CCC[C@H](N)C1] | (S)-5-amino-N-(4-(3-aminopiperidin-1-yl)pyridin-3-yl)-2-(1H-pyrazol-3-yl)thiazole-4-carboxamide |
| 52 | 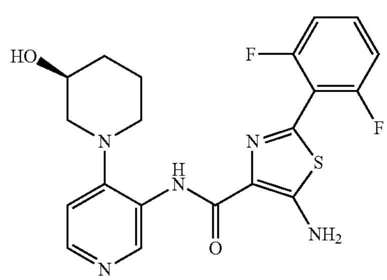 [SMILES: Nc1sc(-c2c(F)cccc2F)nc1C(=O)Nc1cnccc1N1CCC[C@H](O)C1] | (S)-5-amino-2-(2,6-difluorophenyl)-N-(4-(3-hydroxypiperidin-1-yl)pyridin-3-yl)thiazole-4-carboxamide |
| 53 | 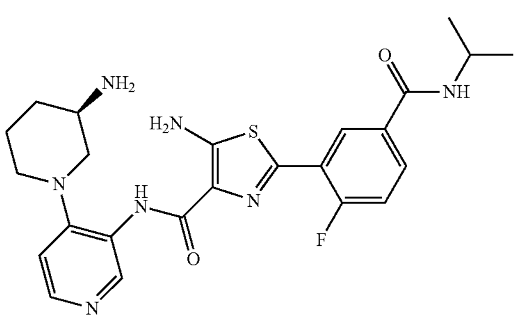 [SMILES: CC(C)NC(=O)c1ccc(F)c(-c2nc(C(=O)Nc3cnccc3N3CCC[C@@H](N)C3)c(N)s2)c1] | (R)-5-amino-N-(4-(3-aminopiperidin-1-yl)pyridin-3-yl)-2-(2-fluoro-5-(isopropylcarbamoyl)phenyl)thiazole-4-carboxamide |
| 54 | 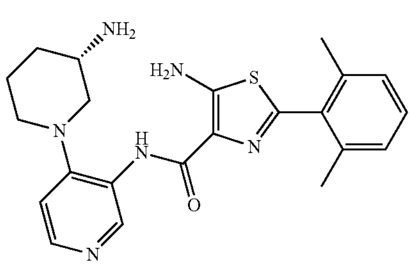 [SMILES: Cc1cccc(C)c1-c1nc(C(=O)Nc2cnccc2N2CCC[C@H](N)C2)c(N)s1] | (S)-5-amino-N-(4-(3-aminopiperidin-1-yl)pyridin-3-yl)-2-(2,6-dimethylphenyl)thiazole-4-carboxamide |

TABLE 1-continued

| Ex. | Structure | Name |
|---|---|---|
| 55 | 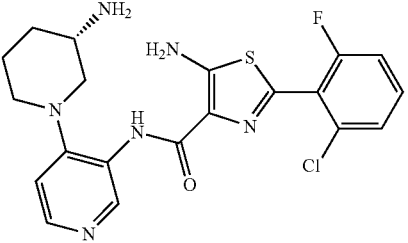 [SMILES: Nc1sc(-c2c(F)cccc2Cl)nc1C(=O)Nc1cnccc1N1CCC[C@H](N)C1] | (S)-5-amino-N-(4-(3-aminopiperidin-1-yl)pyridin-3-yl)-2-(2-chloro-6-fluorophenyl)thialole-4-carboxamide |
| 56 | 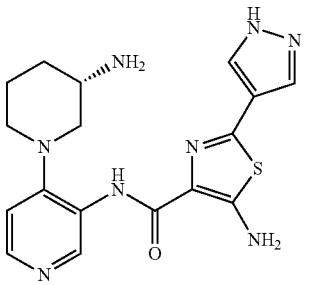 [SMILES: Nc1sc(-c2cn[nH]c2)nc1C(=O)Nc1cnccc1N1CCC[C@H](N)C1] | (S)-5-amino-N-(4-(3-aminopiperidin-1-yl)pyridin-3-yl)-2-(1H-pyrazol-4-yl)thiazole-4-carboxamide |
| 57 | 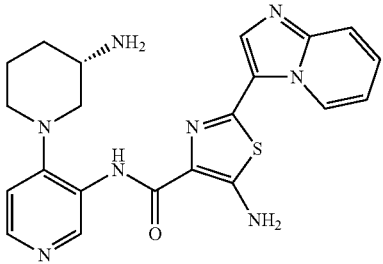 [SMILES: Nc1sc(-c2cnc3ccccn23)nc1C(=O)Nc1cnccc1N1CCC[C@H](N)C1] | (S)-5-amino-N-(4-(3-aminopiperidin-1-yl)pyridin-3-yl)-2-(imidazo[1,2-a]pyridin-3-yl)thiazole-4-carboxamide |
| 58 | 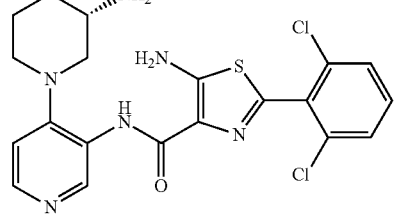 | (S)-5-amino-N-(4-(3-aminopiperidin-1-yl)pyridin-3-yl)-2-(2,6-dichlorophenyl)thiazole-4-carboxamide |
| 59 | 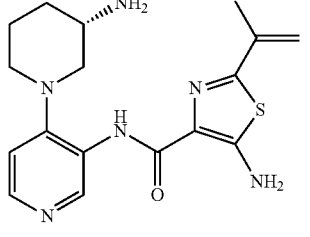 | (S)-5-amino-N-(4-(3-aminopiperidin-1-yl)pyridin-3-yl)-2-(prop-1-en-2-yl)thiazole-4-carboxamide |
| 60 | 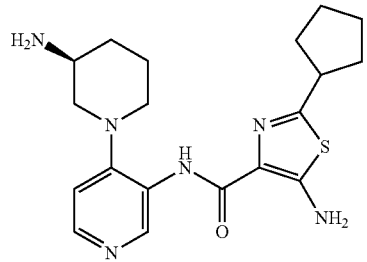 [SMILES: Nc1sc(C2CCCC2)nc1C(=O)Nc1cnccc1N1CCC[C@H](N)C1] | (S)-5-amino-N-(4-(3-aminopiperidin-1-yl)pyridin-3-yl)-2-cyclopentylthiazole-4-carboxamide |

| Ex. | Structure | Name |
|---|---|---|
| 61 | 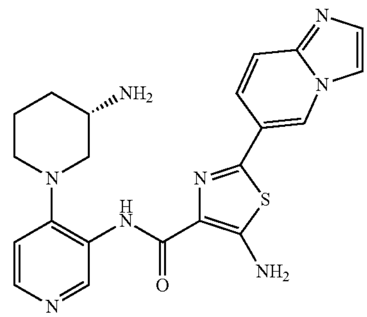 [SMILES: Nc1sc(-c2ccc3nccn3c2)nc1C(=O)Nc1cnccc1N1CCC[C@H](N)C1] | (S)-5-amino-N-(4-(3-aminopiperidin-1-yl)pyridin-3-yl)-2-(imidazo[1,2-a]pyridin-6-yl)thiazole-4-carboxamide |
| 62 | 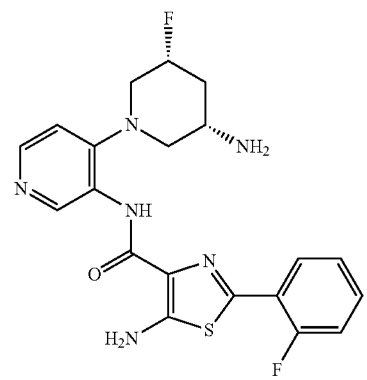 [SMILES: Nc1sc(-c2ccccc2F)nc1C(=O)Nc1cnccc1N1C[C@@H](N)C[C@@H](F)C1] | 5-amino-N-(4-((3S,5R)-3-amino-5-fluoropiperidin-1-yl)pyridin-3-yl)-2-(2-fluorophenyl)thiazole-4-carboxamide |
| 63 | 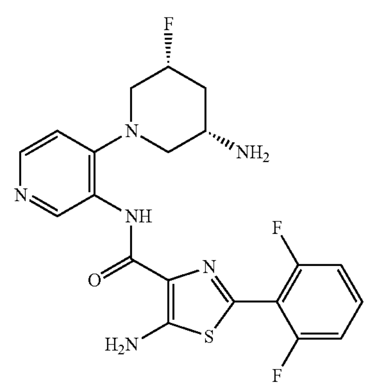 [SMILES: Nc1sc(-c2c(F)cccc2F)nc1C(=O)Nc1cnccc1N1C[C@@H](N)C[C@@H](F)C1] | 5-amino-N-(4-((3S,5R)-3-amino-5-fluoropiperidin-1-yl)pyridin-3-yl)-2-(2,6-difluorophenyl)thiazole-4-carboxamide |
| 64 | 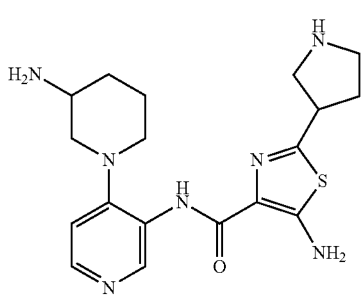 [SMILES: Nc1sc(C2CCNC2)nc1C(=O)Nc1cnccc1N1CCCC(N)C1] | 5-amino-N-(4-(3-aminopiperidin-1-yl)pyridin-3-yl)-2-(pyrrolidin-3-yl)thiazole-4-carboxamide |

TABLE 1-continued

| Ex. | Structure | Name |
|---|---|---|
| 65 | 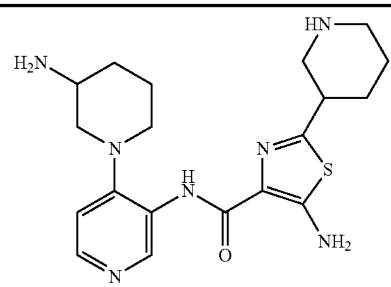 | 5-amino-N-(4-(3-aminopiperidin-1-yl)pyridin-3-yl)-2-(piperidin-3-yl)thiazole-4-carboxamide |
| 66 | 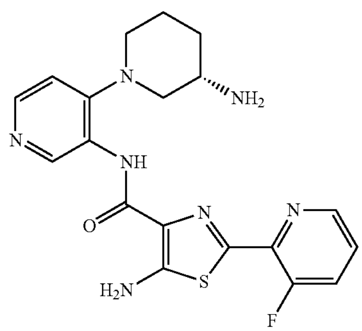 [SMILES: Nc1sc(-c2ncccc2F)nc1C(=O)Nc1cnccc1N1CCC[C@H](N)C1] | (S)-5-amino-N-(4-(3-aminopiperidin-1-yl)pyridin-3-yl)-2-(3-fluoropyridin-2-yl)thiazole-4-carboxamide |

The present invention includes a composition (for example, a pharmaceutical composition) comprising a compound of formula (I), (II), (III), (IV), and/or (V) (and/or solvates, hydrates and/or salts thereof) and a carrier (a pharmaceutically acceptable carrier). The present invention also includes a composition (for example, a pharmaceutical composition) comprising a compound of formula (I), (II), (III), (IV), and/or (V) (and/or solvates, hydrates and/or salts thereof) and a carrier (a pharmaceutically acceptable carrier), further comprising a second chemotherapeutic agent such as those described herein. The present compositions are useful for inhibiting abnormal cell growth or treating a hyperproliferative disorder such as cancer in a mammal (for example, human). For example, the present compounds and compositions are useful for treating multiple myeloma, lymphoma, acute myeloid leukemia, prostate cancer, breast cancer, hepatocellular carcinoma, pancreatic cancer, and/or colorectal cancer in a mammal (for example, human).

The present invention includes a method of inhibiting abnormal cell growth or treating a hyperproliferative disorder such as cancer in a mammal (for example, human) comprising administering to said mammal a therapeutically effective amount of a compound of formula (I), (II), (III), (IV), and/or (V) (and/or solvates, hydrates and/or salts thereof) or a composition thereof. For example, the present invention includes a method of treating multiple myeloma, lymphoma, acute myeloid leukemia, prostate cancer, breast cancer, hepatocellular carcinoma, pancreatic cancer, and/or colorectal cancer in a mammal (for example, human), comprising administering to said mammal a therapeutically effective amount of a compound of formula (I), (II), (III), (IV), and/or (V) (and/or solvates, hydrates and/or salts thereof) or a composition thereof.

The present invention includes a method of inhibiting abnormal cell growth or treating a hyperproliferative disorder such as cancer in a mammal (for example, human) comprising administering to said mammal a therapeutically effective amount of a compound of formula (I), (II), (III), (IV), and/or (V) (and/or solvates, hydrates and/or salts thereof) or a composition thereof, in combination with a second chemotherapeutic agent such as those described herein. For example, the present invention includes a method of treating multiple myeloma, lymphoma, acute myeloid leukemia, prostate cancer, breast cancer, hepatocellular carcinoma, pancreatic cancer, and/or colorectal cancer in a mammal (for example, human), comprising administering to said mammal a therapeutically effective amount of a compound of formula (I), (II), (III), (IV), and/or (V) (and/or solvates, hydrates and/or salts thereof) or a composition thereof, in combination with a second chemotherapeutic agent such as those described herein.

The present invention includes a method of treating lymphoma in a mammal (for example, human) comprising administering to said mammal a therapeutically effective amount of a compound of formula (I), (II), (III), (IV), and/or (V) (and/or solvates, hydrates and/or salts thereof) or a composition thereof, either alone or in combination with a second chemotherapeutic agent such as an anti-B-cell antibody therapeutic (for example, Rituxan and/or Dacetuzumab), gemcitabine, corticosteroids (for example, prednisolone and/or dexamethasone), chemotherapy cocktails (for example, CHOP (cyclophosphamide, doxorubicin, vincristine, prednisolone) and/or ICE (isfosfamide, cytoxan, etoposide)), a combination of biologics and chemotherapy (for example, Rituxan-ICE, Dacetuzumab-Rituxan-ICE, R-Gem, and/or D-R-Gem), an Aid inhibitor, a PI3K inhibitor, rapamycin, a MEK inhibitor (for example GDC-0973), a Bcl-2 inhibitor (for example ABT-263), and lymphoma directed antibody drug conjugate (for example, antiCD22 antibody drug conjugate including but not limited to antiCD22-vcMMAE, and/or antiCD79b-antibody drug conjugate including but not limited to antiCD79b-vcMMAE).

Formula I compounds may be employed in combination with certain chemotherapeutic agents for the treatment of a hematopoietic malignancy, along with pre-malignant and non-neoplastic or non-malignant hyperproliferative disorders. In certain embodiments, a compound of Formula I is combined in a pharmaceutical combination formulation, or dosing regimen as combination therapy, with a chemotherapeutic agent that has anti-hyperproliferative properties or that is useful for treating the hematopoietic malignancy. The chemotherapeutic agent of the pharmaceutical combination formulation or dosing regimen preferably has complementary activities to the formula I compound, and such that they do not adversely affect each other. Such compounds of the therapeutic combination may be administered in amounts that are effective for the purpose intended. In one embodiment, a pharmaceutical formulation of this invention comprises a formula I compound and a chemotherapeutic agent such as described herein, in a combined formulation. In another embodiment, the therapeutic combination is administered by a dosing regimen wherein the therapeutically effective amount of a formula I compound is administered in a range from twice daily to once every three weeks (q3wk), and the therapeutically effective amount of the chemotherapeutic agent is administered separately, in alternation, in a range from twice daily to once every three weeks.

The present invention includes a method of treating multiple myeloma in a mammal (for example, human) comprising administering to said mammal a therapeutically effective amount of a compound of formula (I), (II), (III), (IV), and/or (V) (and/or solvates, hydrates and/or salts thereof) or a composition thereof, either alone or in combination with a second chemotherapeutic agent such as melphalan, "Imids" (for example, thalidomide, lenalidomide, and/or pomolidamide), corticosteroids (for example, dexamethasone and/or prednisolone), and bortezomib or other proteosome inhibitor.

The present invention includes a method of treating acute myeloid leukemia (AML) in a mammal (for example, human) comprising administering to said mammal a therapeutically effective amount of a compound of formula (I), (II), (III), (IV), and/or (V) (and/or solvates, hydrates and/or salts thereof) or a composition thereof, either alone or in combination with a second chemotherapeutic agent such as cytarabine (araC), anthracylines (for example, daunorubicin and/or idarubicin), anti-myeloid antibody therapeutics (for example, SGN-33), anti-myeloid antibody-drug conjugates (for example, mylotarg).

The present invention includes a method of treating chronic lymphocytic leukemia (CLL) in a mammal (for example, human) comprising administering to said mammal a therapeutically effective amount of a compound of formula (I), (II), (III), (IV), and/or (V) (and/or solvates, hydrates and/or salts thereof) or a composition thereof, either alone or in combination with a second chemotherapeutic agent such as fludarabine, cyclophosphamide, anti-B-cell antibody therapeutics (for example, Rituxan and/or Dacetuzumab).

The present invention includes a method of treating chronic myeloid leukemia (CML) in a mammal (for example, human) comprising administering to said mammal a therapeutically effective amount of a compound of formula (I), (II), (III), (IV), and/or (V) (and/or solvates, hydrates and/or salts thereof) or a composition thereof, either alone or in combination with a second chemotherapeutic agent such as a BCR-abl inhibitor (for example, imatinib, nilotinib, and/or dasatinib).

The present invention includes a method of treating myelodysplastic diseases (MDS) and myeloproliferative disorders including polycythemia vera (PV), essential thrombocytosis (ET) or myelofibrosis (MF), in a mammal (for example, human) comprising administering to said mammal a therapeutically effective amount of a compound of formula (I), (II), (III), (IV), and/or (V) (and/or solvates, hydrates and/or salts thereof) or a composition thereof, either alone or in combination.

The present invention includes a method of using the present compounds for in vitro, in situ, and in vivo diagnosis or treatment of mammalian cells, organisms, or associated pathological conditions.

Chemotherapeutic Agents

Certain chemotherapeutic agents have demonstrated surprising and unexpected properties in combination with formula I compounds of the invention in inhibiting cellular proliferation in vitro and in vivo. Such chemotherapeutic agents include: PI3K inhibitor, Formula A compound known as GDC-0941 (Genentech, Inc.) and named as 4-(2-(1H-indazol-4-yl)-6-((4-(methylsulfonyl)piperazin-1-yl)methyl)thieno[3,2-d]pyrimidin-4-yl)morpholine; registered as CAS Reg. No. 957054-30-7; described and claimed in US 2008/0076768; disclosed in Folkes et al (2008) Jour. of Med. Chem. 51(18):5522-5532; Belvin et al, American Association for Cancer Research Annual Meeting 2008, 99th: April 15, Abstract 4004; Folkes et al, American Association for Cancer Research Annual Meeting 2008, 99th: April 14, Abstract LB-146; Friedman et al, American Association for Cancer Research Annual Meeting 2008, 99th: April 14, Abstract LB-110; and has the structure:

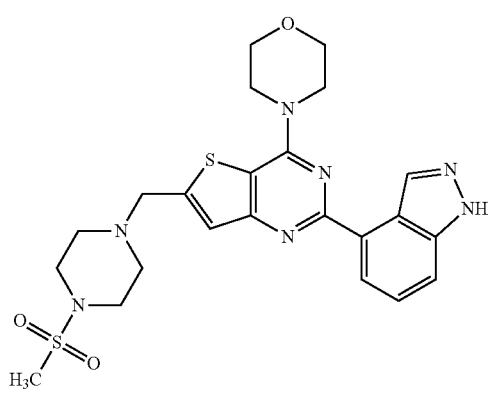

A

Another exemplary PI3K inhibitor chemotherapeutic agent is Formula B compound, named as (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one; (US 2008/02426651; and has structure B:

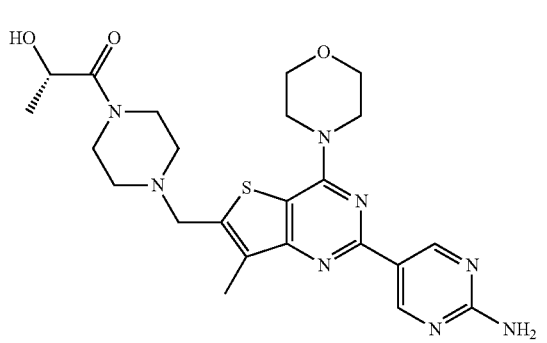

B

Biological Evaluation

Certain exemplary therapeutic combinations of formula I compounds and chemotherapeutic agents described herein were assayed for in vitro activity against tumor cells, and in vivo activity against tumors in mice.

In Vitro Cell Proliferation Assays

The cytotoxic or cytostatic activity of formula I exemplary compounds was measured by: establishing a proliferating mammalian tumor cell line in a cell culture medium, adding a formula I compound, culturing the cells for a period from about 6 hours to about 5 days; and measuring cell viability (Example i). Cell-based in vitro assays were used to measure viability, i.e. proliferation ($IC_{50}$), cytotoxicity ($EC_{50}$), and induction of apoptosis (caspase activation).

The in vitro potency of the combinations of formula I compounds with chemotherapeutic agents was measured by the cell proliferation assay of Example 11 and the results are compiled in Example iii. The CellTiter-Glo® Luminescent Cell Viability Assay (commercially available from Promega Corp., Madison, Wis.) is a homogeneous assay method based on the recombinant expression of Coleoptera luciferase (U.S. Pat. No. 5,583,024; U.S. Pat. No. 5,674,713; U.S. Pat. No. 5,700,670) and determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 or 384 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, for example 96 or 384 well format. Data can be recorded by luminometer or CCD camera imaging device. The luminescence output is presented as relative light units (RLU), measured over time.

The anti-proliferative effects of formula I exemplary compounds and combinations with chemotherapeutic agents were measured by the CellTiter-Glo® Assay (Example ii) against the tumor cell lines in Example iii. $EC_{50}$ values were established for the tested compounds and combinations. The range of in vitro cell potency activities was about 0.1 nM to about 3 μM.

Figure 2:
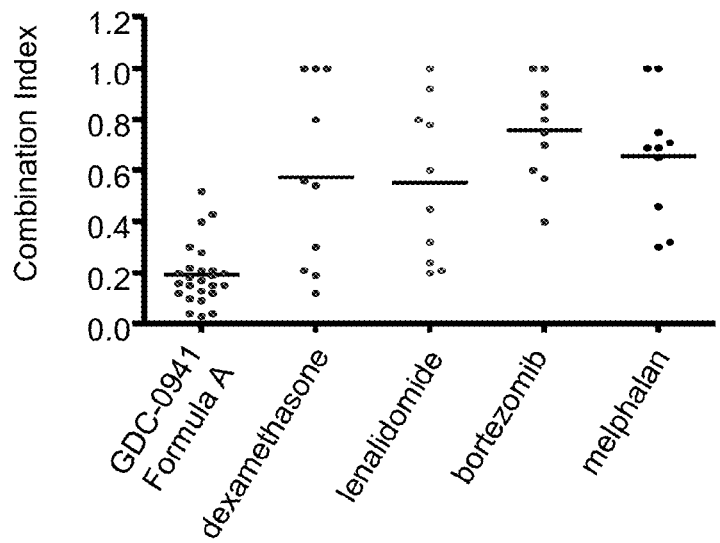
FIG. 2 shows a plot of Combination Index values from in vitro cell proliferation assays comparing combinations of (S)-5-amino-N-(4-(3-aminopiperidin-1-yl)pyridin-3-yl)-2-(2,6-difluorophenyl)thiazole-4-carboxamide (Compound 3, Example 3) and chemotherapeutic agents GDC-0941, dexamethasone, lenalidomide, bortezomib, and melphalan.

The individual measured EC50 values of exemplary Compound 3 ((S)-5-amino-N-(4-(3-aminopiperidin-1-yl)pyridin-3-yl)-2-(2,6-difluorophenyl)thiazole-4-carboxamide) and of the chemotherapeutic agent against the particular cell were compared to the combination EC50 value. The combination index (CI) score is calculated by the Chou and Talalay method (Chou, T. and Talalay, P. (1984) Adv. Enzyme Regul. 22:27-55). A CI less than 0.8 indicates synergy. A CI between 0.8 and 1.2 indicates additivity. A CI greater than 1.2 indicates antagonism. The strength of synergy is assessed according to Chou and Talalay. Certain therapeutic combinations in FIGS. 1 and 2 show the surprising and unexpected property of synergy in the in vitro cell proliferation assays with tumor type cell lines including multiple myeloma. Other combinations show no synergy; and only show mere additivity or antagonism. Certain combinations are synergistic with one or more tumor types, but not others. The synergy demonstrated in the in vitro cell proliferation assays provides a basis to expect a corresponding synergy in treating hematopoietic cancers including, but not limited to, multiple myeloma in human patients.

FIG. 1 shows the effect of Pim single agent inhibitor, (S)-5-amino-N-(4-(3-aminopiperidin-1-yl)pyridin-3-yl)-2-(2,6-difluorophenyl)thiazole-4-carboxamide (Compound 3, Example 3), and in combinations with GDC-0941 Formula A and Formula B on multiple myeloma cell line MM.1S in a 3 day proliferation assay. The in vitro cell survival and proliferation assay (Cell-Titer Glo, Promega) measured viable cells over varying inhibitor concentrations ($10^{-3}$ to 10 μMolar, Relative Units, wherein a Relative Unit equals 0.3 micromolar for Compound 3, 0.3 micromolar for Formula A, and 0.1 micromolar for Formula B).

TABLE 2

| Combination | [drug] @ 1 relative unit, μM | CI at: ED50 | CI at: ED75 | CI at: ED90 |
|---|---|---|---|---|
| Compound 3 + Formula A (GDC-0941) | 0.3 + 0.3 | 0.21 | 0.21 | 0.30 |
| Compound 3 + Formula B | 0.3 + 0.1 | 0.24 | 0.25 | 0.35 |

Sigmoid dose-response curves are obtained, indicative of well-behaved, soluble compounds and appropriate assay conditions. The curve obtained for Compound 3 single agent does not fully reach 0% of the control value suggesting a partial or fully cytostatic mode of action, whereas Formula A and Formula B both reach about 0% of control values suggesting a cytotoxic modality. In test conditions where either Formula A or Formula B appear in combination with Compound 3, the dose-response curves are shifted to the left indicating that these combinations have a more potent effect than each single agent alone. Such combination dose-response curves reach to about 0% of control, suggesting that the cytotoxic modality of Formula A and Formula B are retained in the respective combinations. Mathematical treatment of the data in FIG. 1 according to the methods of Chao and Talalay provides the data in Table 2. Provided in the last three columns of Table 2 are the Combination Index (CI values), calculated at the Effective Dose (ED) 50, 75, and 90, respectively. Consistent with the full leftward shift in the combinations of all measured points in the single agent curves of Formula A and Formula B, the calculated CI values are substantially less than 1 at the ED50, ED75, and ED90. These CI values indicate that the combinations tested have an surprising and unexpected synergistic effect to promote cancer cell death in the assay.

FIG. 2 shows a plot of Combination Index values from in vitro cell proliferation assays comparing combinations of (S)-5-amino-N-(4-(3-aminopiperidin-1-yl)pyridin-3-yl)-2-(2,6-difluorophenyl)thiazole-4-carboxamide (Compound 3, Example 3) and chemotherapeutic agents GDC-0941, dexamethasone, lenalidomide, bortezomib, and melphalan.

Shown in FIG. 2 are a summary of Combination Index values for Compound 3 in combination with different agents. The values shown were calculated at the ED50 of the dose response curves which were similar in nature to those exemplified in FIG. 1. Each dot in the plot represents the test results obtained with a different multiple myeloma cell line with a different combination of test agents, including Compound 3 plus a second agent as labeled on the abscissa. The horizontal line on the plot itself indicates the mean of all CI values for a given test agent. Combinations of Compound 3 with clinical standard of care chemotherapeutic agents including dexamethasone, lenalidomide, bortezomib, and melphalan produced variable results wherein CI values between about 0.1 and about 1 were obtained, with means generally greater than about 0.5. Compared to these clinically active agents, unexpectedly uniform and unexpectedly potent combination test results were obtained for Compound 3 in combination with Formula A, in which the majority of calculated CI values were less than about 0.2 and the mean across all cancer cell lines tested was about 0.2. In addition to these findings, bone marrow aspirate samples from multiple myeloma patients were and to test Formula A and Compound 3 singly and in combination on these primary cancer cell isolates. Two of four cases showed only limited single agent activity at either 0.3 or 1.0 micromolar drug concentrations, but that the combination treatment induced extensive apoptosis in tumor cells but not in unrelated B-cell lineage cells.

Dexamethasone is a potent glucocorticoid steroid hormone, with anti-inflammatory and immunosuppressant activity. In oncology, dexamethasone is given to cancer patients undergoing chemotherapy, both to counteract certain side-effects of their antitumor treatment as well as for its direct antitumor activity. Dexamethasone is named as (8S,9R,10S, 11S,13S,14S,16R,17R)-9-fluoro-11,17-dihydroxy-17-(2-hydroxyacetyl)-10,13,16-trimethyl-6,7,8,11,12,14,15,16-octahydrocyclopenta[a]phenanthren-3-one (CAS Reg. No. 50-02-2).

Lenalidomide (REVLIMID®, CC5013, Revimid, Celgene Inc.) is a derivative of thalidomide and introduced in 2004 (U.S. Pat. No. 5,635,517, U.S. Pat. No. 6,281,230) to treat both inflammatory disorders and cancers. There are multiple mechanisms of action, including a direct anti-tumor effect, inhibition of the microenvironment support for tumor cells, and an immunomodulatory role. In vitro, lenalidomide induces tumor cell apoptosis directly and indirectly by inhibition of bone marrow stromal cell support, by anti-angiogenic and anti-osteoclastogenic effects, and by immunomodulatory activity. Lenalidomide was initially intended as a treatment for multiple myeloma, for which thalidomide is an accepted therapeutic modality, but has also shown efficacy in the class of hematological disorders known as myelodysplastic syndromes (Richardson et al (2002) Blood 100:3063; Bartlett et al (2004) Nature Rev. 4:314-322; Mitsiades et al (2004) Curr. Opin. Invest. Drugs 5:635-647; Armoiry et al. (2008) J of Clin Pharmacy & Therapeutics 33:219-226; List et al (2005) N. Engl. Jour. Med. 352:549-57). Lenalidomide is named as 3-(4-amino-1-oxoisoindolin-2-yl)piperidine-2,6-dione; 3-(4-amino-1,3-dihydro-1-oxo-2H-isoindol-2-yl)-2, 6-piperidinedione; 1-oxo-2-(2,6-dioxopiperidin-3-yl)-4-aminoisoindoline (CAS Reg. No. 191732-72-6).

Bortezomib (MG-341, PS-341, VELCADE®, Millenium Pharm.) is a boronic acid proteasome inhibitor approved in the US for treating relapsed multiple myeloma and mantle cell lymphoma. (WO 96/13266; U.S. Pat. No. 5,780,454; U.S. Pat. No. 6,083,903; U.S. Pat. No. 6,297,217; U.S. Pat. No. 6,617,317; U.S. Pat. No. 6,713,446; U.S. Pat. No. 6,747, 150; U.S. Pat. No. 6,958,319; U.S. Pat. No. 7,119,080). The boron atom in bortezomib binds the catalytic site of the 26S proteasome with high affinity and specificity. In normal cells, the proteasome regulates protein expression and function by degradation of ubiquitinylated proteins, and also cleanses the cell of abnormal or misfolded proteins. (Adams et al (2004) Cancer Invest 22(2):304-11; Bonvini (2007). Leukemia 21(4):838-42). Bortezomib is named as [(1R)-3-methyl-1-({ (2S)-3-phenyl-2-[(pyrazin-2-ylcarbonyl)amino] propanoyl}amino)butyl]boronic acid; (R)-3-methyl-1-((S)-3-phenyl-2-(pyrazine-2-carboxamido)propanamido) butylboronic acid; or [(1R)-3-methyl-1-[[(2S)-1-oxo-3-phenyl-2-[(pyrazinylcarbonyl)amino]propyl]amino]butyl]-boronic acid (CAS Reg. No. 179324-69-7).

Melphalan (L-phenylalanine mustard; alanine nitrogen mustard; L-PAM; melfalan; L-sarcolysine; NSC-8806; CB-3025; ALKERAN® (Glaxo SmithKline); Sarcoclorin) is a nitrogen mustard alkylating agent type of chemotherapeutic (U.S. Pat. No. 3,032,584; U.S. Pat. No. 3,032,585). Melphalan is used primarily to treat multiple myeloma, ovarian cancer and melanoma (IARC Monographs (1975) 9:167-180; Furner et al (1980) Cancer Treat. Rep. 64:559-574). Melphalan is named as 2-amino-3-[4-[bis(2-chloroethyl)amino] phenyl]-propanoic acid; 4-[bis(2-chloroethyl)amino]-L-phenylalanine; or p-di(2-chloroethyl)amino-L-phenylalanine (CAS Reg. No. 148-82-3).

Figure 3:
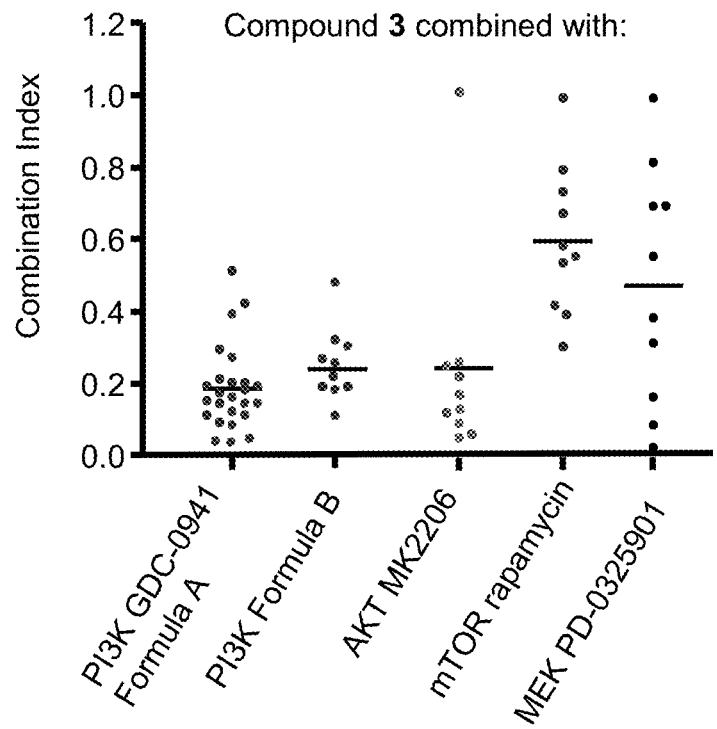
FIG. 3 shows a plot of Combination Index values from in vitro multiple myeloma cell line proliferation assays comparing combinations of (S)-5-amino-N-(4-(3-aminopiperidin-1-yl)pyridin-3-yl)-2-(2,6-difluorophenyl)thiazole-4-carboxamide (Compound 3, Example 3) and chemotherapeutic agents GDC-0941, Formula B, AKT inhibitor MK2206, TORC1 inhibitor rapamycin, and MEK inhibitor PD-0325901. The values shown were calculated at the ED50 of the dose response curves which were similar in nature to those exemplified in FIG. 1. Each dot in the plot represents the test results obtained with a different multiple myeloma cell line with a different combination of test agents, including Compound 3 plus a second chemotherapeutic agent as labeled on the abscissa. The horizontal line on the plot itself indicates the mean of all CI values for a given combination of test agents.

FIG. 3 shows a plot of Combination Index values from in vitro multiple myeloma cell line proliferation assays comparing combinations of (S)-5-amino-N-(4-(3-aminopiperidin-1-yl)pyridin-3-yl)-2-(2,6-difluorophenyl)thiazole-4-carboxamide (Compound 3, Example 3) and chemotherapeutic agents PI3K inhibitor GDC-0941, PI3K inhibitor Formula B, AKT inhibitor MK2206, TORC1 inhibitor rapamycin, and MEK inhibitor PD-0325901. The values shown were calculated at the ED50 of the dose response curves which were similar in nature to those exemplified in FIG. 1. Each dot in the plot represents the test results obtained with a different multiple myeloma cell line with a different combination of test agents, including Compound 3 plus a second agent as labeled on the abscissa. The horizontal line on the plot itself indicates the mean of all CI values for a given combination of test agents. Combination of Compound 3 with the MEK inhibitor PD-0325901 produced variable results wherein CI values between about 0 and about 1 were obtained, with a mean of about 0.5. Combination of Compound 3 with rapamycin produced weaker but more homogenous results, whereas combination with AKT or PI3K inhibitors resulted in uniformly strong synergy to inhibit myeloma cell survival. These results indicate that Pim inhibition is not broadly synergistic with other chemotherapeutic agents and only those agents that inhibit the AKT/PI3K pathway have strong and uniform combination activity with a Pim Kinase inhibitor.

MK2206 (Merck & Co.) is an AKT inhibitor being developed for potential treatment of solid tumors by oral administration (Yan, L. $100^{th}$ Amer. Assoc. for Cancer Res., April 2009, Abstract DDT01-1; Trucksis, M. et al, $100^{th}$ Amer. Assoc. for Cancer Res., April 2009, Abstract 3604; Hirai, H. et al, $100^{th}$ Amer. Assoc. for Cancer Res., April 2009, Abstract 3707; Morphy, R. (2010) J. Med. Chem. 53(4):1413-1437; U.S. Pat. No. 7,576,209). MK2206 is named as 8-(4-(1-aminocyclobutyl)phenyl)-9-phenyl-[1,2,4]triazolo[3,4-f] [1,6]naphthyridin-3(2H)-one and has the structure:

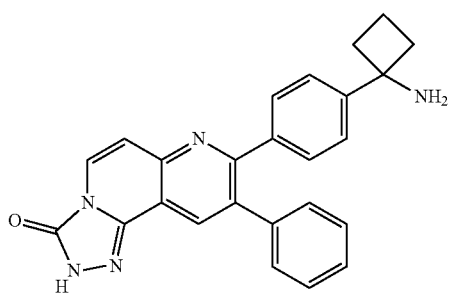

Rapamycin (sirolimus, RAPAMUNE®) is an immunosuppressant drug used to prevent rejection in organ transplantation, and is especially useful in kidney transplants. Rapamycin is a macrolide antibiotic produced by the bacterium *Streptomyces hygroscopicus* in a soil sample obtained from an island called Rapa Nui, better known as Easter Island (Pritchard DI (2005). Drug Discovery Today 10 (10): 688-691). Rapamycin inhibits the response to interleukin-2 (IL-2) and thereby blocks activation of T- and hematopoietics. The mode of action of rapamycin is to bind the cytosolic protein FK-binding protein 12 (FKBP12). The rapamycin-FKBP12 complex inhibits the mammalian target of rapamycin (mTOR) pathway through directly binding the mTOR Complex1 (mTORC1). mTOR is also called FRAP (FKBP-rapamycin associated protein) or RAFT (rapamycin and FKBP target). Rapamycin analogs ("Rapalogs") include Temsirolimus (CCI-779, Wyeth), Everolimus (RAD001, Novartis), Deforolimus (AP23573, MK-8669, Ariad, Merck). Rapamycin is named as (3S,6R,7E,9R,10R,12R,14S,15E,17E,19E,21S,23S,26R,27R,34aS)-9,10,12,13,14,21,22,23,24,25,26,27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4]-oxaazacyclohentriacontine-1,5,11,28,29(4H,6H,31H)-pentone (CAS Reg. No. 53123-88-9), and has the structure:

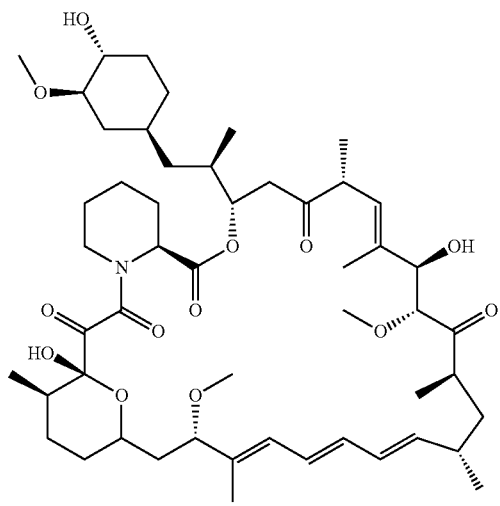 [SMILES: CO[C@H]1CC2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

PD-0325901 (CAS RN 391210-10-9, Pfizer) is a second-generation, non-ATP competitive, allosteric MEK inhibitor for the potential oral tablet treatment of cancer (U.S. Pat. No. 6,960,614; U.S. Pat. No. 6,972,298; US 2004/147478; US 2005/085550). Phase II clinical trials have been conducted for the potential treatment of breast tumors, colon tumors, and melanoma. PD-0325901 is named as (R)-N-(2,3-dihydroxypropoxy)-3,4-difluoro-2-(2-fluoro-4-iodophenylamino)benzamide, and has the structure:

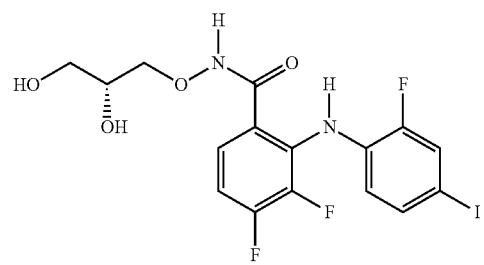 [SMILES: O=C(NOC[C@H](O)CO)c1ccc(F)c(F)c1Nc1ccc(I)cc1F]

Figure 4:
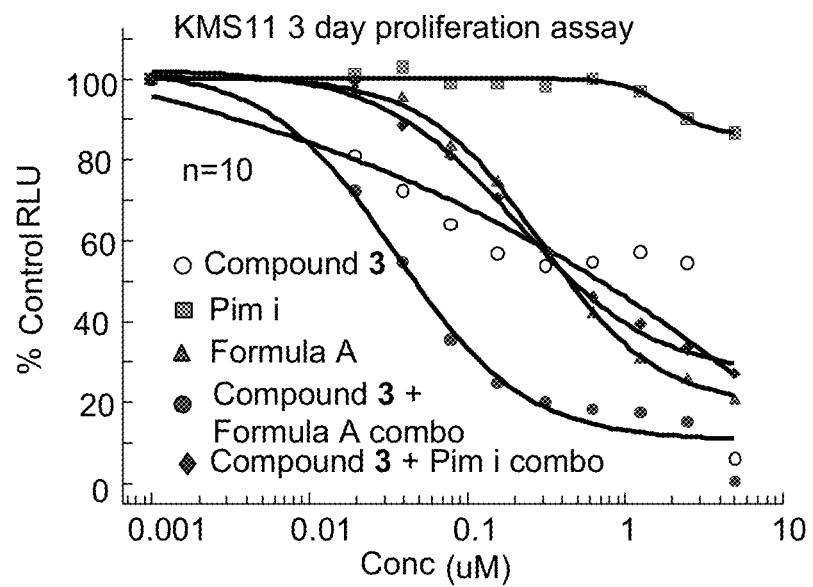
FIG. 4 shows dose-response curves as a percentage of vehicle control values as a function of test agent concentrations for the multiple myeloma cell line KMS11. The results obtained here are representative of a total of ten multiple myeloma cell lines tested. This Cell Titer Glo proliferation and survival assay compares single agent (S)-5-amino-N-(4-(3-aminopiperidin-1-yl)pyridin-3-yl)-2-(2,6-difluorophenyl)thiazole-4-carboxamide (Compound 3, Example 3), PIMi, PI3K inhibitor GDC-0941 Formula A, and combinations thereof.

FIG. 4 shows dose-response curves as a percentage of vehicle control values as a function of test agent concentrations for the multiple myeloma cell line KMS11. The results obtained here are representative of a total of ten multiple myeloma cell lines tested. This Cell Titer Glo proliferation and survival assay compares single agent (S)-5-amino-N-(4-(3-aminopiperidin-1-yl)pyridine-3-yl)-2-(2,6-difluorophenyl)thiazole-4-carboxamide (Compound 3, Example 3), Compound PIMi, Formula A, and combinations thereof. As shown in Table 3, Compound PIMi is a selective inhibitor of Pim 1 and Pim 3 with 11-54 fold selectivity over Pim 2, whereas Compound 3 has a pan-Pim inhibition profile wherein potency against all three isoforms is more similar. Compound PIMi is named as 5-(phenethylamino)-N-(1H-pyrrolo[2,3-b]pyridine-3-yl)pyrazolo[1,5-a]pyrimidine-3-carboxamide (WO 2010/051549), and has the structure shown in Table 3. Interestingly, Compound PIMi had little activity toward the myeloma cell lines and an IC50 value was not obtained at doses up to 5 micromolar. In contrast, Compound 3, the pan-Pim inhibitor had relatively potent activity against all tested myeloma cell lines with a relative IC50 value of about 0.1-0.5 micromolar. Strikingly, when tested in combination with Formula A, only the pan-Pim inhibitor (Compound 3) had strong synergy wherein IC50 values of about 40-100 nM were obtained. This unexpected result indicates that Pim-2 inhibition is essential to obtain growth inhibition of multiple myeloma cell lines as either a single agent or in combination with PI3K inhibition.

TABLE 3

| Assay | PIMi | Compound 3 |
|---|---|---|
| Pim 1/2/3 Ki (μM) | 39/2090/187 | 11/47/19 |
| BaF3 parental (μM) | 12 | 8 |
| BaF3-Pim1 (μM) | 0.4 | 0.01 |
| BaF3-Pim2 (μM) | >20 | 2 |
| MM1.s (μM) | >20 | 0.2 |
| EOL-1 (μM) | 0.4 | 0.01 |

Figure 5:
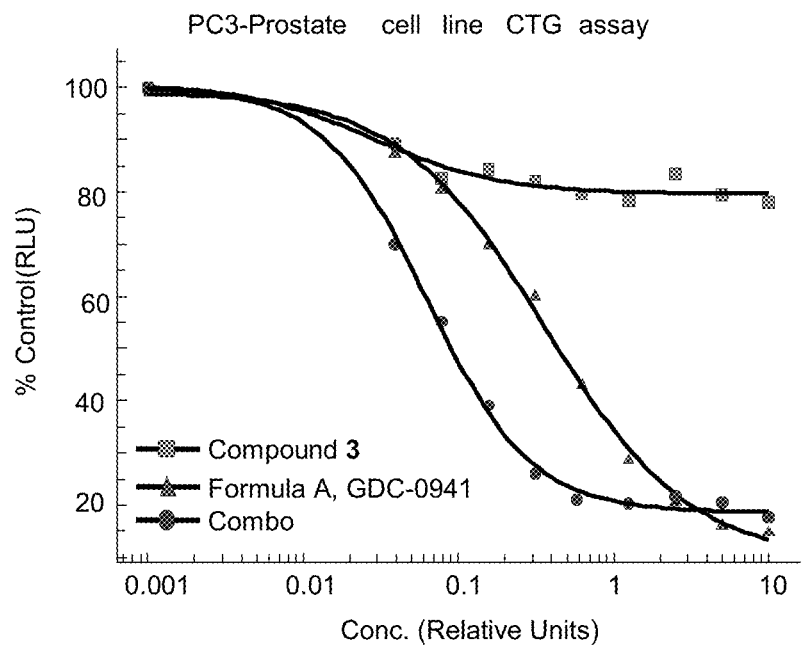
FIG. 5 shows dose-response curves as a percentage of vehicle control values as a function of test agent concentrations in "relative units" for the prostate cancer cell line PC3. The results obtained here are representative of a subset of prostate cell lines tested. This Cell Titer Glo proliferation and survival assay compares single agent (S)-5-amino-N-(4-(3-aminopiperidin-1-yl)pyridin-3-yl)-2-(2,6-difluorophenyl)thiazole-4-carboxamide (Compound 3, Example 3), Formula A, and the combination thereof.

FIG. 5 shows dose-response curves as a percentage of vehicle control values as a function of test agent concentrations in "relative units" for the prostate cancer cell line PC3. The results obtained here are representative of a subset of prostate cell lines tested. This Cell Titer Glo proliferation and survival assay compares single agent (S)-5-amino-N-(4-(3-aminopiperidin-1-yl)pyridine-3-yl)-2-(2,6-difluorophenyl)thiazole-4-carboxamide (Compound 3, Example 3), Formula A, and the combination thereof. Surprisingly, Compound 3 exhibited little activity in this assay, in contrast to literature reports of unrelated Pim inhibitors (Beharry et al, (2009) Molecular Cancer Therapeutics vol. 8 (6) pp. 1473-1483; Akue-Gedu et al. (2009) J. Med. Chem. vol. 52 (20) pp. 6369-6381; 011a et al. (2009) Bioorganic & Medicinal Chemistry Letters, pp. 5). This result suggests previous reports of PC3 cell growth reductions caused by Pim inhibition are erroneous results arising from non-selective effects of the test agents mis-reported as Pim-related activity. Formula A showed good activity as a single agent with a relative IC50 of about 300 nanomolar. The combination of Formula A with Compound 3 gave an unexpected synergistic result in which an IC50 of about 60 nanomolar, or a five-fold improvement in reduction of prostate cancer cell growth or survival. This surprising and unexpected result conflicts with prior disclosures by those skilled in the art and suggests that Pim inhibition may be of therapeutic utility in prostate cancer, but not for the reasons previously thought, and that combination therapy results with PI3K inhibition cannot be reliably predicted from single-agent Pim inhibition.

Figure 6:
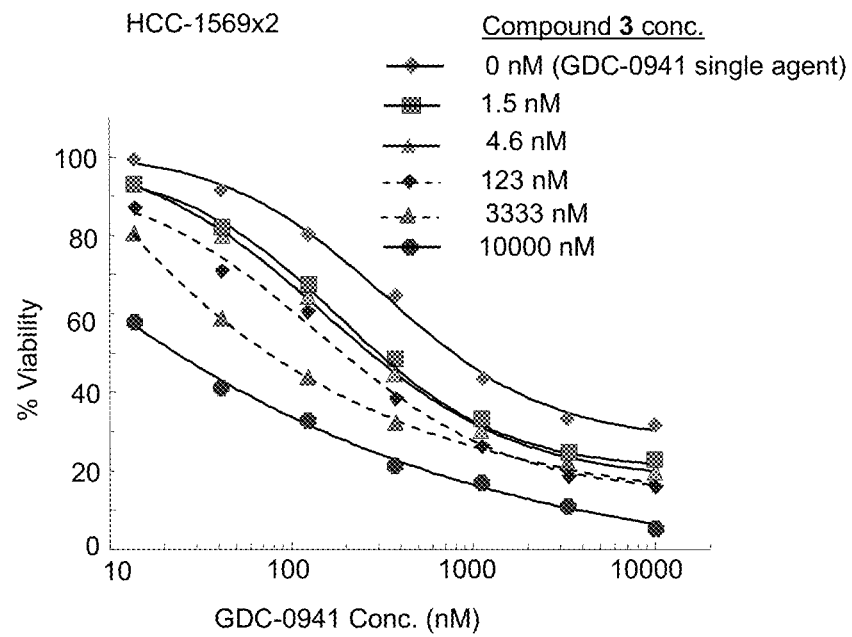
FIG. 6 shows dose-response curves as a percentage of vehicle control values as a function of test agent concentrations for the breast cancer cell line HCC-1569×2. The results obtained here are representative of a responsive subset of solid tumor cell lines listed in Table 4. This Cell Titer Glo proliferation and survival assay compares single agent Formula A to combinations of Formula A with increasing concentrations of (S)-5-amino-N-(4-(3-aminopiperidin-1-yl)pyridin-3-yl)-2-(2,6-difluorophenyl)thiazole-4-carboxamide (Compound 3, Example 3).

FIG. 6 shows dose-response curves as a percentage of vehicle control values as a function of test agent concentrations for the breast cancer cell line HCC-1569×2. The results obtained here are representative of a responsive subset of solid tumor cell lines listed in Table 4 as measured by Bliss independence/synergy (Bliss, C. I. (1956) Bacteriol. Rev. 20:243-258). Bliss independence/synergy is a method for calculating the expected dose-response relationship for combination therapy compared to monotherapy based on parameters such as IC50, the dose of drug needed to achieve 50% target inhibition and equal to Ki in the simplest case. This Cell Titer Glo proliferation and survival assay compares single agent Formula A to combinations of Formula A with increasing concentrations of (S)-5-amino-N-(4-(3-aminopiperidin-1-yl)pyridin-3-yl)-2-(2,6-difluorophenyl)thiazole-4-carboxamide (Compound 3, Example 3). The results indicate that the inclusion of even very low doses such as 1.5 nanomolar Compound 3 are sufficient to cause a 2-5 fold increase in the apparent potency of PI3K inhibitor GDC-0941 Formula A. These results indicate that Pim and PI3K combination inhibition may have therapeutic utility in a diverse set of cancer indications including breast, colon, pancreatic, and prostate cancer.

TABLE 4

Bliss Combo Analysis of solid tumor cell lines

| Solid Tumor Cell Line | Total | Responsive |
|---|---|---|
| breast | 20 | 8 (40%) |
| colon | 15 | 4 (27%) |
| lung | 20 | 0 (0%) |
| pancreatic | 8 | 1 (1.25%) |
| prostate | 6 | 4 (67%) |

In Vivo Tumor Xenograft Efficacy

The efficacy of the combinations of the invention may be measured in vivo by implanting allografts or xenografts of cancer cells in rodents and treating the tumor-bearing animals with the combinations. Variable results are to be expected depending on the cell line, the presence or absence of certain mutations in the tumor cells, the sequence of administration of a formula I compound and chemotherapeutic agent, dosing regimen, and other factors. Subject mice were treated with drug(s) or control (Vehicle) and monitored over several weeks or more to measure the time to tumor doubling, log cell kill, and tumor inhibition.

Figure 7:
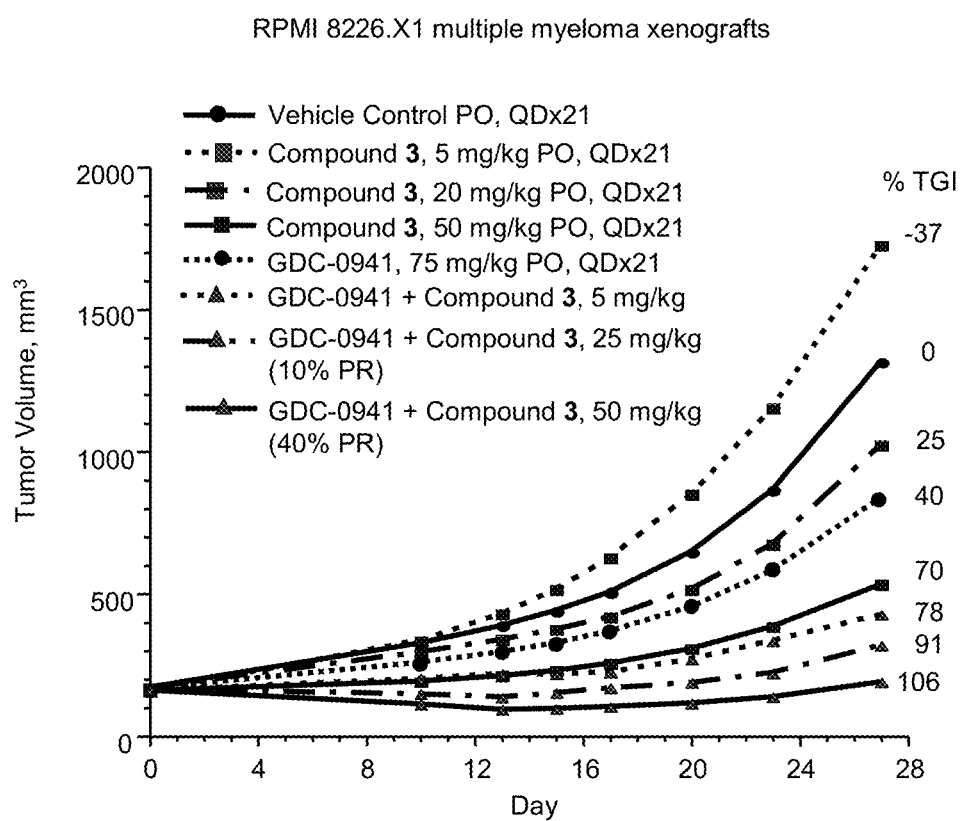
FIG. 7 shows the mean tumor volume change over 27 days in cohorts of SCID Beige mice with RPMI 8226.x1 multiple myeloma xenografts dosed daily for 21 days (po, qd x21) starting on day 0 with: Vehicle (0.5% Methylcellulose: 0.2% Tween 80 in DI Water); single agent therapies: 5, 20, and 50 mg/kg (S)-5-amino-N-(4-(3-aminopiperidin-1-yl)pyridin-3-yl)-2-(2,6-difluorophenyl)thiazole-4-carboxamide (Compound 3, Example 3), and 75 mg/kg GDC-0941 Formula A (po, qd x21); and the combinations of 5, 20, and 50 mg/kg (S)-5-amino-N-(4-(3-aminopiperidin-1-yl)pyridin-3-yl)-2-(2,6-difluorophenyl)thiazole-4-carboxamide (Compound 3, Example 3) and 75 mg/kg GDC-0941 Formula A (po, qd x21).

FIG. 7 shows the mean tumor volume change over 27 days in cohorts of SCID Beige mice with RPMI 8226.x1 multiple myeloma xenografts dosed daily for 21 days (po, qd x21) starting on day 0 with: Vehicle (0.5% Methylcellulose: 0.2% Tween 80 in DI Water); single agent therapies: 5, 20, and 50 mg/kg (S)-5-amino-N-(4-(3-aminopiperidin-1-yl)pyridine-3-yl)-2-(2,6-difluorophenyl)thiazole-4-carboxamide (Compound 3, Example 3), and 75 mg/kg GDC-0941 Formula A (po, qd x21); and the combinations of 5, 25, and 50 mg/kg (S)-5-amino-N-(4-(3-aminopiperidin-1-yl)pyridine-3-yl)-2-(2,6-difluorophenyl)thiazole-4-carboxamide (Compound 3, Example 3) and 75 mg/kg GDC-0941 Formula A (po, qd x21).

Dosing of all cohorts commenced on Day 0 when the mean tumor volume of all cohorts was between about 100 to 200 cubic millimeters. Compared to the vehicle control, doses of Compound 3 as a single agent had an effect to delay tumor growth, with increased delay at higher doses. At the lowest dose there was a trend toward accelerated tumor growth, though this trend was not statistically significant. At the highest dose of 50 mg/kg a tumor growth inhibition (TGI) of about 70% was obtained at day 27 compared to vehicle. Formula A was tested at as a single agent at a single dose level of 75 mg/kg for which a lesser TGI of 40% was obtained at day 27. Combinations of Compound 3 with Formula A showed increasing levels of tumor growth suppression with increasing dose levels of Compound 3 and at the highest dose level tested, showed 106% TGI. These results suggest that the synergy of combination treatments that was observed in vitro can be recapitulated in vivo and, interpreted more broadly, that combinations of PIM kinase inhibitors (exemplified by Compound 3) combined with PI3K inhibitors (exemplified by Formula A) could provide therapeutic benefit to patients including but not limited to those with multiple myeloma.

Figure 8:
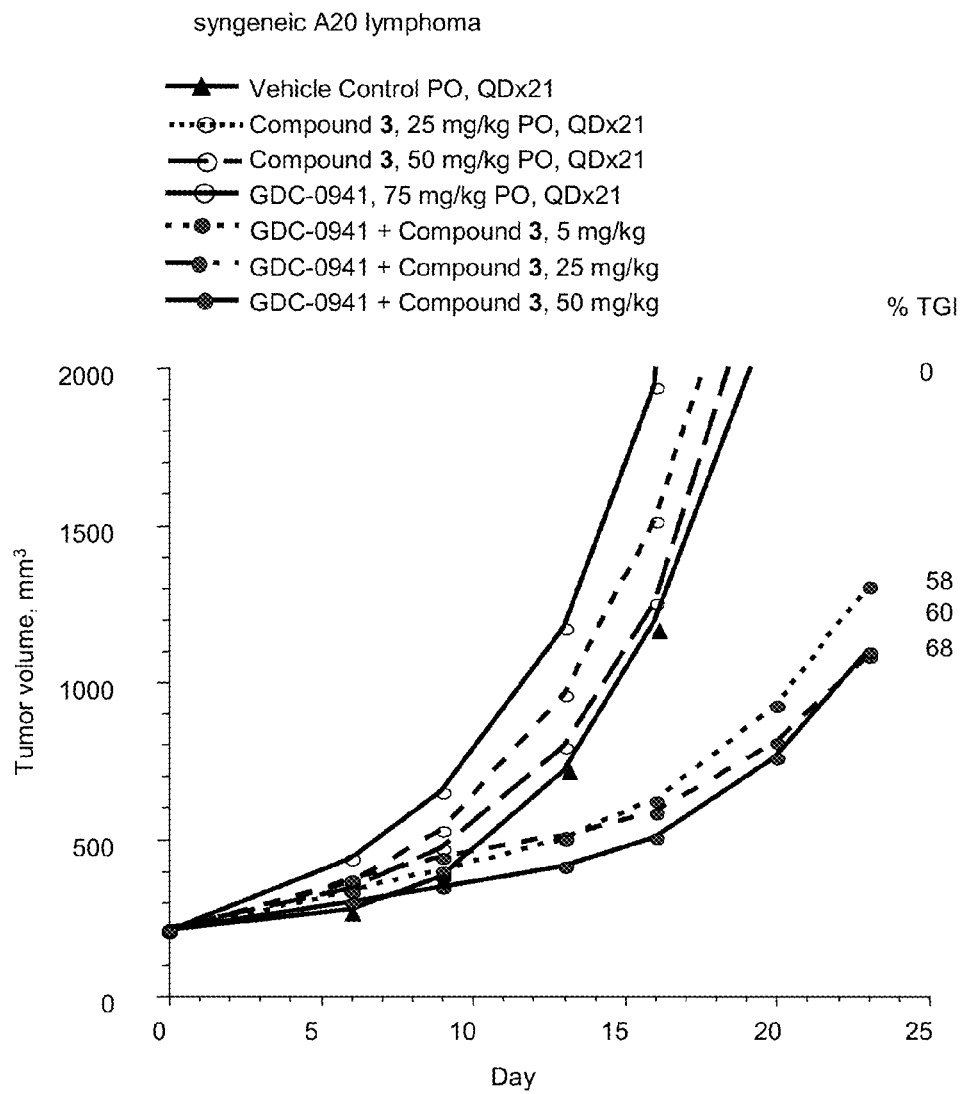
FIG. 8 shows the mean tumor volume change over 23 days in cohorts of immunocompetent Balb/c mice with syngeneic A20 lymphoma tumors dosed daily for 21 days (po, qd x21) starting on day 0 with: Vehicle (0.5% Methylcellulose: 0.2% Tween 80 in DI Water); single agent therapies: 25 and 50 mg/kg (S)-5-amino-N-(4-(3-aminopiperidin-1-yl)pyridin-3-yl)-2-(2,6-difluorophenyl)thiazole-4-carboxamide (Compound 3, Example 3), and 75 mg/kg GDC-0941 Formula A; and the combinations of 5, 25, and 50 mg/kg (S)-5-amino-N-(4-(3-aminopiperidin-1-yl)pyridin-3-yl)-2-(2,6-difluorophenyl)thiazole-4-carboxamide (Compound 3, Example 3) and 75 mg/kg GDC-0941 Formula A.

FIG. 8 shows the mean tumor volume change over 23 days in cohorts of immunocompetent Balb/c mice with syngeneic A20 lymphoma tumors dosed daily for 21 days (po, qd x21) starting on day 0 with: Vehicle (0.5% Methylcellulose: 0.2% Tween 80 in DI Water); single agent therapies: 25 and 50 mg/kg (S)-5-amino-N-(4-(3-aminopiperidin-1-yl)pyridine-3-yl)-2-(2,6-difluorophenyl)thiazole-4-carboxamide (Compound 3, Example 3), and 75 mg/kg GDC-0941 Formula A; and the combinations of 5, 25, and 50 mg/kg (S)-5-amino-N-(4-(3-aminopiperidin-1-yl)pyridine-3-yl)-2-(2,6-difluorophenyl)thiazole-4-carboxamide (Compound 3, Example 3) and 75 mg/kg GDC-0941 Formula A.

Dosing of all cohorts commenced on Day 0 when the mean tumor volume of all cohorts was between about 200 cubic millimeters. Compared to the vehicle control, doses of Formula A or Compound 3 as single agents had no significant effect on tumor growth. However, combinations of Compound 3 at all dose levels with Formula A showed increased levels of tumor growth suppression with the highest dose level tested showing 68% TGI. These results suggest that the synergy of combination treatments that was observed in vitro can be recapitulated in vivo and, interpreted more broadly, that combinations of PIM kinase inhibitors (exemplified by Compound 3) combined with PI3K inhibitors (exemplified by Formula A) could provide therapeutic benefit to patients including but not limited to those with Non-hodgkin's Lymphoma. At the conclusion of this study, femurs were collected and histological analysis of the bone marrow was conducted, and peripheral blood was collected for determination of blood cell counts. The vehicle group was compared to high-dose Compound 3 group and the high-dose combination group. While the first two groups showed no significant findings, the high dose combination group had the surprising finding that there were only very minimal hypocellularity in the marrow, and only modest reductions of peripheral white cell counts in the blood. These results indicate an unexpectedly broad therapeutic index wherein combination of PI3K and Pim yridine n can inhibit cancer cell growth without significant untoward effect on normal blood and marrow cells.

Figure 9:
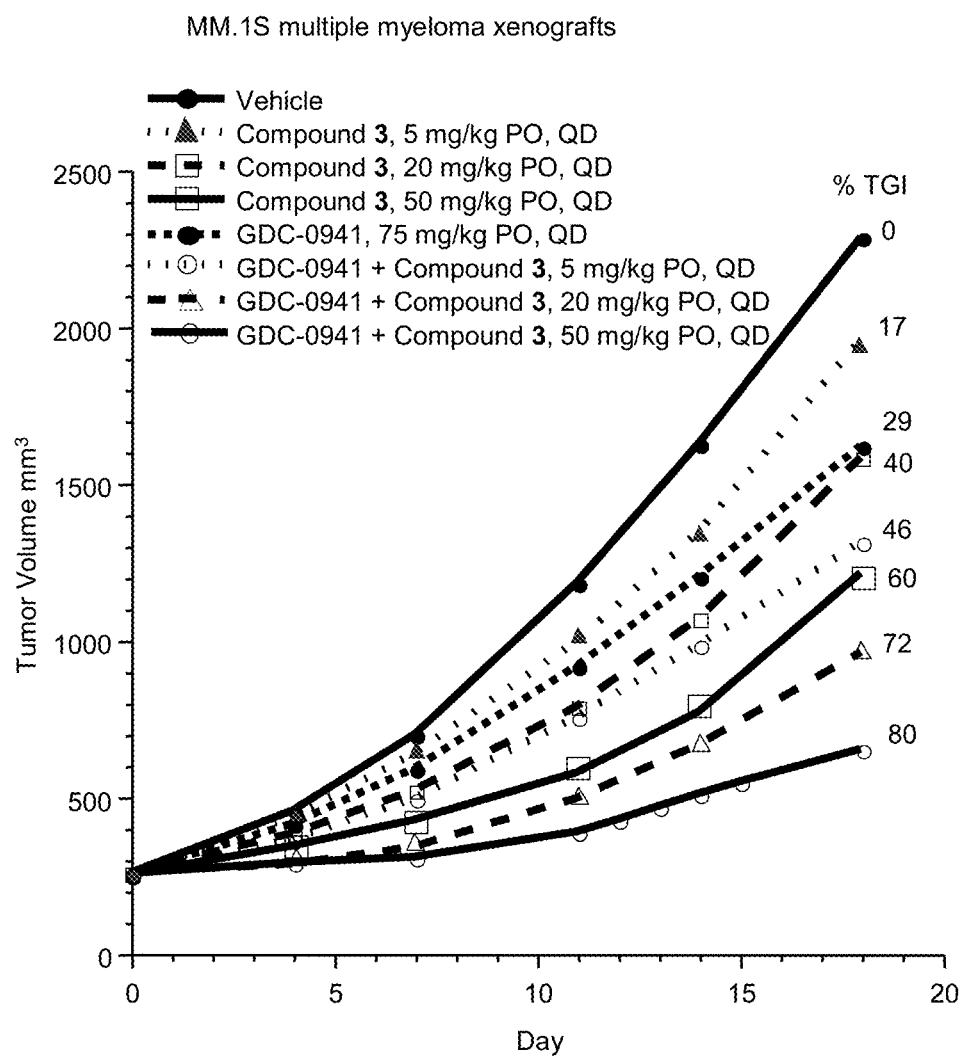
FIG. 9 shows the mean tumor volume change over 18 days in cohorts of SCID mice with MM1.s multiple myeloma xenografts dosed daily (po, qd) starting on day 0 with: Vehicle (0.5% Methylcellulose: 0.2% Tween 80 in DI Water); single agent therapies: 5, 20, and 50 mg/kg (S)-5-amino-N-(4-(3-aminopiperidin-1-yl)pyridin-3-yl)-2-(2,6-difluorophenyl)thiazole-4-carboxamide (Compound 3, Example 3), and 75 mg/kg GDC-0941 Formula A; and the combinations of 5, 20, and 50 mg/kg (S)-5-amino-N-(4-(3-aminopiperidin-1-yl)pyridin-3-yl)-2-(2,6-difluorophenyl)thiazole-4-carboxamide (Compound 3, Example 3) and 75 mg/kg GDC-0941 Formula A.

FIG. 9 shows the mean tumor volume change over 18 days in cohorts of SCID mice with MM1.s multiple myeloma xenografts dosed daily (po, qd) starting on day 0 with: Vehicle (0.5% Methylcellulose: 0.2% Tween 80 in DI Water); single agent therapies: 5, 20, and 50 mg/kg (S)-5-amino-N-(4-(3-aminopiperidin-1-yl)pyridine-3-yl)-2-(2,6-difluorophenyl)thiazole-4-carboxamide (Compound 3, Example 3), and 75 mg/kg GDC-0941 Formula A; and the combinations of 5, 20, and 50 mg/kg (S)-5-amino-N-(4-(3-aminopiperidin-1-yl)pyridine-3-yl)-2-(2,6-difluorophenyl)thiazole-4-carboxamide (Compound 3, Example 3) and 75 mg/kg GDC-0941 Formula A.

Dosing of all cohorts commenced on Day 0 when the mean tumor volume of all cohorts was between about 200 to 300 cubic millimeters. Compared to the vehicle control, doses of Compound 3 as a single agent had an effect to delay tumor growth, with increased delay at higher doses. At the highest dose of 50 mg/kg a tumor growth inhibition (TGI) of about 60% was obtained at day 18 compared to vehicle. Formula A was tested at as a single agent at a single dose level of 75 mg/kg for which a lesser TGI was obtained at day 18. Combinations of Compound 3 with Formula A showed increasing levels of tumor growth suppression with increasing dose levels of Compound 3 and at the highest dose level tested, showed 80% TGI. These results suggest that the synergy of combination treatments that was observed in vitro can be recapitulated in vivo and, interpreted more broadly, that combinations of PIM kinase inhibitors (exemplified by Compound 3) combined with PI3K inhibitors (exemplified by Formula A) could provide therapeutic benefit to patients including but not limited to those with multiple myeloma.

Figure 10:
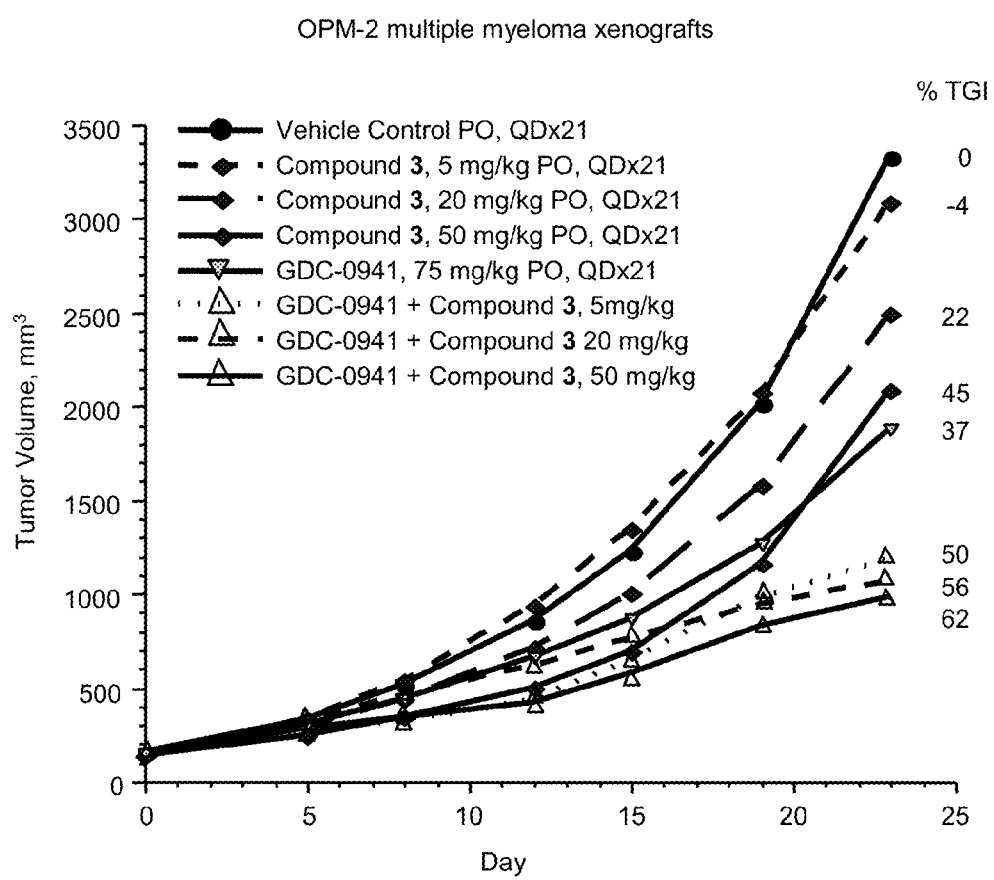
FIG. 10 shows the mean tumor volume change over 23 days in cohorts of SCID Beige mice with OPM-2 multiple myeloma xenografts dosed daily for 21 days (po, qd x21) starting on day 0 with: Vehicle (0.5% Methylcellulose: 0.2% Tween 80 in DI Water); single agent therapies: 5, 20, and 50 mg/kg (S)-5-amino-N-(4-(3-aminopiperidin-1-yl)pyridin-3-yl)-2-(2,6-difluorophenyl)thiazole-4-carboxamide (Compound 3, Example 3), and 75 mg/kg GDC-0941 Formula A (po, qd x21); and the combinations of 5, 20, and 50 mg/kg (S)-5-amino-N-(4-(3-aminopiperidin-1-yl)pyridin-3-yl)-2-(2,6-difluorophenyl)thiazole-4-carboxamide (Compound 3, Example 3) and 75 mg/kg GDC-0941 Formula A (po, qd x21).

FIG. 10 shows the mean tumor volume change over 23 days in cohorts of SCID Beige mice with OPM-2 multiple myeloma xenografts dosed daily for 21 days (po, qd x21) starting on day 0 with: Vehicle (0.5% Methylcellulose: 0.2% Tween 80 in DI Water); single agent therapies: 5, 20, and 50 mg/kg (S)-5-amino-N-(4-(3-aminopiperidin-1-yl)pyridine-3-yl)-2-(2,6-difluorophenyl)thiazole-4-carboxamide (Compound 3, Example 3), and 75 mg/kg GDC-0941 Formula A (po, qd x21); and the combinations of 5, 20, and 50 mg/kg (S)-5-amino-N-(4-(3-aminopiperidin-1-yl)pyridine-3-yl)-2-(2,6-difluorophenyl)thiazole-4-carboxamide (Compound 3, Example 3) and 75 mg/kg GDC-0941 Formula A (po, qd x21).

Dosing of all cohorts commenced on Day 0 when the mean tumor volume of all cohorts was between about 100 to 200 cubic millimeters. Compared to the vehicle control, doses of Compound 3 as a single agent had an effect to delay tumor growth, with increased delay at higher doses. At the highest dose of 50 mg/kg, tumor growth inhibition (TGI) of about 45% was obtained at day 23 compared to vehicle. Formula A was tested at as a single agent at a single dose level of 75 mg/kg for which a similar TGI was obtained at day 23. Combinations of Compound 3 with Formula A showed similar levels of tumor growth suppression at all dose levels of Compound 3 tested and showed about 50-60% TGI. These results suggest that the synergy of combination treatments that was observed in vitro can be recapitulated in vivo and, interpreted more broadly, that combinations of PIM kinase inhibitors (exemplified by Compound 3) combined with PI3K inhibitors (exemplified by Formula A) could provide therapeutic benefit to patients including but not limited to those with multiple myeloma.

Figure 11:
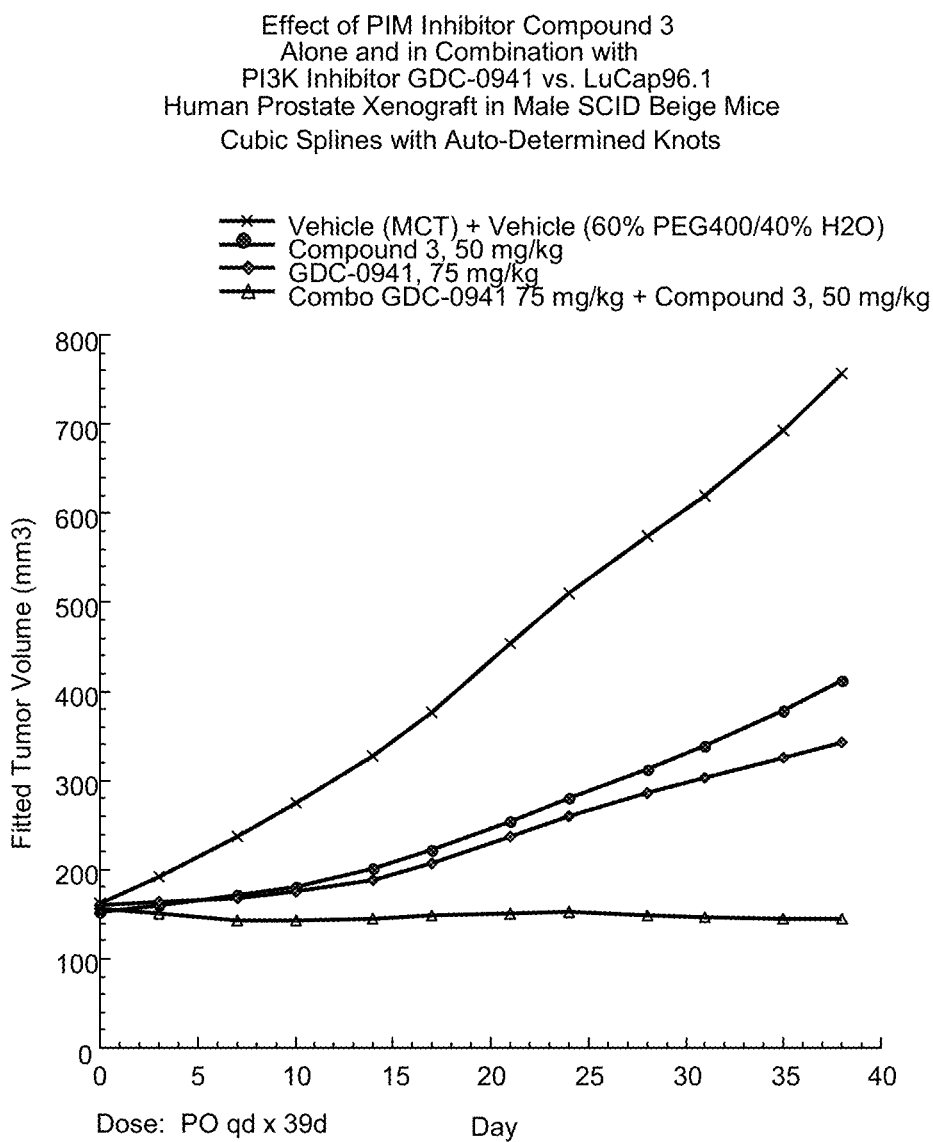
FIG. 11 shows the mean tumor volume change over 38 days in cohorts of SCID-beige mice with LuCap96.1 human prostate tumor cell xenografts dosed daily (po, qd) starting on day 0 with: Vehicle (60% PEG400 in DI Water); single agent therapies: 50 mg/kg (S)-5-amino-N-(4-(3-aminopiperidin-1-yl)pyridin-3-yl)-2-(2,6-difluorophenyl)thiazole-4-carboxamide (Compound 3, Example 3), 0r 75 mg/kg GDC-0941 Formula A; and the combination of 50 mg/kg (S)-5-amino-N-(4-(3-aminopiperidin-1-yl)pyridin-3-yl)-2-(2,6-difluorophenyl)thiazole-4-carboxamide (Compound 3, Example 3) and 75 mg/kg GDC-0941 Formula A.

FIG. 11 shows the mean tumor volume change over 38 days in cohorts of SCID-beige mice with LuCap96.1 human prostate tumor cell xenografts dosed daily (po, qd) starting on day 0 with: Vehicle (60% PEG400 in DI Water); single agent therapies: 50 mg/kg (S)-5-amino-N-(4-(3-aminopiperidin-1-yl)pyridin-3-yl)-2-(2,6-difluorophenyl)thiazole-4-carboxamide (Compound 3, Example 3), and 75 mg/kg GDC-0941

Formula A; and the combination of 50 mg/kg (S)-5-amino-N-(4-(3-aminopiperidin-1-yl)pyridin-3-yl)-2-(2,6-difluorophenyl)thiazole-4-carboxamide (Compound 3, Example 3) and 75 mg/kg GDC-0941 Formula A.

Dosing of all cohorts commenced on Day 0 when the mean tumor volume of all cohorts was between about 100 to 200 cubic millimeters. Compared to the vehicle control, doses of either Compound 3 or Formula A as single agents had an effect to delay tumor growth, with tumor growth inhibition (TGI) of about 60-70% was obtained at day 38 compared to vehicle. Combination of Compound 3 with Formula A showed about 100% TGI. These results suggest that combination of PIM kinase inhibitors (exemplified by Compound 3) combined with PI3K inhibitors (exemplified by Formula A) could provide therapeutic benefit to patients including but not limited to those with prostate carcinoma.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, inhalation and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or in combination with one or more chemotherapeutic agents, for example those described herein. Such conjoint treatment may be achieved by way of the simultaneous, sequential or separate dosing of the individual components of treatment.

Pharmaceutical compositions also embrace isotopically-labeled formula I compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically-labeled compounds of the present invention (for example, those labeled with $^3$H and $^{14}$C) are useful in compound and/or substrate tissue distribution assays. Tritiated ($^3$H) and carbon-14 ($^{14}$C) isotopes are useful for their ease of preparation and detectability. Further, substitution with heavier isotopes such as deuterium ($^2$H) may afford certain therapeutic advantages resulting from greater metabolic stability (for example, increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Ester, Pa., 15.sup.th Edition (1975).

Also falling within the scope of this invention are the in vivo metabolic products of formula I compounds described herein. Such products may result for example from the oxidation, reduction, hydrolysis, amidation, deamidation, esterification, deesterification, enzymatic cleavage, and the like, of the administered compound. Accordingly, the invention includes metabolites of formula I compounds, including compounds produced by a process comprising contacting a compound of this invention with a mammal for a period of time sufficient to yield a metabolic product thereof.

In another embodiment of the invention, an article of manufacture, or "kit", containing formula I compounds useful for the treatment of the diseases and disorders described above is provided. In one embodiment, the kit comprises a container comprising a formula I compound. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or a formulation thereof which is effective for treating the condition and may have a sterile access port (for example, the container may be an intravenous solution bag or a vial having a stopper pierceable by a hypodermic injection needle). At least one active agent in the composition is a formula I compound. The label or package insert indicates that the composition is used for treating the condition of choice, such as cancer. In one embodiment, the label or package inserts indicates that the composition comprising a Formula I compound can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of formula I and, if present, the second pharmaceutical formulation. For example, if the kit comprises a first composition comprising a compound of formula I and a second pharmaceutical formulation, comprising for example chemotherapeutic agent Formula A or B compound, the kit may further comprise directions for the simultaneous, sequential or separate administration of the first and second pharmaceutical compositions to a patient in need thereof.

In another embodiment, the kits are suitable for the delivery of solid oral forms of a compound of formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Where the kit comprises a composition of formula I and a second therapeutic agent, i.e. the chemotherapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (for example, oral and parenteral), are administered at different dosage intervals, or when titration of the individual components of the combination is desired by the prescribing physician.

EXAMPLES

Example i

Pim-1, Pim-2, and Pim-3 enzymes were generated as fusion proteins expressed in bacteria and purified by IMAC column chromatography (Sun, X., Chiu, J. F., and He, Q. Y. (2005) Application of immobilized metal affinity chromatography in proteomics. *Expert Rev. Proteomics.*, 2, 649-657). Reaction Buffer contained 10 mM HEPES, pH 7.2, 10 mM $MgCl_2$, 0.01% Tween 20, 2 mM DTT. Termination Buffer contained 190 mM HEPES, pH 7.2, 0.015% Brij-35, 0.2% Coating Reagent 3 (Caliper Life Sciences, Hopkinton, Mass.), 20 mM EDTA. Separation Buffer contained 100 mM HEPES, pH 7.2, 0.015% Brij-35, 0.1% Coating Reagent 3, 1:200 Coating Reagent 8 (Caliper Life Sciences, Hopkinton, Mass.), 10 mM EDTA and 5% DMSO.

PIM reactions were carried out in a final volume of 10 µL per well in a 384-well plate. A standard enzymatic reaction, initiated by the addition of 5 µL 2×ATP and test compound to 5 µA of 2× enzyme and FAM-Pimtide substrate (American Peptide Company (Sunnyvale, Calif.), contained 20 pM PIM1, 50 pM PIM2, or 55 pM PIM3, 1 µM FAM-Pimtide, and 10 µM ATP, in Reaction Buffer. After 90 minutes of incubation at room temperature, the phosphorylation reaction was stopped by the addition of 10 µL Termination Buffer. The product and substrate in each independent reaction were separated on a 12-sipper microfluidic chip (Caliper Life Sciences, Hopkinton, Mass.) run on a Caliper LC3000® (Caliper Life Sciences, Hopkinton, Mass.). The separation of product and substrate was optimized by choosing voltages and pressure using Caliper's Optimizer software (Hopkinton, Mass.). The separation conditions used a downstream voltage of −500V, an upstream voltage of −2150V, and a screening pressure of −1.2 psi. The product and substrate fluorophore were excited at 488 nm and detected at 530 nm. Substrate conversion was calculated from the electrophoregram using HTS Well Analyzer software (Caliper Life Sciences, Hopkinton, Mass.). Ki values for the test compound were calculated.

Example ii

BaF3 parental line was obtained from the DSMZ repository. BaF3 lines transfected with PIM1 or PIM2 were generated. Mouse IL-3 was purchased from R&D Systems. G418 was purchased from Clontech. Media for BaF3 parental line contained RPMI, 10% FBS, 2 mM L-Glutamine, 2 ng/mL mIL-3. Media for BaF3 PIM1 & 2 lines contained RPMI, 10% FBS, 2 mM L-Glutamine, 250 µg/mL. Media for MM1.S line contained RPMI, 10% FBS, 2 mM L-Glutamine.

BaF3 parental cells, BaF3 PIM1 cells, BaF3 PIM2 cells, and MM1.S cells were seeded at 2 k/well, 5 k/well, 5 k/well, and 10 k/well respectively, in a 384-well plate, at 45 µL/well. Test compound was added at 5 µL/well. BaF3 cells (parental and transfected) were incubated overnight, while MM1.S cells were incubated for 72 hours at 37° C., 5% $CO_2$. Cell Titer Glo Reagent (Promega) was added at 50 µL/well, the plates were incubated for 30 minutes, and their luminescence read on an HT Analyst. $IC_{50}/EC_{50}$ values for the test compound were calculated.

Example iii

Representative compounds of the present invention were tested in assays described in EXAMPLES i and ii as described above and found to exhibit a $Ki/IC_{50}/EC_{50}$ as shown below. Table 5 includes representative biochemical binding and in vitro cell proliferation data for the exemplary Compounds I-66.

TABLE 5

| | EXAMPLE i | | | EXAMPLE ii | | |
|---|---|---|---|---|---|---|
| EXAMPLE # | PIM1 LC3K (Ki) μM | PIM2 LC3K (Ki) μM | PIM3 LC3K (Ki) μM | Prolif BaF3_PIM1 (IC$_{50}$) μM | Prolif BaF3_PIM2 (IC$_{50}$) μM | Prolif MM1S ATP (EC$_{50}$) μM |
| 1 | 0.0000224 | 0.0000671 | 0.0000156 | 0.0332 | 1.4 | 0.108 |
| 2 | 0.0000355 | 0.000126 | 0.0000205 | 0.0672 | 2 | 0.218 |
| 3 | 0.0000102 | 0.0000457 | 0.0000156 | 0.0135 | 2 | 0.0497 |
| 4 | 0.000023 | 0.000154 | 0.000026 | 0.0558 | >2.5 | 0.16 |
| 5 | 0.000044 | 0.000493 | 0.000050 | 0.30 | 2.8 | 1.5 |
| 6 | 0.000063 | 0.000379 | 0.000032 | 0.117 | 1.4 | 0.595 |
| 7 | 0.000091 | 0.000203 | 0.0000215 | 0.073 | 3.1 | 0.141 |
| 8 | 0.00347 | 0.0163 | 0.00953 | 0.713 | >20 | >20 |
| 9 | 0.000084 | 0.00016 | 0.000014 | 0.0688 | 1.9 | 0.0897 |
| 10 | 0.0367 | 0.0512 | 0.024 | 3.6 | — | >20 |
| 11 | 0.000502 | 0.000885 | 0.000166 | 0.607 | 13.2 | 9.2 |
| 12 | 0.000172 | 0.00106 | 0.000072 | 2.3 | 4.2 | 6.8 |
| 13 | 0.000102 | 0.000403 | 0.000040 | 20 | 20 | >20 |
| 14 | 0.0367 | 0.195 | 0.00925 | 20 | 20 | >20 |
| 15 | 0.00193 | 0.0164 | 0.00189 | 0.945 | 3.3 | 4.4 |
| 16 | 0.00156 | 0.00383 | 0.00226 | 0.926 | >20 | 10-20 |
| 17 | 0.014 | 0.0765 | 0.00681 | >20 | >20 | >20 |
| 18 | 0.000096 | 0.000596 | 0.000033 | 0.257 | 12.3 | 0.767 |
| 19 | 0.000735 | 0.00355 | — | 0.581 | >20 | 3.2 |
| 20 | 1.2 | 4.9 | 0.496 | — | — | — |
| 21 | 0.42 | 0.242 | 0.138 | >20 | >20 | >20 |
| 22 | 0.000054 | 0.000495 | 0.000052 | 0.52 | >20 | 4.7 |
| 23 | 0.000034 | 0.000153 | 0.000031 | 2.5 | 1.8 | 0.137 |
| 24 | 0.00043 | 0.0163 | 0.00176 | >14 | >20 | 20 |
| 25 | 0.000511 | 0.00172 | 0.000339 | 1.5 | 4.6 | 1.5 |
| 26 | 0.000014 | 0.00015 | 0.000022 | 0.0282 | 2.4 | 0.148 |
| 27 | 0.000040 | 0.000248 | 0.000050 | 0.0757 | 3.9 | 0.558 |
| 28 | 0.000102 | 0.000434 | 0.000118 | 0.135 | 2.8 | 1.9 |
| 29 | 0.000058 | 0.000565 | 0.000070 | 0.0489 | 4.3 | 1.6 |
| 30 | 0.000076 | 0.000429 | 0.000033 | 0.0522 | >5 | 0.163 |
| 31 | 0.0000464 | 0.000339 | 0.000023 | 0.0665 | 2.3 | 1.3 |
| 32 | 0.000054 | 0.000127 | 0.000022 | 1.7 | >20 | 0.65 |
| 33 | 0.00060 | 0.00251 | — | 0.41 | 13.3 | 3.5 |
| 34 | 0.000012 | 0.0000957 | 0.000022 | 0.0191 | >2.5 | 0.0568 |
| 35 | 0.000709 | 0.00528 | 0.00113 | 0.0293 | 2 | 2.3 |
| 36 | 0.00218 | 0.00869 | 0.00377 | 0.562 | — | 14 |
| 37 | 0.00114 | 0.000635 | — | 2.2 | — | 2.1 |
| 38 | 0.00373 | 0.0338 | 0.0127 | 3.2 | — | 11.9 |
| 39 | 0.000306 | 0.00169 | 0.000143 | 0.375 | 5.1 | 3.2 |
| 40 | 0.000129 | 0.000725 | 0.000037 | 0.164 | 6.5 | 2.5 |
| 41 | 0.000049 | 0.000208 | 0.000022 | 0.069 | 3.9 | 2 |
| 42 | 0.000036 | 0.0000939 | 0.000022 | 0.0304 | 2.1 | 0.121 |
| 43 | 0.000061 | 0.0000185 | 0.000022 | 0.0455 | 3.9 | 0.237 |
| 44 | 0.000032 | 0.000512 | 0.000113 | 0.0381 | 1.9 | 0.191 |
| 45 | 0.000561 | 0.00278 | 0.000338 | 0.613 | 12.5 | 5.5 |
| 46 | 0.000264 | 0.00193 | 0.000259 | 0.148 | 9.4 | 4.8 |
| 47 | 0.00398 | 0.0598 | 0.00211 | 3.9 | >20 | >20 |
| 48 | 0.00133 | 0.00684 | 0.000487 | 1.4 | — | 8 |
| 49 | 0.0297 | 0.259 | 0.0912 | 4 | — | >20 |
| 50 | 0.00050 | 0.00688 | 0.000333 | 0.614 | 1.4 | 0.743 |
| 51 | 0.0000812 | 0.000265 | 0.000041 | 0.197 | >20 | 0.156 |
| 52 | 0.0000269 | 0.000495 | 0.000061 | 2.2 | >20 | 1.3 |
| 53 | 0.000208 | 0.000839 | 0.000146 | 0.273 | 7.6 | 0.66 |
| 54 | 0.0269 | 0.0723 | 0.0231 | 7.8 | >20 | 15.7 |
| 55 | 0.000032 | 0.00012 | 0.000028 | — | — | 0.158 |
| 56 | 0.000115 | 0.000666 | 0.000080 | 1.5 | >20 | 0.953 |
| 57 | 0.00011 | 0.00288 | 0.000229 | 0.494 | >20 | 5.1 |
| 58 | 0.00089 | 0.00185 | 0.000554 | 0.232 | 6.5 | 3.1 |
| 59 | 0.0182 | 0.355 | 0.048 | >20 | >20 | >20 |
| 60 | 0.00107 | 0.00116 | 0.000279 | 0.465 | 17.6 | 1.4 |
| 61 | 0.000642 | 0.0182 | 0.00101 | 7.1 | >20 | 10.4 |
| 62 | 0.00134 | 0.00887 | 0.000326 | 6 | 10.4 | 0.364 |
| 63 | 0.000437 | 0.00386 | 0.000246 | 3.4 | 12.9 | 19.9 |
| 64 | 0.0216 | 0.0577 | 0.018 | — | — | — |
| 65 | 0.0949 | 0.0971 | 0.0473 | >20 | >20 | >20 |
| 66 | 0.000050 | 0.0000894 | 0.000022 | 0.0406 | 2.1 | 2.8 |

Multiple myeloma cell lines used in the combination experiments of FIGS. 1-4, include EJM, KMS.11, KMS.12.BM, LP-1, MM1.S, MOLP-8, NCI H929, OPM2, RPMI8226, U266, AMO-1, JJN3, Karpas620, KMS.12.PE, L363, MOLP-2, SKMM2, KMM1, KMS.20, KMS.21, KMS.26, KMS.27, KMS.28.BM, KMS.28.PE, and KMS.34.

Intermediates

Preparation of compound ethyl 2-amino-2-cyanoacetate: To a stirred solution of (E)-ethyl 2-cyano-2-(hydroxyimino) acetate (20 g, 0.14 mol) in water (250 mL) was added a saturated solution of NaHCO$_3$ in water (160 mL), followed by the addition of Na$_2$S$_2$O$_4$ (60 g, 0.423 mol). The reaction mixture was warmed up to 35° C. and stirred for additional 2 hr. It was then saturated with NaCl (150 g) and extracted with DCM (3×350 mL). Combined organic layers were washed with brine, dried over Na$_2$SO$_4$, filtered and concentrated in vacuo to give ethyl 2-amino-2-cyanoacetate as a red oil (7.8 g, 43%) that was used at the next step without additional purification. $^1$H-NMR (CDCl$_3$, 500 MHz) δ (ppm): 4.45 (s, 1H), 4.34 (q, J=7.0 Hz, 2H), 1.36 (t, J=7.0 Hz, 3H); MS (ESI) m/z: 129 [M+H$^+$].

Preparation of compound ethyl 2-benzamido-2-cyanoacetate: To a stirred solution of compound ethyl 2-amino-2-cyanoacetate (0.64 g, 5 mmol) in DCM (15 mL) was added a saturate solution of NaHCO$_3$ in water (15 mL). With vigorously stirring, benzoyl chloride (0.84 g, 6 mmol) was added. The reaction mixture was stirred at ambient temperature for additional 30 min at which time it was extracted with DCM (3×15 mL). Combined organic layers were washed with brine (20 mL) and dried over Na$_2$SO$_4$, filtered, concentrated in vacuo. Resulted residue was purified by silica gel column chromatography (5:1 PE/EtOAc) to afford ethyl 2-benzamido-2-cyanoacetate (0.25 g, 22%) as white solid: $^1$H-NMR (CDCl$_3$, 500 MHz) δ (ppm): 7.83-7.85 (m, 2H), 7.59 (t, J=7.5 Hz, 1H), 7.49 (t, J=7.5 Hz, 2H), 7.02 (d, J=7.0 Hz, 1H), 5.72 (d, J=7.5 Hz, 1H), 4.40 (q, J=7.5 Hz, 2H), 1.39 (t, J=7.0 Hz, 3H); MS (ESI) m/z: 233 [M+H$^+$].

Preparation of compound ethyl 5-amino-2-phenylthiazole-4-carboxylate: To a stirred solution of compound ethyl 2-benzamido-2-cyanoacetate (0.46 g, 2 mmol) in pyridine (20 mL) was added Lawesson's reagent (0.81 g, 2 mmol). The reaction mixture was heated at reflux for 15 hr. It was then concentrated and diluted with EtOAc (40 mL). The diluted mixture was washed with water (3×20 mL), brine (10 mL), dried over Na$_2$SO$_4$, filtered, and concentrated in vacuo. The residue was purified by silica gel column chromatography (10:1 PE/EtOAc) to afford ethyl 5-amino-2-phenylthiazole-4-carboxylate (0.2 g, 40%) as yellow solid: $^1$H-NMR (CDCl$_3$, 500 MHz) δ (ppm): 7.80 (d, J=6.5 Hz, 1H), 7.36-7.41 (m, 3H), 4.43 (q, J=7.0 Hz, 2H), 1.44 (t, J=7.0 Hz, 3H); MS (ESI) m/z: 249 [M+H$^+$].

Preparation of compound ethyl 5-(tert-butoxycarbonylamino)-2-phenylthiazole-4-carboxylate: To a solution of compound ethyl 5-amino-2-phenylthiazole-4-carboxylate (248 mg, 1 mmol) in CH$_3$CN (10 mL) was added DMAP (6 mg, 0.05 mmol) followed by (Boc)$_2$O (262 mg, 1.2 mmol). The reaction mixture was maintained at ambient temperature for additional 30 min. The mixture was then evaporated in vacuo to give compound ethyl 5-(tert-butoxycarbonylamino)-2-phenylthiazole-4-carboxylate as a red solid (340 mg, 95%) that was used at the next step without further purification.

Preparation of compound 5-(tert-butoxycarbonylamino)-2-phenylthiazole-4-carboxylic acid: To a solution of compound ethyl 5-(tert-butoxycarbonylamino)-2-phenylthiazole-4-carboxylate (348 mg, 1 mmol) in MeOH/H$_2$O (10 mL, 1:1) was added LiOH.H$_2$O (20 mg, 5 mmol). The reaction mixture was heated at 50-55° C. until starting material disappeared from TLC. It was cooled at ~0-4° C. and conc. HCl added dropwise until pH ~5. The resulted mixture was then extracted with DCM (3×20 mL). Combined organic layers were washed with brine (2×20 mL), dried over Na$_2$SO$_4$, filtered, and concentrated in vacuo. The residue was purified by silica gel column chromatography (50:1 DCM:MeOH) to give the desired product 5-(tert-butoxycarbonylamino)-2-phenylthiazole-4-carboxylic acid (0.22 g, 68%) as white solid: $^1$H-NMR (CDCl$_3$, 500 MHz) δ (ppm): 9.69 (s, 1H), 7.89-7.91 (m, 2H), 7.46-7.47 (m, 3H), 1.57 (s, 9H); MS (ESI) m/z: 321 [M+H$^+$].

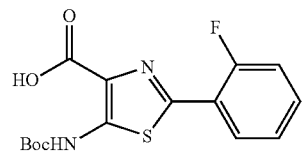 [SMILES: CC(C)(C)OC(=O)Nc1sc(-c2ccccc2F)nc1C(=O)O]

5-(tert-butoxycarbonylamino)-2-(2-fluorophenyl)thiazole-4-carboxylic acid was prepared from 2-fluorobenzoyl chloride using procedures analogous to those described above and in Scheme 1: $^1$H-NMR (CDCl$_3$, 500 MHz) δ (ppm): 9.70 (s, 1H), 8.19-8.23 (m, 1H), 7.42-7.45 (m, 1H), 7.20-7.30 (m, 2H), 1.57 (s, 9H); MS (ESI) m/z: 339 [M+H$^+$].

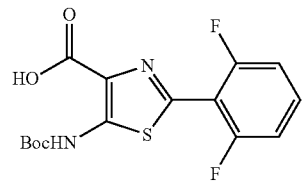 [SMILES: CC(C)(C)OC(=O)Nc1sc(-c2c(F)cccc2F)nc1C(=O)O]

5-(tert-butoxycarbonylamino)-2-(2,6-difluorophenyl) thiazole-4-carboxylic acid was prepared from 2,6-difluorobenzoyl chloride using procedures analogous to those described above and in Scheme 1: $^1$H-NMR (CD$_3$OD, 500 MHz) δ (ppm): 7.42-7.46 (m, 1H), 7.06 (t, J=8.5 Hz, 2H), 1.47 (s, 9H); MS (ESI) m/z: 355 [M+H$^+$].

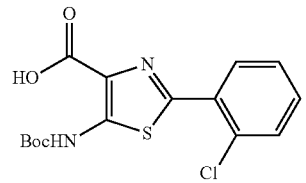 [SMILES: CC(C)(C)OC(=O)Nc1sc(-c2ccccc2Cl)nc1C(=O)O]

5-(tert-butoxycarbonylamino)-2-(2-chlorophenyl)thiazole-4-carboxylic acid was prepared from 2-chlorobenzoyl chloride using procedures analogous to those described above and in Scheme 1: $^1$H-NMR (DMSO, 500 MHz) δ (ppm): 13.57 (s, 1H), 10.05 (s, 1H), 8.14-8.17 (m, 1H), 7.63-

7.65 (m, 1H), 7.49-7.51 (m, 2H), 1.53 (s, 9H); MS (ESI) m/z: 355 [M+H⁺].

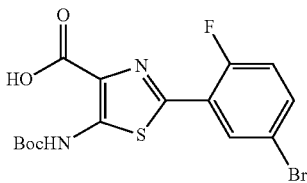 [SMILES: CC(C)(C)OC(=O)Nc1sc(-c2cc(Br)ccc2F)nc1C(=O)O]

2-(5-bromo-2-fluorophenyl)-5-(tert-butoxycarbonylamino)thiazole-4-carboxylic acid was prepared from 5-bromo-2-fluorobenzoyl chloride using procedures analogous to those described above and in Scheme 1: $^1$H-NMR (CDCl$_3$, 500 MHz) δ (ppm): 9.70 (s, 1H), 8.32-8.34 (m, 1H), 7.49-7.52 (m, 1H), 7.09-7.13 (m, 1H), 1.57 (s, 9H); MS (ESI) m/z: 418 [M+H⁺].

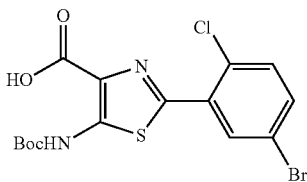 [SMILES: CC(C)(C)OC(=O)Nc1sc(-c2cc(Br)ccc2Cl)nc1C(=O)O]

2-(5-bromo-2-chlorophenyl)-5-(tert-butoxycarbonylamino)thiazole-4-carboxylic acid was prepared from 5-bromo-2-chlorobenzoyl chloride using procedures analogous to those described above and in Scheme 1: $^1$H-NMR (CDCl$_3$, 500 MHz) δ (ppm): 9.70 (s, 1H), 8.31 (d, J=2.5 Hz, 1H), 7.47 (dd, J=2.5 Hz, J=8.5 Hz, 1H), 7.35 (d, J=9.0 Hz, 1H), 1.57 (s, 9H); MS (ESI) m/z: 433 [M+H⁺].

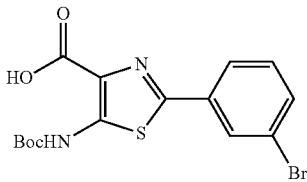 [SMILES: CC(C)(C)OC(=O)Nc1sc(-c2cccc(Br)c2)nc1C(=O)O]

2-(3-bromophenyl)-5-(tert-butoxycarbonylamino)thiazole-4-carboxylic acid was prepared from 3-bromobenzoyl chloride using procedures analogous to those described above and in Scheme 1: $^1$H-NMR (CDCl$_3$, 500 MHz) δ (ppm): 9.68 (s, 1H), 8.08 (s, 1H), 7.78 (d, J=8.0 Hz, 1H), 7.56 (d, J=8.0 Hz, 1H), 7.32 (t, J=8.0 Hz, 1H), 1.57 (s, 9H); MS (ESI) m/z: 399 [M+H⁺].

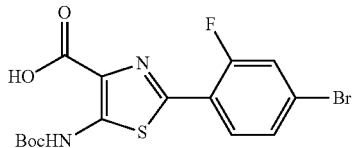 [SMILES: CC(C)(C)OC(=O)Nc1sc(-c2ccc(Br)cc2F)nc1C(=O)O]

2-(4-bromo-2-fluorophenyl)-5-(tert-butoxycarbonylamino)thiazole-4-carboxylic acid was prepared from 4-bromo-2-fluorobenzoyl chloride using procedures analogous to those described above and in Scheme 1: $^1$H-NMR (CDCl$_3$, 500 MHz) δ (ppm): 9.67 (s, 1H), 8.07 (t, J=8.0 Hz, 1H), 7.42 (d, J=9.5 Hz, 1H), 1.57 (s, 9H); MS (ESI) m/z: 417 [M+H⁺].

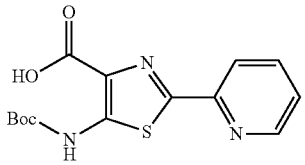 [SMILES: CC(C)(C)OC(=O)Nc1sc(-c2ccccn2)nc1C(=O)O]

5-(tert-butoxycarbonylamino)-2-(pyridin-2-yl)thiazole-4-carboxylic acid was prepared from using procedures analogous to those described above and in Scheme 1 except the following modification. Preparation of ethyl 2-cyano-2-(picolinamido)acetate: to a solution of picolinic acid (1.23 g, 10 mmol), EDC.HCl (1.91 g, 10 mmol) and HOBT (1.35 g, 10 mmol) in THF (80 mL) was added DIPEA (3.6 g, 30 mmol) at ambient temperature. The reaction mixture was maintained at the same temperature for 1 hr at which time a solution of ethyl 2-amino-2-cyanoacetate (1.28 g, 10 mmol) in THF (5 mL) was added. The reaction mixture was stirred at ambient temperature for additional 6 hr. It was then concentrated, and the residue was purified by silica gel column chromatography (5:1 PE/EtOAc) to give ethyl 2-cyano-2-(picolinamido)acetate (0.7 g, 30%) as yellow solid. 5-(tert-butoxycarbonylamino)-2-(pyridin-2-yl)thiazole-4-carboxylic acid: $^1$H-NMR (CDCl$_3$, 500 MHz) δ (ppm): 9.72 (s, 1H), 8.61 (d, J=4.5 Hz, 1H), 8.09 (d, J=8.0 Hz, 1H), 7.81 (t, J=7.5 Hz, 1H), 7.34 (dd, J=5.5 Hz, J=7.0 Hz, 1H), 1.57 (s, 9H); MS (ESI) m/z: 322 [M+H⁺].

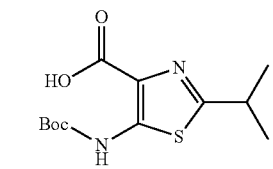

5-(tert-butoxycarbonylamino)-2-isopropylthiazole-4-carboxylic acid was prepared from isobutyryl chloride using procedures analogous to those described above and in Scheme 1: $^1$H-NMR (CDCl$_3$, 500 MHz) δ (ppm): 9.54 (s, 1H), 3.16-3.21 (m, 1H), 1.54 (s, 9H), 1.37 (d, J=7.0 Hz, 6H); MS (ESI) m/z: 287 [M+H⁺].

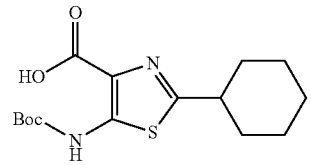 [SMILES: CC(C)(C)OC(=O)Nc1sc(C2CCCCC2)nc1C(=O)O]

5-(tert-butoxycarbonylamino)-2-cyclohexylthiazole-4-carboxylic acid was prepared from cyclohexanecarboxylic acid chloride using procedures analogous to those described above and in Scheme 1: $^1$H-NMR (CDCl$_3$, 500 MHz) δ (ppm): 9.53 (s, 1H), 2.84-2.89 (m, 1H), 2.08-2.12 (m, 2H), 1.84 (dd, J=3.5 Hz, J=10.0 Hz, 2H), 1.73 (d, J=13.0 Hz, 1H), 1.53 (s, 9H), 1.35-1.50 (m, 4H), 1.25-1.27 (m, 1H); MS (ESI) m/z: 327 [M+H⁺].

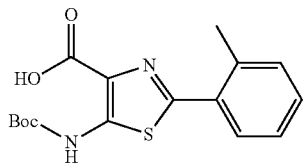 [SMILES: Cc1ccccc1-c1nc(C(=O)O)c(NC(=O)OC(C)(C)C)s1]

5-(tert-butoxycarbonylamino)-2-o-tolylthiazole-4-carboxylic acid was prepared from 2-methylbenzoyl chloride using procedures analogous to those described above and in Scheme 1: ¹H-NMR (CD₃OD, 500 MHz) δ (ppm): 7.34 (s, 1H), 7.13-7.22 (m, 3H), 2.32 (s, 3H), 1.43 (s, 9H); MS (ESI) m/z: 335 [M+H⁺].

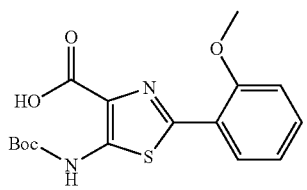 [SMILES: COc1ccccc1-c1nc(C(=O)O)c(NC(=O)OC(C)(C)C)s1]

5-(tert-butoxycarbonylamino)-2-(2-methoxyphenyl)thiazole-4-carboxylic acid was prepared from 2-methoxybenzoyl chloride using procedures analogous to those described above and in Scheme 1: ¹H-NMR (CD₃OD, 500 MHz) δ (ppm): 9.63 (s, 1H), 8.27 (d, J=7.5 Hz, 1H), 7.42 (t, J=8.0 Hz, 1H), 7.09 (t, J=7.5 Hz, 1H), 7.04 (d, J=9.0 Hz, 1H), 1.57 (s, 9H); MS (ESI) m/z: 351 [M+H⁺].

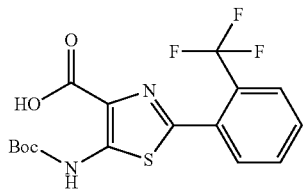 [SMILES: CC(C)(C)OC(=O)Nc1sc(-c2ccccc2C(F)(F)F)nc1C(=O)O]

5-(tert-butoxycarbonylamino)-2-(2-(trifluoromethyl)phenyl)thiazole-4-carboxylic acid was prepared from 2-(trifluoromethyl)benzoyl chloride using procedures analogous to those described above and in Scheme 1: ¹H-NMR (CD₃OD, 500 MHz) δ (ppm): 7.76 (d, J=7.5 Hz, 1H), 7.58-7.64 (m, 3H), 1.46 (s, 9H); MS (ESI) m/z: 389 [M+H⁺].

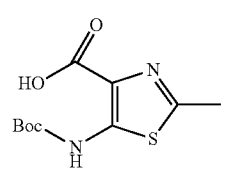

5-(tert-butoxycarbonylamino)-2-methylthiazole-4-carboxylic acid was prepared from acetyl chloride using procedures analogous to those described above and in Scheme 1: ¹H-NMR (CDCl₃, 500 MHz) δ (ppm): 9.62 (s, 1H), 2.62 (s, 3H), 1.54 (s, 9H); MS (ESI) m/z: 259 [M+H⁺].

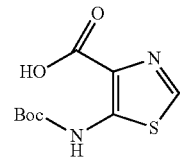

5-(tert-butoxycarbonylamino)thiazole-4-carboxylic acid was prepared using procedures analogous to those described above and in Scheme 1 except the following modification. Preparation of ethyl 2-cyano-2-formamidoacetate: under N₂, HCOOH (2.44 g, 53 mmol) was added to Ac₂O (6.48 g, 63.6 mmol) at 0° C. After it was allowed to warm to ambient temperature the reaction was heated at 50° C. for 15 hr. It was allowed to cool to ambient temperature. This mixed acid anhydride was then added dropwise to a solution of ethyl 2-amino-2-cyanoacetate (128 mg, 1 mmol) in dry THF (5 mL) at 0° C. After the cooling bath was removed, the reaction was maintained at ambient temperature for additional 1 hr. The reaction mixture was concentrated and purified by silica gel column chromatography (5:1 PE/EtOAc) to afford ethyl 2-cyano-2-formamidoacetate (110 mg, 70%) as a white solid.

5-(tert-butoxycarbonylamino)thiazole-4-carboxylic acid: ¹H-NMR (CDCl₃, 500 MHz) δ (ppm): 9.70 (s, 1H), 8.29 (s, 1H), 1.55 (s, 9H); MS (ESI) m/z: 245 [M+H⁺].

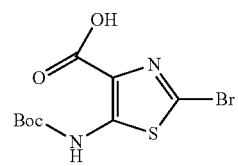

To a solution of 5-(tert-butoxycarbonylamino)thiazole-4-carboxylic acid (1.72 g, 10 mmol) in DCM (50 mL) was added in three portions NBS (1.95 g, 11 mmol); the reaction mixture was stirred at ambient temperature for 1 h. Reaction was concentrated in vacuo; resulted residue was purified by silica gel column chromatography (6:1 Pet-ether-EtOAc) to afford 2-bromo-5-(tert-butoxycarbonylamino)thiazole-4-carboxylic acid (1.75 g, 70%) as white solid: ¹H-NMR (CDCl₃, 500 MHz) δ (ppm): 13.65 (s, 1H), 10.03 (s, 1H), 1.49 (s, 9H). MS (ESI) m/z: 324 [M+H⁺]

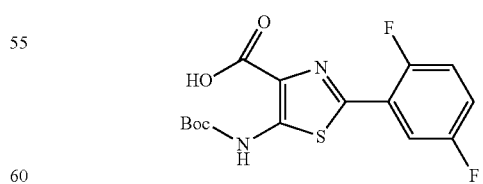

5-(tert-butoxycarbonylamino)-2-(2,5-difluorophenyl)thiazole-4-carboxylic acid was prepared from 2,5-difluorobenzoyl chloride using procedures analogous to those described above and in Scheme 1: ¹H-NMR (CDCl₃, 500 MHz) δ (ppm): 9.68 (s, 1H), 7.87-7.91 (m, 1H), 7.15-7.26 (m, 1H), 7.08-7.13 (m, 1H), 1.57 (s, 9H); MS (ESI) m/z: 357 [M+H⁺].

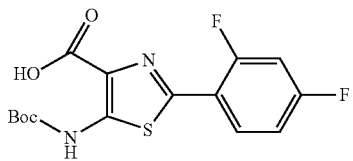

5-(tert-butoxycarbonylamino)-2-(2,4-difluorophenyl)thiazole-4-carboxylic acid was prepared from 2,4-difluorobenzoyl chloride using procedures analogous to those described above and in Scheme 1: ¹H-NMR (CDCl₃, 500 MHz) δ (ppm): 9.66 (s, 1H), 8.16-8.21 (m, 1H), 6.95-7.04 (m, 2H), 1.62 (s, 9H); MS (ESI) m/z: 357 [M+H⁺].

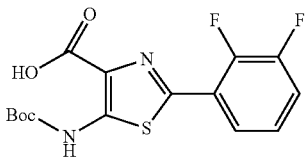 [SMILES: CC(C)(C)OC(=O)Nc1sc(-c2cccc(F)c2F)nc1C(=O)O]

5-(tert-butoxycarbonylamino)-2-(2,3-difluorophenyl)thiazole-4-carboxylic acid was prepared from 2,3-difluorobenzoyl chloride using procedures analogous to those described above and in Scheme 1: ¹H-NMR (CD₃OD, 400 MHz) δ (ppm): 7.45 (s, 1H), 7.07-7.16 (m, 2H), 1.42 (s, 9H); MS (ESI) m/z: 357 [M+H⁺].

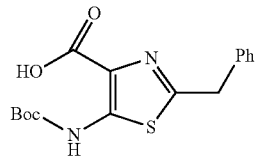 [SMILES: CC(C)(C)OC(=O)Nc1sc(Cc2ccccc2)nc1C(=O)O]

2-benzyl-5-(tert-butoxycarbonylamino)thiazole-4-carboxylic acid was prepared from 2-phenylacetyl chloride using the above general procedures: ¹H-NMR (CDCl₃, 500 MHz) δ (ppm): 9.63 (s, 1H), 7.27-7.35 (m, 5H), 4.25 (s, 2H), 1.50 (s, 9H); MS (ESI) m/z: 335 [M+H⁺].

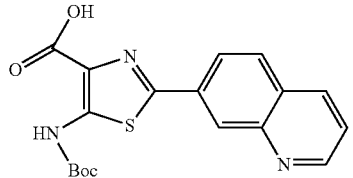 [SMILES: CC(C)(C)OC(=O)Nc1sc(-c2ccc3cccnc3c2)nc1C(=O)O]

5-(tert-butoxycarbonylamino)-2-(quinolin-7-yl)thiazole-4-carboxylic acid was prepared from quinoline-7-carbonyl chloride using procedures analogous to those described above and in Scheme 1: ¹H-NMR (DMSO, 500 MHz) δ (ppm): 10.14 (s, 1H), 9.11 (d, J=5 Hz, 1 h), 8.68 (s, 1H), 8.55 (s, 1H), 8.21-8.25 (m, 2H), 7.75-7.77 (m, 1H), 1.54 (s, 9H); MS (ESI) m/z: 372 [M+H⁺].

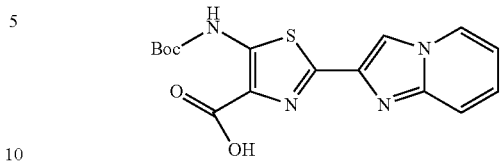

5-(tert-butoxycarbonylamino)-2-(imidazo[1,2-a]pyridin-2-yl)thiazole-4-carboxylic acid was prepared from imidazo[1,2-a]pyridine-2-carbonyl chloride using procedures analogous to those described above and in Scheme 1: ¹H-NMR (DMSO, 500 MHz) δ (ppm): 10.12 (s, 1H), 8.58 (d, 5 Hz, 1H), 8.45 (s, 1H), 7.61 (d, 5 Hz, 1H), 7.31-7.34 (m, 1H), 6.97-6.99 (m, 1H), 1.53 (s, 9H); MS (ESI) m/z: 361 [M+H⁺].

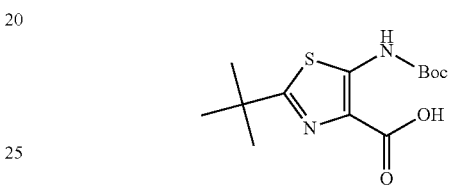

5-(tert-butoxycarbonylamino)-2-tert-butylthiazole-4-carboxylic acid was prepared from pivaloyl chloride using procedures analogous to those described above and in Scheme 1: ¹H-NMR (CDCl₃, 500 MHz) δ (ppm): 9.55 (s, 1H), 1.55 (s, 9H), 1.42 (s, 9H); MS (ESI) m/z: 301 [M+H⁺].

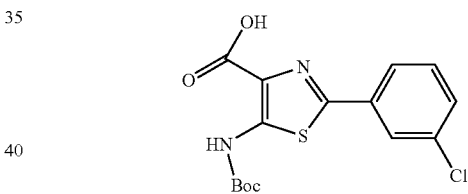

5-(tert-butoxycarbonylamino)-2-(3-chlorophenyl)thiazole-4-carboxylic acid was prepared from 3-chlorobenzoyl chloride using procedures analogous to those described above and in Scheme 1: ¹H-NMR (DMSO, 500 MHz) δ (ppm): 9.67 (s, 1H), 7.91 (s, 1H), 7.72 (d, J=7 Hz, 1H), 7.38-7.40 (m, 2H), 1.56 s, 9H); MS (ESI) m/z: 355 [M+H⁺].

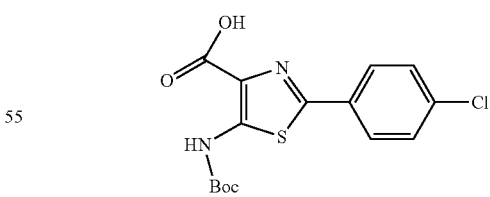

5-(tert-butoxycarbonylamino)-2-(4-chlorophenyl)thiazole-4-carboxylic acid was prepared from 4-chlorobenzoyl chloride using procedures analogous to those described above and in Scheme 1: ¹H-NMR (DMSO, 500 MHz) δ (ppm): 9.66 (s, 1H), 7.81 (d, J=8.5 Hz, 2H), 7.42 (d, J=8.5 Hz, 2H), 1.56 (s, 9H); MS (ESI) m/z: 355 [M+H⁺].

Preparation of compound 5-(tert-butoxycarbonylamino)-2-phenyl-1H-imidazole-4-carboxylic acid: Benzothioamide (1.37 g, 10 mmol) and benzylbromide (1.71 g, 10 mmol) in dry THF were heated to 60° C. for 2 h. After it was allowed to cool to room temperature, the reaction mixture was filtered. The desired benzyl benzimidothioate hydrobromide as a white solid (2 g, 65%) without further purification. To a solution of benzyl benzimidothioate hydrobromide (1.54 g, 5 mmol) in dry CHCl$_3$ was added in one portion dry pyridine (5 mmol) at ambient temperature followed by ethyl 2-amino-2-cyanoacetate (0.64 g, 5 mmol). The reaction mixture was then heated to 65° C. for 2 h. After cooling to room temperature, the mixture was filtered to give the ethyl 5-amino-2-phenyl-1H-imidazole-4-carboxylate as a yellow colored solid (0.8 g, 68%). This solid (0.46 g, 2 mmol) was added with dry THF, Boc$_2$O (0.87 g, 4 mmol), DMAP (24 mg, 0.2 mmol). The reaction was heated to 65° C. for 5 h. The solvent was evaporated in vacuo to give crude product. This crude product was then dissolved in MeOH—H$_2$O (30 mL, 1:1) and LiOH was added in one portion. The reaction mixture was heated at 70° C. until starting material disappeared by TLC (~4 h). The mixture was then cooled to ~0-4° C. and 1N aq HCl was added cautiously dropwise until pH ~5. The resulted mixture was extracted with DCM (3×20 mL). Combined organic layers were washed with brine (2×20 mL), dried over Na$_2$SO$_4$, filtered, and concentrated in vacuo. The residue was purified by prep-HPLC. The desired product 5-(tert-butoxycarbonylamino)-2-phenyl-1H-imidazole-4-carboxylic acid was obtained as white solid (0.1 g, 16%). $^1$H-NMR (DMSO, 500 MHz) δ (ppm): 9.01 (s, 1H), 8.05 (s, 2H), 7.35-7.42 (m, 3H), 1.45 (s, 9H); MS (ESI) m/z: 304 [M+H$^+$].

Preparation of compound 5-(tert-butoxycarbonylamino)-2-phenyloxazole-4-carboxylic acid: To a stirred solution of ethyl 2-benzamido-2-cyanoacetate (1.16 g, 5 mmol) in dry dioxane (20 mL) was added a solution of HCl in dioxane (4.0 M, 20 mL). The resulting mixture was heated at reflux for 10 h. After the solvent was evaporated in vacuo, the desired product ethyl 5-amino-2-phenyloxazole-4-carboxylate was obtained as a white solid (0.5 g, 50%). Boc-protection followed by hydrolysis of ethyl 5-amino-2-phenyloxazole-4-carboxylate (0.5 g, 2.2 mmol) using the same procedures described above gave the desired molecule 5-(tert-butoxycarbonylamino)-2-phenyloxazole-4-carboxylic acid (320 mg, 22% overall yield): $^1$H-NMR (DMSO, 500 MHz) δ (ppm): 13.09 (s, 1H), 9.80 (s, 1H), 7.89-7.92 (m, 2H), 7.56-7.57 (m, 3H), 1.46 (s, 9H); MS (ESI) m/z: 248 [M+H$^+$].

Exemplary Compounds

Example 1

(S)-5-amino-N-(4-(3-aminopiperidin-1-yl)pyridin-3-yl)-2-(2-fluorophenyl)thiazole-4-carboxamide

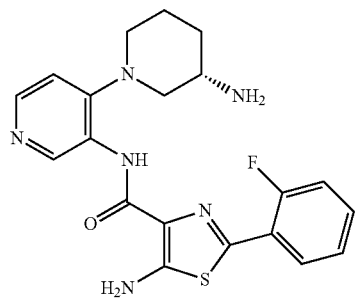 [SMILES: Nc1sc(-c2ccccc2F)nc1C(=O)Nc1cnccc1N1CCC[C@H](N)C1]

To a 50 mL round bottom flask containing 5-(tert-butoxycarbonylamino)-2-(2-fluorophenyl)thiazole-4-carboxylic acid (250 mg, 739 umol), (S)-tert-butyl 1-(3-aminopyridin-4-yl)piperidin-3-ylcarbamate (216 mg, 739 umol) and HATU (562 mg, 1.48 mmol) were added methylene chloride (10 mL) and diisopropylethylamine (0.382 g, 2.96 mmol). The reaction mixture was stirred for 24 hr at room temperature and the reaction was monitored by LCMS. Upon completion of the reaction, the solvent was distilled off and the crude material was purified via flash chromatography, heptane/ethyl acetate 20% to 80% to afford yellow oil (381 mg, 84%).

In a 50 mL round bottom flask was added protected amide from the step above (381 mg, 622 umol), methylene chloride (5 mL) and trifluoroacetic acid (3 mL, 39.6 mmol). The mixture was stirred at room temperature for 30 min, and the solvent was distilled off. The crude product was purified via reverse phase HPLC 40% to 80% MeOH in water with 0.1% NH$_4$OH to afford (S)-5-amino-N-(4-(3-aminopiperidin-1-yl)pyridin-3-yl)-2-(2-fluorophenyl)thiazole-4-carboxamide as a white solid (200 mg, 78%). $^1$H NMR (400 MHz, DMSO) δ 9.37 (s, 1H), 8.19 (ddd, J=9.5, 7.9, 3.5, 2H), 7.62 (s, 2H), 7.48 (ddd, J=7.1, 6.3, 1.7, 1H), 7.38 (ddd, J=12.5, 10.0, 4.3, 2H), 7.15 (d, J=5.3, 1H), 3.15 (dd, J=17.4, 8.0, 1H), 3.00 (dd, J=9.6, 4.6, 2H), 2.70-2.58 (m, 1H), 2.47-2.38 (m, 1H), 1.95-1.65 (m, 3H), 1.18 (td, J=15.3, 4.2, 1H); ESIMS m/z=413.1 (M+1).

Example 2

(S)-5-amino-N-(4-(3-aminopiperidin-1-yl)pyridin-3-yl)-2-(2-chlorophenyl)thiazole-4-carboxamide

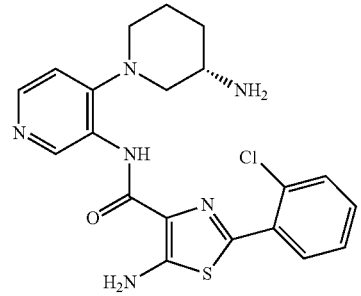 [SMILES: Nc1sc(-c2ccccc2Cl)nc1C(=O)Nc1cnccc1N1CCC[C@H](N)C1]

Following the procedures as described in EXAMPLE 1 and starting with 5-(tert-butoxycarbonylamino)-2-(2-chlorophenyl)thiazole-4-carboxylic acid, the title compound was obtained as a white solid (16.3 mg, 27%). $^1$H NMR (400 MHz, DMSO) δ 9.36 (s, 1H), 8.21 (t, J=6.5, 2H), 7.69-7.53 (m, 2H), 7.53-7.40 (m, 2H), 7.13 (d, J=5.3, 1H), 3.14 (d, J=11.4, 1H), 3.00 (d, J=9.3, 2H), 2.72-2.59 (m, 1H), 2.56-2.39 (m, 1H), 1.93-1.63 (m, 2H), 1.27-1.12 (m, 2H); ESIMS m/z=429.1 (M+1).

Example 3

(S)-5-amino-N-(4-(3-aminopiperidin-1-yl)pyridin-3-yl)-2-(2,6-difluorophenyl)thiazole-4-carboxamide

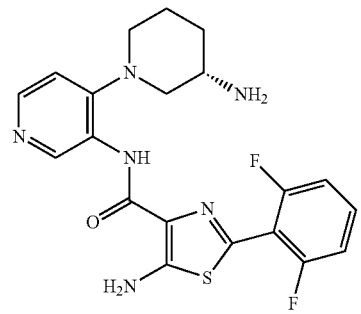 [SMILES: Nc1sc(-c2c(F)cccc2F)nc1C(=O)Nc1cnccc1N1CCC[C@H](N)C1]

Following the procedures as described in EXAMPLE 1 and starting with 5-(tert-butoxycarbonylamino)-2-(2,6-difluorophenyl)thiazole-4-carboxylic acid, the title compound was obtained as a white solid (12.4 mg, 23%). $^1$H NMR (400 MHz, DMSO) δ 9.37 (s, 1H), 8.32 (s, 0H), 8.21 (d, J=5.2, 1H), 7.65 (s, 1H), 7.54 (dt, J=14.7, 7.3, 1H), 7.28 (t, J=8.8, 2H), 7.12 (d, J=5.3, 1H), 3.11 (d, J=10.3, 1H), 2.97 (t, J=13.7, 2H), 2.64-2.54 (m, 1H), 2.47-2.38 (m, 1H), 1.86 (t, J=16.9, 1H), 1.72 (s, 2H), 1.18 (d, J=19.1, 1H). ESIMS m/z=431.1 (M+1).

Example 4

(S)-5-amino-N-(4-(3-aminopiperidin-1-yl)pyridin-3-yl)-2-(5-bromo-2-fluorophenyl)thiazole-4-carboxamide

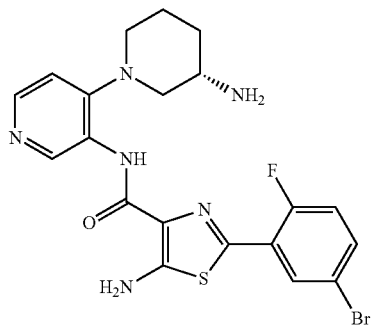

Following the procedures as described in EXAMPLE 1 and starting with 5-(tert-butoxycarbonylamino)-2-(5-bromo-2-fluorophenyl)thiazole-4-carboxylic acid, the title compound was obtained as a white solid (21.6 mg, 37%). $^1$H NMR (400 MHz, DMSO) δ 9.33 (s, 1H), 8.22 (d, J=5.3, 1H), 8.12 (dd, J=18.6, 10.2, 1H), 7.82-7.52 (m, 4H), 7.13 (d, J=5.3, 1H), 3.13 (d, J=10.6, 1H), 3.01 (dd, J=16.0, 10.9, 2H), 2.67 (t, J=10.0, 2H), 1.98-1.62 (m, 3H), 1.32-1.11 (m, 1H); ESIMS m/z=493.1 (M+2).

Example 5

(S)-5-amino-N-(4-(3-aminopiperidin-1-yl)pyridin-3-yl)-2-(5-bromo-2-chlorophenyl)thiazole-4-carboxamide

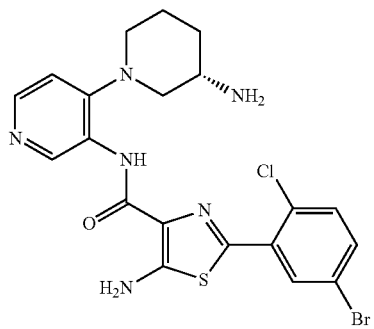 [SMILES: Nc1sc(-c2cc(Br)ccc2Cl)nc1C(=O)Nc1cnccc1N1CCC[C@H](N)C1]

Following the procedures as described in EXAMPLE 1 and starting with 5-(tert-butoxycarbonylamino)-2-(5-bromo-2-chlorophenyl)thiazole-4-carboxylic acid, the title compound was obtained as a white solid (2.1 mg, 3.5%). $^1$H NMR (400 MHz, DMSO) δ 9.49 (s, 1H), 9.19 (s, 1H), 8.56 (d, J=2.1, 1H), 8.31 (d, J=5.7, 1H), 7.97 (s, 3H), 7.71 (s, 2H), 7.60 (dt, J=22.2, 5.5, 2H), 7.28-7.15 (m, 1H), 7.01 (d, J=51.1, 1H), 3.33 (s, 3H), 2.99 (s, 2H), 2.06 (s, 1H), 1.91 (s, 1H), 1.77 (d, J=12.7, 1H), 1.59 (d, J=9.3, 1H). ESIMS m/z=509.1 (M+2).

Example 6

(S)-5-amino-N-(4-(3-aminopiperidin-1-yl)pyridin-3-yl)-2-(3-bromophenyl)thiazole-4-carboxamide

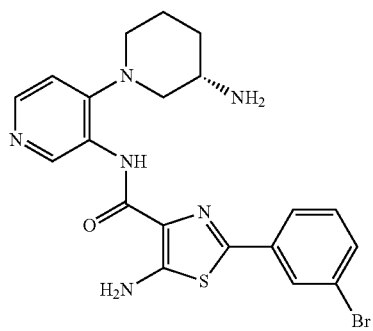 [SMILES: Nc1sc(-c2cccc(Br)c2)nc1C(=O)Nc1cnccc1N1CCC[C@H](N)C1]

Following the procedures as described in EXAMPLE 1 and starting with 5-(tert-butoxycarbonylamino)-2-(3-bromophenyl)thiazole-4-carboxylic acid, the title compound was obtained as a white solid (19.2 mg, 32%). $^1$H NMR (400 MHz, DMSO) δ 9.41 (s, 1H), 8.22 (d, J=5.2, 1H), 8.12 (s, 1H), 7.65 (dd, J=30.5, 7.9, 4H), 7.43 (t, J=7.9, 1H), 7.15 (d, J=5.3, 1H), 3.18-2.98 (m, 2H), 2.72-2.56 (m, 2H), 2.42 (t, J=10.0, 1H), 2.01 (d, J=12.2, 1H), 1.92-1.77 (m, 2H), 1.20 (d, J=7.0, 1H). ESIMS m/z=475.1 (M+2).

Example 7

(S)-5-amino-N-(4-(3-aminopiperidin-1-yl)pyridin-3-yl)-2-phenylthiazole-4-carboxamide

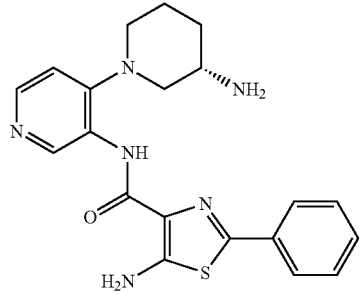 [SMILES: Nc1sc(-c2ccccc2)nc1C(=O)Nc1cnccc1N1CCC[C@H](N)C1]

Following the procedures as described in EXAMPLE 1 and starting with 5-(tert-butoxycarbonylamino)-2-phenylthiazole-4-carboxylic acid, the title compound was obtained as a white solid (3 mg, 4.9%). ESIMS m/z=395.1 (M+1).

Example 8

(S)-5-amino-N-(4-(3-aminopiperidin-1-yl)pyridin-3-yl)-2-methylthiazole-4-carboxamide

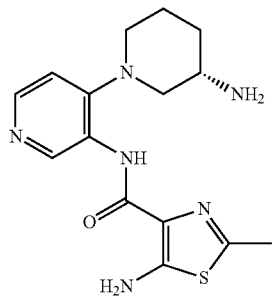

Following the procedures as described in EXAMPLE 1 and starting with 5-(tert-butoxycarbonylamino)-2-methylthiazole-4-carboxylic acid, the title compound was obtained as a white solid (5.3 mg, 8.2%). $^1$H NMR (400 MHz, DMSO) δ 9.32 (s, 1H), 8.29 (s, 1H), 8.18 (d, J=5.3, 1H), 7.23 (d, J=11.3, 2H), 7.08 (d, J=5.3, 1H), 3.19-2.93 (m, 5H), 2.66 (dd, J=10.5, 8.7, 1H), 2.47 (s, 3H), 1.81 (dddd, J=24.0, 20.5, 13.2, 7.1, 3H), 1.41-1.17 (m, 1H). ESIMS m/z=333.1 (M+1).

Example 9

(S)-5-amino-N-(4-(3-aminopiperidin-1-yl)pyridin-3-yl)-2-(pyridin-2-yl)thiazole-4-carboxamide

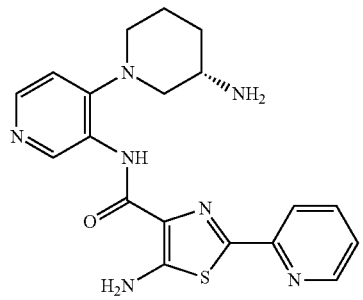 [SMILES: Nc1sc(-c2ccccn2)nc1C(=O)Nc1cnccc1N1CCC[C@H](N)C1]

Following the procedures as described in EXAMPLE 1 and starting with 5-(tert-butoxycarbonylamino)-2-(pyridin-2-yl)thiazole-4-carboxylic acid, the title compound was obtained as a white solid (18.5 mg, 30%). $^1$H NMR (400 MHz, DMSO) δ 9.34 (s, 1H), 8.57 (d, J=4.7, 1H), 8.35 (s, 0H), 8.22 (d, J=5.3, 1H), 8.03 (d, J=8.0, 1H), 7.95 (td, J=7.7, 1.6, 1H), 7.72 (s, 2H), 7.41 (dd, J=6.3, 5.0, 1H), 7.13 (d, J=5.3, 1H), 3.20-2.94

(m, 3H), 2.76-2.61 (m, 2H), 2.00-1.70 (m, 3H), 1.25 (dd, J=22.2, 11.6, 1H). ESIMS m/z=396.1 (M+1).

Example 10

(S)-5-amino-N-(4-(3-aminopiperidin-1-yl)pyridin-3-yl)thiazole-4-carboxamide

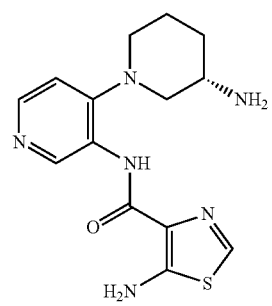 [SMILES: Nc1scnc1C(=O)Nc1cnccc1N1CCC[C@H](N)C1]

Following the procedures as described in EXAMPLE 1 and starting with 5-(tert-butoxycarbonylamino)thiazole-4-carboxylic acid, the title compound was obtained as a white solid (19.4 mg, 39%). $^1$H NMR (400 MHz, DMSO) δ 9.30 (s, 1H), 8.19 (d, J=5.3, 1H), 8.11 (s, 1H), 7.37 (s, 2H), 7.08 (d, J=5.3, 1H), 3.11 (d, J=11.1, 2H), 3.04-2.88 (m, 3H), 2.63 (ddd, J=13.9, 9.6, 2.3, 2H), 2.42 (dd, J=11.0, 9.1, 1H), 1.88 (dd, J=9.3, 4.8, 1H), 1.83-1.61 (m, 2H), 1.19 (td, J=14.2, 4.2, 1H). ESIMS m/z=319.1 (M+1).

Example 11

(S)-5-amino-N-(4-(3-aminopiperidin-1-yl)pyridin-3-yl)-2-(pyridin-3-yl)thiazole-4-carboxamide

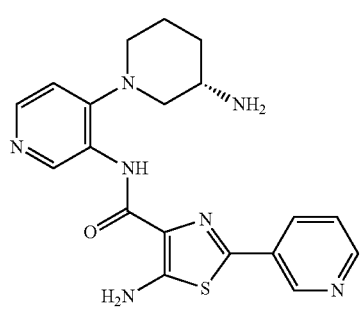 [SMILES: Nc1sc(-c2cccnc2)nc1C(=O)Nc1cnccc1N1CCC[C@H](N)C1]

Following the procedures as described in EXAMPLE 1 and starting with 5-(tert-butoxycarbonylamino)-2-(pyridin-3-yl)thiazole-4-carboxylic acid, the title compound was obtained as a white solid (7.5 mg, 12%). $^1$H NMR (400 MHz, DMSO) δ 9.34 (s, 1H), 9.04 (d, J=2.2, 1H), 8.60 (dd, J=4.8, 1.4, 1H), 8.22 (d, J=5.2, 1H), 8.19-8.11 (m, 1H), 7.69 (s, 2H), 7.52 (dd, J=8.0, 4.8, 1H), 7.13 (d, J=5.3, 1H), 3.20-2.92 (m, 4H), 2.75-

2.60 (m, 1H), 2.45 (dd, J=11.0, 9.2, 2H), 1.99-1.63 (m, 1H), 1.21 (td, J=14.3, 4.1, 1H). ESIMS m/z=396.1 (M+1).

Example 12

(S)-5-amino-N-(4-(3-aminopiperidin-1-yl)pyridin-3-yl)-2-(4-chlorophenyl)thiazole-4-carboxamide

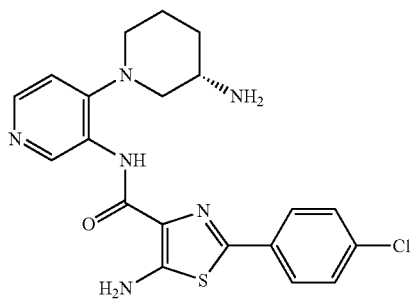 [SMILES: Nc1sc(-c2ccc(Cl)cc2)nc1C(=O)Nc1cnccc1N1CCC[C@H](N)C1]

Following the procedures as described in EXAMPLE 1 and starting with 5-(tert-butoxycarbonylamino)-2-(4-chlorophenyl)thiazole-4-carboxylic acid, the title compound was obtained as a white solid (21.3 mg, 32%). $^1$H NMR (400 MHz, DMSO) δ 9.35 (s, 1H), 8.35-8.17 (m, 1H), 7.83 (d, J=8.6, 2H), 7.65 (s, 1H), 7.56 (d, J=8.6, 2H), 7.13 (d, J=5.3, 1H), 3.07 (ddd, J=37.6, 28.3, 11.1, 4H), 2.67 (t, J=9.8, 1H), 2.33 (s, 0H), 1.82 (ddd, J=38.8, 30.3, 11.9, 3H), 1.25 (d, J=8.3, 1H). ESIMS m/z=429.1 (M+1).

Example 13

(S)-5-amino-N-(4-(3-aminopiperidin-1-yl)pyridin-3-yl)-2-(3-chlorophenyl)thiazole-4-carboxamide

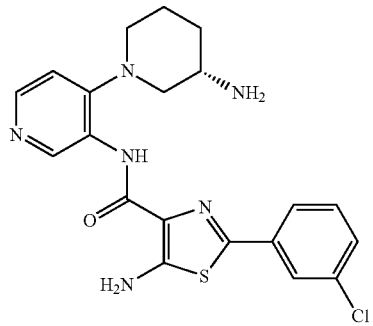

Following the procedures as described in EXAMPLE 1 and starting with 5-(tert-butoxycarbonylamino)-2-(3-chlorophenyl)thiazole-4-carboxylic acid, the title compoundn was obtained as a white solid (21.0 mg, 31%). $^1$H NMR (400 MHz, DMSO) δ 9.36 (d, J=24.2, 1H), 8.22 (d, J=5.2, 1H), 7.96 (s, 1H), 7.84-7.60 (m, 2H), 7.58-7.42 (m, 2H), 7.15 (d, J=5.3, 1H), 3.22-2.95 (m, 4H), 2.75-2.59 (m, 1H), 1.97 (d, J=12.9, 1H), 1.94-1.70 (m, 2H), 1.32-1.11 (m, 1H). ESIMS m/z=429.1 (M+1).

Example 14

5-amino-2-phenyl-N-(pyridin-3-yl)thiazole-4-carboxamide

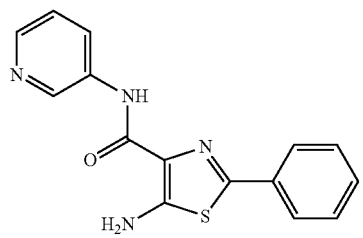 [SMILES: Nc1sc(-c2ccccc2)nc1C(=O)Nc1cccnc1]

Following the procedures as described in EXAMPLE 1 and starting with 5-(tert-butoxycarbonylamino)-2-phenylthiazole-4-carboxylic acid and 3-aminopyridine, the title compound was obtained as a white solid (21.0 mg, 42%). $^1$H NMR (400 MHz, DMSO) δ 9.78 (s, 1H), 8.99 (d, J=2.4, 1H), 8.30-8.18 (m, 2H), 7.95-7.88 (m, 2H), 7.59 (s, 2H), 7.53-7.32 (m, 4H). ESIMS m/z=297.1 (M+1).

Example 15

(S)-5-amino-N-(4-(3-aminopiperidin-1-yl)pyridin-3-yl)-2-(trifluoromethoxy)phenyl)thiazole-4-carboxamide

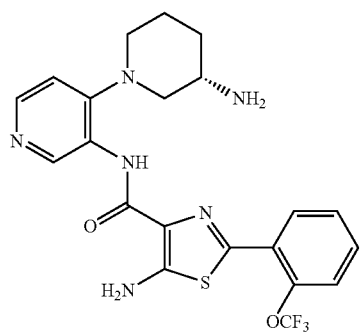 [SMILES: Nc1sc(-c2ccccc2OC(F)(F)F)nc1C(=O)Nc1cnccc1N1CCC[C@H](N)C1]

Following the procedures as described in EXAMPLE 1 and starting with 5-(tert-butoxycarbonylamino)-2-(2-(trifluoromethoxy)phenyl)thiazole-4-carboxylic acid, the title compound was obtained as a white solid (12.9 mg, 16%). $^1$H NMR (400 MHz, DMSO) δ 9.34 (s, 1H), 8.31 (dd, J=7.7, 2.2, 1H), 8.22 (d, J=5.3, 1H), 7.79-7.47 (m, 5H), 7.14 (d, J=5.3, 1H), 3.13 (d, J=11.2, 1H), 3.00 (dd, J=16.1, 6.8, 2H), 2.73-2.58 (m, 1H), 2.42 (dd, J=10.9, 9.2, 1H), 1.99-1.61 (m, 3H), 1.17 (td, J=15.0, 4.4, 1H). ESIMS m/z=479.1 (M+1).

Example 16

(S)-5-amino-N-(4-(3-aminopiperidin-1-yl)pyridin-3-yl)-2-tert-butylthiazole-4-carboxamide

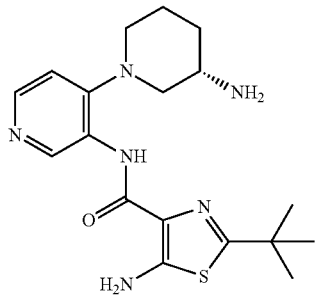

Following the procedures as described in EXAMPLE 1 and starting with 5-(tert-butoxycarbonylamino)-2-tert-butylthiazole-4-carboxylic acid, the title compound was obtained as a white solid (21.0 mg, 34%). $^1$H NMR (400 MHz, DMSO) δ 9.40 (s, 1H), 9.21 (s, 1H), 8.19 (d, J=5.2, 1H), 7.28 (s, 2H), 7.11 (d, J=5.3, 1H), 3.10 (d, J=10.7, 2H), 3.07-2.88 (m, 1H), 2.69-2.54 (m, 1H), 2.47-2.25 (m, 1H), 2.00-1.61 (m, 3H), 1.34 (s, 9H), 1.21 (ddd, J=23.2, 10.9, 3.8, 1H). ESIMS m/z=375.1 (M+1).

Example 17

5-amino-N-(4-chloropyridin-3-yl)-2-(2,6-difluorophenyl)thiazole-4-carboxamide

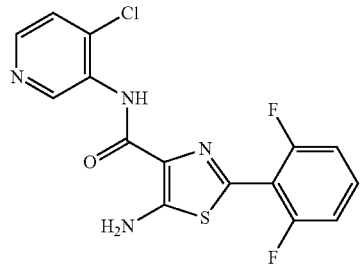 [SMILES: Nc1sc(-c2c(F)cccc2F)nc1C(=O)Nc1cnccc1Cl]

Following the procedures as described in EXAMPLE 1 and starting with 5-(tert-butoxycarbonylamino)-2-(2,6-difluorophenyl)thiazole-4-carboxylic acid and 3-amino-4-fluoropyridine, the title compound was obtained as a white solid (10 mg, 19%). $^1$H NMR$^1$H NMR (400 MHz, DMSO) δ 9.46 (s, 1H), 9.41 (s, 1H), 8.30 (d, J=5.2, 1H), 7.71 (s, 2H), 7.65 (d, J=5.2, 1H), 7.54 (dq, J=8.3, 6.4, 1H), 7.37-7.19 (m, 2H). ESIMS m/z=367.0 (M+1).

Example 18

(S)-5-amino-N-(4-(3-aminopiperidin-1-yl)pyridin-3-yl)-2-(5-(dimethylcarbamoyl)-2-fluorophenyl)thiazole-4-carboxamide

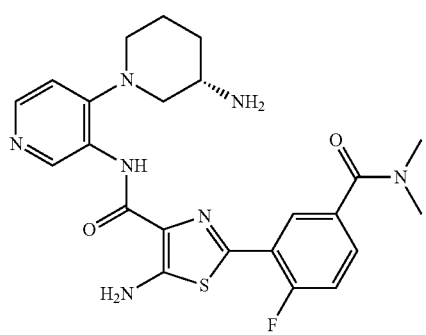 [SMILES: CN(C)C(=O)c1ccc(F)c(-c2nc(C(=O)Nc3cnccc3N3CCC[C@H](N)C3)c(N)s2)c1]

Following the procedures as described in EXAMPLE 1 and starting with 5-(tert-butoxycarbonylamino)-2-(5-(dimethyl carbamoyl)-2-fluorophenyl)thiazole-4-carboxylic acid, the title compound was obtained as a white solid (16.3 mg, 28%). $^1$H NMR (400 MHz, DMSO) δ 9.36 (s, 1H), 8.27 (s, 1H), 8.25-8.17 (m, 2H), 7.65 (s, 2H), 7.53-7.40 (m, 2H), 7.14 (d, J=5.3, 1H), 3.08-2.86 (m, 9H), 2.67 (q, J=9.1, 1H), 2.48-2.38 (m, 1H), 1.95-1.61 (m, 3H), 1.29-1.11 (m, 1H). ESIMS m/z=484.1 (M+1).

Example 19

(S)-5-amino-N-(4-(3-aminopiperidin-1-yl)pyridin-3-yl)-2-(imidazo[1,2-a]pyridin-2-yl)thiazole-4-carboxamide

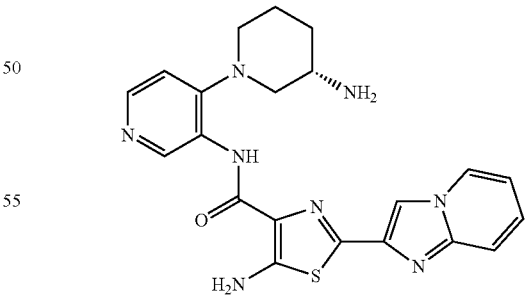

Following the procedures as described in EXAMPLE 1 and starting with 5-(tert-butoxycarbonylamino)-2-(imidazo[1,2-a]pyridin-2-yl)thiazole-4-carboxylic acid, the title compound was obtained as a white solid (22 mg, 42%). $^1$H NMR (400 MHz, DMSO) δ 9.35 (d, J=14.9, 1H), 8.66 (d, J=6.8, 1H), 8.25 (s, 1H), 8.21 (d, J=5.2, 1H), 7.59 (t, J=9.1, 3H), 7.37-7.28 (m, 1H), 7.12 (d, J=5.3, 1H), 7.01-6.93 (m, 1H), 3.10 (ddd, J=41.8, 25.5, 11.2, 4H), 2.69 (dd, J=15.2, 6.0, 1H), 2.05-1.94 (m, 1H), 1.94-1.73 (m, 2H), 1.36-1.16 (m, 1H). ESIMS m/z=435.1 (M+1).

Example 20

(S)-5-amino-N-(4-(3-aminopiperidin-1-yl)pyridin-3-yl)-2-phenyl-1H-imidazole-4-carboxamide

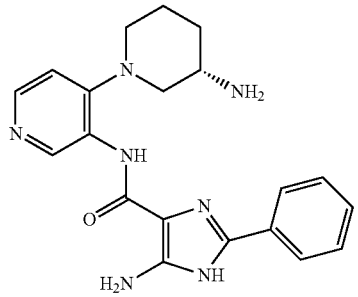 [SMILES: Nc1[nH]c(-c2ccccc2)nc1C(=O)Nc1cnccc1N1CCC[C@H](N)C1]

Following the procedures as described in EXAMPLE 1 and starting with 5-(tert-butoxycarbonylamino)-2-phenyl-1H-imidazole-4-carboxylic acid, the title compound was obtained as a white solid (6 mg, 10%). $^1$H NMR (400 MHz, DMSO) δ 9.33 (s, 1H), 8.24-8.13 (m, 1H), 7.89 (d, J=7.3, 2H), 7.45 (t, J=7.7, 2H), 7.34 (t, J=7.3, 1H), 7.10 (d, J=5.3, 1H), 5.93 (s, 2H), 3.02 (d, J=11.6, 2H), 2.71 (q, J=8.9, 3H), 1.92 (t, J=25.0, 3H), 1.47 (s, 1H). ESIMS m/z=378.2 (M+1).

Example 21

(S)-5-amino-N-(4-(3-aminopiperidin-1-yl)pyridin-3-yl)-2-((dimethylamino)methyl)thiazole-4-carboxamide

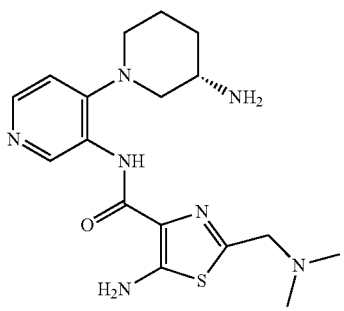 [SMILES: CN(C)Cc1nc(C(=O)Nc2cnccc2N2CCC[C@H](N)C2)c(N)s1]

Following the procedures as described in EXAMPLE 1 and starting with 5-(tert-butoxycarbonylamino)-2-((dimethylamino)methyl)thiazole-4-carboxylic acid, the title compound was obtained as a white solid (9.6 mg, 19%). $^1$H NMR (400 MHz, DMSO) δ 9.32 (d, J=20.2, 1H), 8.18 (d, J=5.3, 1H), 7.32 (s, 2H), 7.11 (t, J=12.8, 1H), 3.09 (d, J=10.9, 1H), 2.96 (dd, J=8.6, 4.3, 2H), 2.71-2.54 (m, 2H), 2.42 (dd, J=11.0, 8.9, 1H), 2.23 (d, J=16.3, 5H), 1.95-1.62 (m, 3H), 1.21 (td, J=13.6, 4.1, 1H). ESIMS m/z=376.1 (M+1).

Example 22

(S)-5-amino-N-(4-(3-aminopiperidin-1-yl)pyridin-3-yl)-2-(3-carbamoylphenyl)thiazole-4-carboxamide

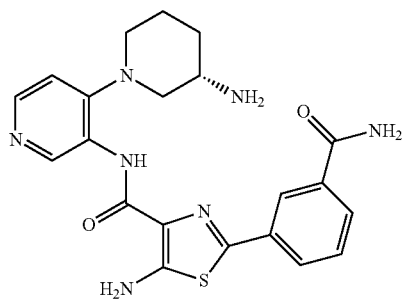 [SMILES: NC(=O)c1cccc(-c2nc(C(=O)Nc3cnccc3N3CCC[C@H](N)C3)c(N)s2)c1]

Following the procedures as described in EXAMPLE 1 and starting with 5-(tert-butoxycarbonylamino)-2-(3-carbamoylphenyl)thiazole-4-carboxylic acid, the title compound was obtained as a white solid (4.6 mg, 7.8%). ESIMS m/z=438.1 (M+1).

Example 23

(S)-5-amino-N-(4-(3-aminopiperidin-1-yl)pyridin-3-yl)-2-(5-chloro-2-fluorophenyl)thiazole-4-carboxamide

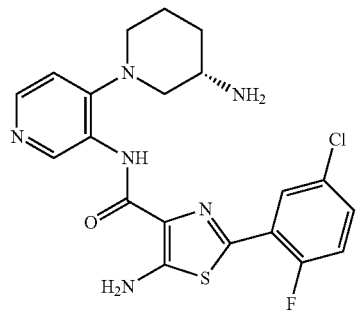 [SMILES: Nc1sc(-c2cc(Cl)ccc2F)nc1C(=O)Nc1cnccc1N1CCC[C@H](N)C1]

Following the procedures as described in EXAMPLE 1 and starting with 5-(tert-butoxycarbonylamino)-2-(5-chloro-2-fluorophenyl)thiazole-4-carboxylic acid, the title compound was obtained as a white solid (23 mg, 38%). $^1$H NMR (400 MHz, DMSO) δ 9.52 (s, 1H), 9.22 (s, 1H), 8.28 (dd, J=5.9, 3.5, 2H), 7.98 (s, 2H), 7.70 (s, 2H), 7.57-7.43 (m, 2H), 7.18 (d, J=5.4, 1H), 3.39 (s, 2H), 3.09 (d, J=12.4, 1H), 2.87 (t, J=10.1, 2H), 2.14-2.01 (m, 1H), 1.98-1.86 (m, 1H), 1.79 (dd, J=9.9, 3.7, 1H), 1.58 (dd, J=19.1, 9.4, 1H). ESIMS m/z=447.1 (M+1).

Example 24

5-amino-2-(2,6-difluorophenyl)-N-(4-(piperidin-1-yl)pyridin-3-yl)thiazole-4-carboxamide

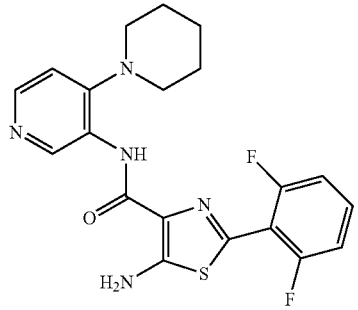 [SMILES: Nc1sc(-c2c(F)cccc2F)nc1C(=O)Nc1cnccc1N1CCCCC1]

Following the procedures as described in EXAMPLE 1 and starting with 4-(piperidin-1-yl)pyridin-3-amine and 5-(tert-butoxycarbonylamino)-2-(2,6-difluorophenyl)thiazole-4-carboxylic acid, the title compound was obtained as a white solid (36 mg, 34%). $^1$H NMR (400 MHz, DMSO) δ 9.40 (s, 1H), 9.35 (s, 1H), 8.21 (d, J=5.2, 1H), 7.67 (s, 2H), 7.53 (tt, J=8.3, 6.3, 1H), 7.29 (p, J=2.6, 2H), 7.13 (d, J=5.3, 1H), 2.90-2.80 (m, 4H), 1.76-1.64 (m, 4H), 1.51 (d, J=5.3, 2H). ESIMS m/z=416.1 (M+1).

Example 25

(S)-5-amino-N-(4-(3-aminopiperidin-1-yl)pyridin-3-yl)-2-(2,6-difluorophenyl)thiazole-4-carboxamide

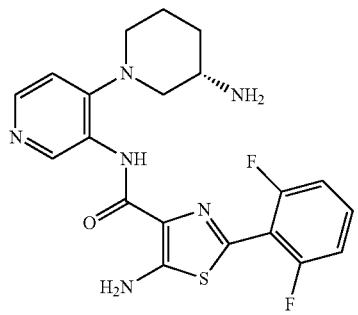 [SMILES: Nc1sc(-c2c(F)cccc2F)nc1C(=O)Nc1cnccc1N1CCC[C@H](N)C1]

Following the procedures as described in EXAMPLE 1 and starting with (R)-tert-butyl 1-(3-aminopyridin-4-yl)piperidin-3-ylcarbamate and 5-(tert-butoxycarbonylamino)-2-(2,6-difluorophenyl)thiazole-4-carboxylic acid, the title compound was obtained as a white solid (8 mg, 7.2%). $^1$H NMR (400 MHz, DMSO) δ 9.37 (s, 1H), 8.21 (d, J=5.2, 1H), 7.67 (s, 2H), 7.54 (ddd, J=14.7, 8.4, 6.3, 1H), 7.29 (t, J=8.9, 2H), 7.12 (d, J=5.3, 1H), 3.12 (d, J=7.6, 2H), 3.05-2.91 (m, 2H), 1.93-1.79 (m, 1H), 1.72 (s, 2H), 1.29-1.08 (m, 1H). ESIMS m/z=431.1 (M+1).

Example 26

(S)-5-amino-N-(4-(3-aminopiperidin-1-yl)pyridin-3-yl)-2-(3-ethoxy-2,6-difluorophenyl)thiazole-4-carboxamide

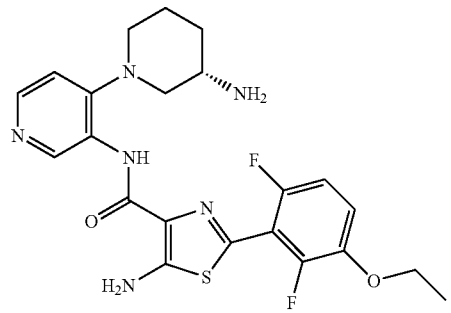 [SMILES: CCOc1ccc(F)c(-c2nc(C(=O)Nc3cnccc3N3CCC[C@H](N)C3)c(N)s2)c1F]

A septum sealed microwave tube was charged with (S)-tert-butyl 1-(3-(5-(tert-butoxycarbonylamino)-2-bromothiazole-4-carboxamido)pyridin-4-yl)piperidin-3-ylcarbamate (50 mg, 0.084 mmol), 2,6-difluoro-3-ethoxyphenyl-boronic acid (169 mg, 0.84 mmol), Pd(dppf)Cl$_2$ (13.6 mg, 0.016 mmol) 1M Na$_2$CO$_3$ (0.6 mL, 14.1 mmol) and acetonitrile (3 mL). The mixture was irradiated for 30 min at 120 C. Upon completion of the reaction, the solvent was distilled off and the crude material was dissolved in CH$_2$Cl$_2$ (5 mL) and transferred to a scintillation vial. TFA (0.77 g, 6.7 mmol) was added and the mixture was stirred at room temperature for 30 min. The solvent was distilled off and the crude product was purified via reverse phase HPLC 40% to 80% MeOH in water with 0.1% NH$_4$OH to afford (S)-5-amino-N-(4-(3-aminopiperidin-1-yl)pyridin-3-yl)-2-(3-ethoxy-2,6-difluorophenyl) thiazole-4-carboxamide as a white solid (4.8 mg, 12%). $^1$H NMR (400 MHz, DMSO) δ 9.35 (s, 1H), 8.27-8.16 (m, 1H), 7.66 (s, 2H), 7.28 (td, J=9.2, 5.1, 1H), 7.23-7.09 (m, 2H), 4.15 (q, J=7.0, 2H), 3.06 (dd, J=41.9, 10.8, 5H), 2.65 (dd, J=15.7, 5.1, 1H), 1.89 (d, J=10.1, 1H), 1.82-1.67 (m, 2H), 1.36 (t, J=7.0, 3H). ESIMS m/z=475.1 (M+1).

Example 27

(S)-5-amino-N-(4-(3-aminopiperidin-1-yl)pyridin-3-yl)-2-(3-propyloxy-2,6-difluorophenyl)thiazole-4-carboxamide

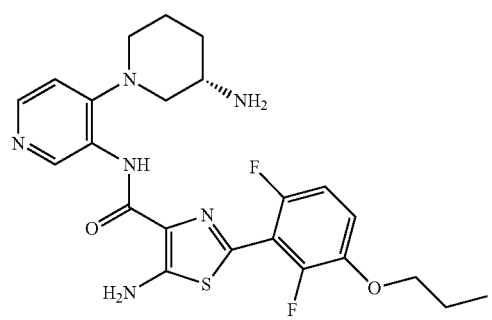 [SMILES: CCCOc1ccc(F)c(-c2nc(C(=O)Nc3cnccc3N3CCC[C@H](N)C3)c(N)s2)c1F]

Following the procedures as described in EXAMPLE 26 and starting with 2,6-difluoro-3-propyloxyphenyl-boronic acid, the title compound was obtained as a white solid (4.5 mg, 11%). ¹H NMR (400 MHz, DMSO) δ 9.38 (s, 1H), 8.30 (s, 1H), 8.21 (d, J=5.3, 1H), 7.66 (s, 2H), 7.28 (td, J=9.2, 5.2, 1H), 7.18 (t, J=9.8, 1H), 7.12 (d, J=5.3, 1H), 4.05 (t, J=6.4, 3H), 2.70-2.56 (m, 2H), 2.46-2.30 (m, 3H), 1.90-1.67 (m, 5H), 1.00 (t, J=7.4, 3H). ESIMS m/z=489.1 (M+1).

Example 28

(S)-5-amino-N-(4-(3-aminopiperidin-1-yl)pyridin-3-yl)-2-(3-butyloxy-2,6-difluorophenyl)thiazole-4-carboxamide

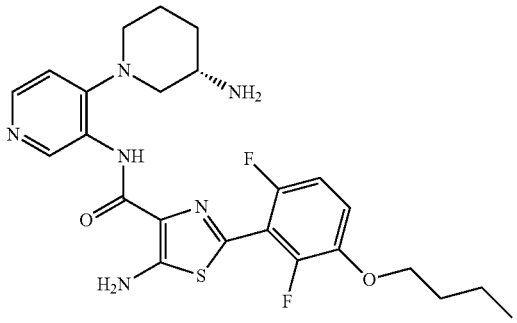 [SMILES: CCCCOc1ccc(F)c(-c2nc(C(=O)Nc3cnccc3N3CCC[C@H](N)C3)c(N)s2)c1F]

Following the procedures as described in EXAMPLE 26 and starting with 2,6-difluoro-3-butyloxyphenyl-boronic acid, the title compound was obtained as a white solid (3 mg, 7%). ESIMS m/z=503.2 (M+1).

Example 29

(S)-5-amino-N-(4-(3-aminopiperidin-1-yl)pyridin-3-yl)-2-(3-isopropyloxy-2,6-difluorophenyl)thiazole-4-carboxamide

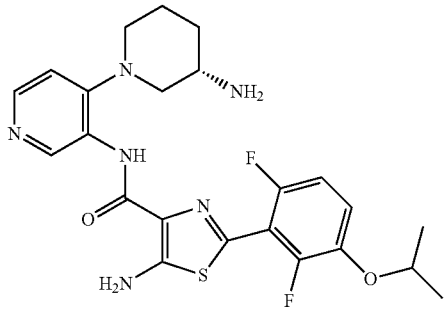 [SMILES: CC(C)Oc1ccc(F)c(-c2nc(C(=O)Nc3cnccc3N3CCC[C@H](N)C3)c(N)s2)c1F]

Following the procedures as described in EXAMPLE 26 and starting with 2,6-difluoro-3-isopropyloxyphenyl-boronic acid, the title compound was obtained as a white solid (6.5 mg, 16%). ¹H NMR (400 MHz, DMSO) δ 9.38 (s, 1H), 8.27 (s, 1H), 8.21 (d, J=5.3, 1H), 7.56 (dd, J=36.1, 25.2, 4H), 7.30 (td, J=9.2, 5.3, 1H), 7.17 (t, J=9.8, 1H), 7.12 (d, J=5.3, 1H), 4.60 (dt, J=12.2, 6.1, 1H), 3.06 (dd, J=51.1, 11.1, 3H), 2.70-2.56 (m, 1H), 1.84 (d, J=12.2, 1H), 1.73 (s, 2H), 1.30 (d, J=6.0, 6H), 1.18 (s, 2H). ESIMS m/z=489.1 (M+1).

Example 30

(S)-5-amino-N-(4-(3-aminopiperidin-1-yl)pyridin-3-yl)-2-(4-tolylthiazole)-4-carboxamide

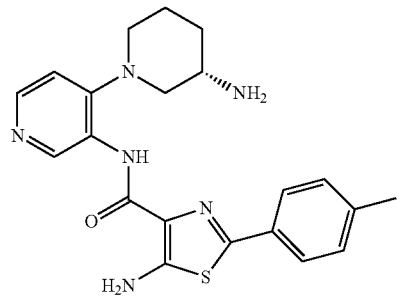 [SMILES: Cc1ccc(-c2nc(C(=O)Nc3cnccc3N3CCC[C@H](N)C3)c(N)s2)cc1]

Following the procedures as described in EXAMPLE 26 and starting with p-tolylboronic acid, the title compound was obtained as a white solid (3.7 mg, 11%). ¹H NMR (400 MHz, DMSO) δ 9.38 (s, 1H), 8.21 (d, J=5.2, 1H), 7.71 (d, J=8.2, 2H), 7.57 (s, 2H), 7.30 (d, J=8.0, 2H), 7.14 (d, J=5.3, 1H), 3.19-2.96 (m, 4H), 2.65 (dd, J=15.8, 5.1, 1H), 2.39-2.30 (m, 3H), 2.01-1.88 (m, 1H), 1.88-1.69 (m, 2H), 1.24 (d, J=7.7, 1H). ESIMS m/z=409.1 (M+1).

Example 31

(S)-5-amino-N-(4-(3-aminopiperidin-1-yl)pyridin-3-yl)-2-(3-tolylthiazole)-4-carboxamide

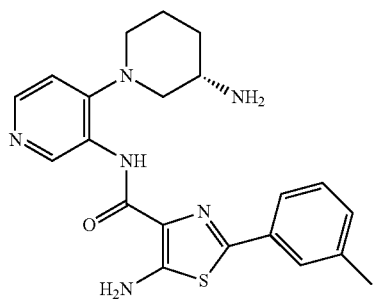 [SMILES: Cc1cccc(-c2nc(C(=O)Nc3cnccc3N3CCC[C@H](N)C3)c(N)s2)c1]

Following the procedures as described in EXAMPLE 26 and starting with m-tolylboronic acid, the title compound was obtained as a white solid (8.6 mg, 25%). ¹H NMR (400 MHz, DMSO) δ 9.42 (s, 1H), 8.22 (d, J=5.2, 1H), 7.72 (s, 1H), 7.61 (s, 2H), 7.54 (d, J=7.8, 1H), 7.36 (t, J=7.6, 1H), 7.25 (d, J=7.5, 1H), 7.15 (d, J=5.3, 1H), 3.20-2.97 (m, 4H), 2.72-2.58 (m, 1H), 2.41-2.33 (m, 3H), 1.93 (d, J=12.7, 1H), 1.82 (d, J=17.4, 2H), 1.33-1.13 (m, 1H). ESIMS m/z=409.1 (M+1).

Example 32

(S)-5-amino-N-(4-(3-aminopiperidin-1-yl)pyridin-3-yl)-2-(4-(3-ethylureido)phenyl)thiazole-4-carboxamide

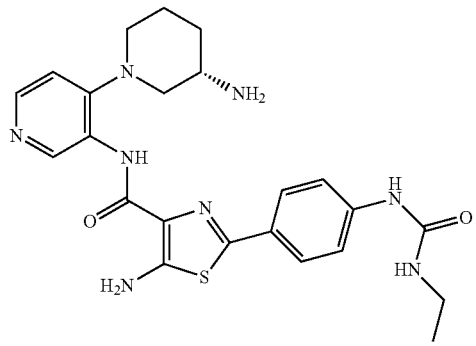 [SMILES: CCNC(=O)Nc1ccc(-c2nc(C(=O)Nc3cnccc3N3CCC[C@H](N)C3)c(N)s2)cc1]

Following the procedures as described in EXAMPLE 26 and starting with 4-(3-ethylureido)phenylboronic acid, the title compound was obtained as a white solid (9.3 mg, 23%). ¹H NMR (400 MHz, DMSO) δ 9.38 (s, 1H), 8.79 (s, 1H), 8.22 (d, J=5.2, 1H), 7.66 (t, J=11.4, 2H), 7.51 (d, J=8.7, 4H), 7.14 (d, J=5.3, 1H), 6.29 (t, J=5.6, 1H), 3.21-3.05 (m, 5H), 2.99 (t, J=14.7, 1H), 2.67 (dd, J=10.4, 6.6, 1H), 2.00-1.73 (m, 3H), 1.37-1.20 (m, 1H), 1.12-1.02 (m, 3H). ESIMS m/z=481.2 (M+1).

Example 33

(S)-5-amino-N-(4-(3-aminopiperidin-1-yl)pyridin-3-yl)-2-(pyridin-4-yl)thiazole-4-carboxamide

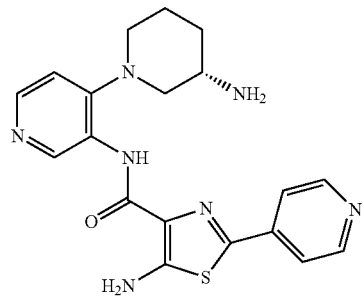 [SMILES: Nc1sc(-c2ccncc2)nc1C(=O)Nc1cnccc1N1CCC[C@H](N)C1]

Following the procedures as described in EXAMPLE 26 and starting with pyridin-4-ylboronic acid, the title compound was obtained as a white solid (9.6 mg, 29%). ¹H NMR (400 MHz, DMSO) δ 9.32 (s, 1H), 8.66 (dd, J=4.6, 1.5, 2H), 8.23 (d, J=5.3, 1H), 7.74 (dd, J=4.6, 1.6, 2H), 7.14 (d, J=5.3, 1H), 3.08 (ddd, J=32.9, 26.6, 11.3, 4H), 2.77-2.63 (m, 1H), 1.99-1.64 (m, 3H), 1.25 (d, J=10.3, 1H). ESIMS m/z=396.2 (M+1).

Example 34

(S)-5-amino-N-(4-(3-aminopiperidin-1-yl)pyridin-3-yl)-2-(2,6-difluoro-4-methoxyphenyl)thiazole-4-carboxamide

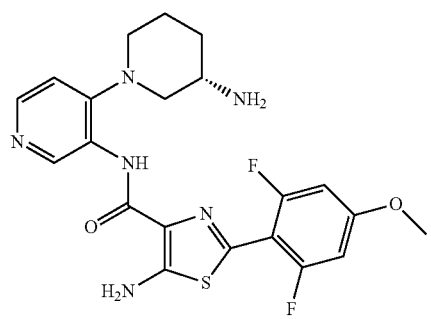 [SMILES: COc1cc(F)c(-c2nc(C(=O)Nc3cnccc3N3CCC[C@H](N)C3)c(N)s2)c(F)c1]

Following the procedures as described in EXAMPLE 26 and starting with 2,6-difluoro-4-methoxyphenyl-boronic acid, the title compound was obtained as a white solid (4.2 mg, 11%). ESIMS m/z=461.2 (M+1).

Example 35

(S)-5-amino-N-(4-(3-aminopiperidin-1-yl)pyridin-3-yl)-2-(2-fluoro-4-methoxyphenyl)thiazole-4-carboxamide

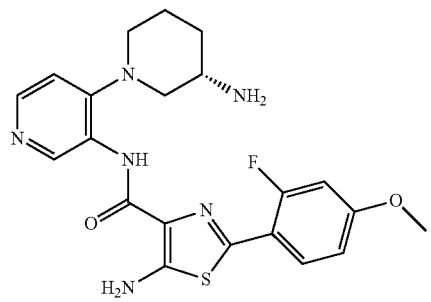 [SMILES: COc1ccc(-c2nc(C(=O)Nc3cnccc3N3CCC[C@H](N)C3)c(N)s2)c(F)c1]

Following the procedures as described in EXAMPLE 26 and starting with fluoro-4-methoxyphenyl-boronic acid, the title compound was obtained as a white solid (16.3 mg, 44%). ¹H NMR (400 MHz, DMSO) δ 9.36 (d, J=5.9, 1H), 8.21 (d, J=5.2, 1H), 8.06 (t, J=8.9, 1H), 7.51 (s, 2H), 7.13 (d, J=5.3, 1H), 7.07-6.93 (m, 2H), 3.85 (s, 3H), 3.12 (d, J=11.0, 1H), 3.05-2.94 (m, 2H), 2.64 (ddd, J=13.7, 8.4, 2.3, 1H), 2.42 (dd, J=10.9, 9.2, 1H), 1.97-1.65 (m, 3H), 1.26-1.12 (m, 1H). ESIMS m/z=443.1 (M+1).

Example 36

(S)-5-amino-N-(4-(3-aminopiperidin-1-yl)pyridin-3-yl)-2-isopropylthiazole-4-carboxamide

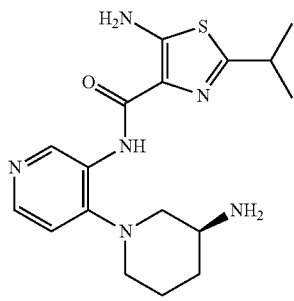

Following the procedures as described in EXAMPLE 1 and starting with 5-(tert-butoxycarbonylamino)-2-isopropylthiazole-4-carboxylic acid, the title compound was obtained as a white solid (17.0 mg, 26.4%). $^1$H NMR (400 MHz, DMSO) δ 9.39 (s, 1H), 8.18 (d, J=5.2, 1H), 7.26 (s, 2H), 7.10 (d, J=5.2, 1H), 3.08 (dd, J=13.7, 6.8, 2H), 3.00-2.93 (m, 2H), 2.59 (td, J=11.3, 3.0, 1H), 2.39 (dd, J=10.9, 9.2, 1H), 1.92-1.67 (m, 3H), 1.29 (d, J=6.9, 6H), 1.18 (dd, J=18.9, 10.9, 1H); ESIMS m/z=361.2 (M+1).

Example 37

(S)-5-amino-N-(4-(3-aminopiperidin-1-yl)pyridin-3-yl)-2-cyclohexylthiazole-4-carboxamide

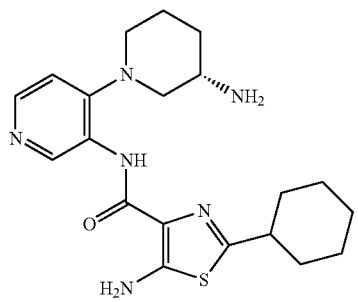 [SMILES: Nc1sc(C2CCCCC2)nc1C(=O)Nc1cnccc1N1CCC[C@H](N)C1]

Following the procedures as described in EXAMPLE 1 and starting with 5-(tert-butoxycarbonylamino)-2-cyclohexylthiazole-4-carboxylic acid, the title compound was obtained as a white solid (13.3 mg, 20.0%). $^1$H NMR (400 MHz, DMSO) δ 9.39 (s, 1H), 8.18 (d, J=5.2, 1H), 7.24 (s, 2H), 7.10 (d, J=5.3, 1H), 3.07 (d, J=11.2, 1H), 3.00-2.92 (m, 2H), 2.77 (tt, J=11.1, 3.7, 1H), 2.57 (dt, J=8.9, 7.0, 1H), 2.39 (dd, J=10.8, 9.3, 1H), 2.00 (d, J=10.7, 2H), 1.91-1.63 (m, 7H), 1.53-1.28 (m, 4H), 1.21 (ddd, J=30.3, 15.3, 6.6, 2H); ESIMS m/z=401.2 (M+1).

Example 38

(S)-5-amino-N-(4-(3-aminopiperidin-1-yl)pyridin-3-yl)-2-benzylthiazole-4-carboxamide

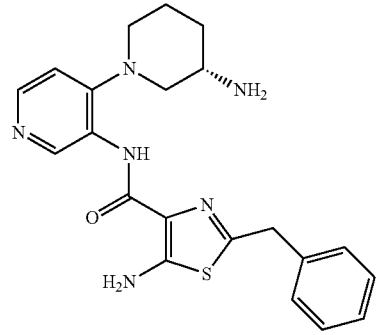 [SMILES: Nc1sc(Cc2ccccc2)nc1C(=O)Nc1cnccc1N1CCC[C@H](N)C1]

Following the procedures as described in EXAMPLE 1 and starting with 2-benzyl-5-(tert-butoxycarbonylamino)thiazole-4-carboxylic acid, the title compound was obtained as a white solid (7.1 mg, 16.0%). $^1$H NMR (400 MHz, DMSO) δ 9.28 (s, 1H), 8.11 (d, J=5.3, 1H), 7.31-7.25 (m, 4H), 7.21 (dd, J=12.0, 5.4, 3H), 7.01 (d, J=5.3, 1H), 4.05 (s, 2H), 3.01 (d, J=11.2, 1H), 2.92-2.77 (m, 2H), 2.51 (t, J=9.0, 1H), 2.35-2.28 (m, 1H), 1.83 (s, 1H), 1.67 (s, 1H), 1.59 (s, 1H), 1.17-1.04 (m, 2H); ESIMS m/z=409.1 (M+1).

Example 39

(S)-5-amino-N-(4-(3-aminopiperidin-1-yl)pyridin-3-yl)-2-(2-methoxyphenyl)thiazole-4-carboxamide

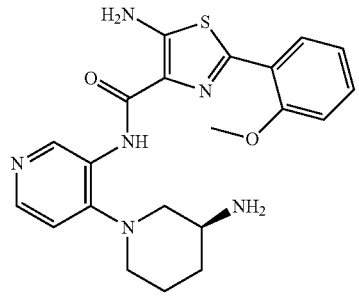 [SMILES: COc1ccccc1-c1nc(C(=O)Nc2cnccc2N2CCC[C@H](N)C2)c(N)s1]

Following the procedures as described in EXAMPLE 1 and starting with 5-(tert-butoxycarbonylamino)-2-(2-methoxyphenyl)thiazole-4-carboxylic acid, the title compound was obtained as a white solid (30.0 mg, 32.6%). ESIMS m/z=425.1 (M+1).

Example 40

(S)-5-amino-N-(4-(3-aminopiperidin-1-yl)pyridin-3-yl)-2-o-tolylthiazole-4-carboxamide

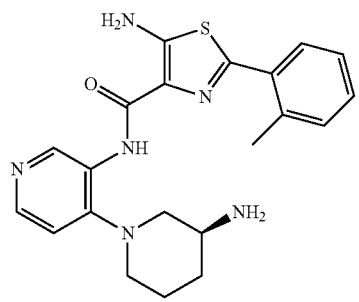 [SMILES: Cc1ccccc1-c1nc(C(=O)Nc2cnccc2N2CCC[C@H](N)C2)c(N)s1]

Following the procedures as described in EXAMPLE 1 and starting with 5-(tert-butoxycarbonylamino)-2-o-tolylthiazole-4-carboxylic acid, the title compound was obtained as a white solid (7.1 mg, 16.0%). $^1$H NMR (400 MHz, DMSO) δ 9.33 (s, 1H), 8.21 (d, J=5.3, 1H), 7.70-7.65 (m, 1H), 7.56 (s, 2H), 7.38-7.27 (m, 3H), 7.12 (d, J=5.3, 1H), 3.13 (d, J=7.7, 1H), 3.02 (d, J=11.9, 1H), 2.93-2.87 (m, 1H), 2.61 (d, J=13.6, 3H), 2.59 (s, 1H), 2.43-2.36 (m, 1H), 1.82 (d, J=13.1, 1H), 1.75-1.60 (m, 2H), 1.20-1.07 (m, 1H); ESIMS m/z=409.1 (M+1).

Example 41

(S)-5-amino-N-(4-(3-aminopiperidin-1-yl)pyridin-3-yl)-2-(2,5-difluorophenyl)thiazole-4-carboxamide

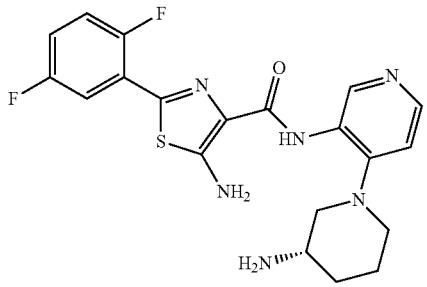 [SMILES: Nc1sc(-c2cc(F)ccc2F)nc1C(=O)Nc1cnccc1N1CCC[C@H](N)C1]

Following the procedures as described in EXAMPLE 1 and starting with 5-(tert-butoxycarbonylamino)-2-(2,5-difluorophenyl)thiazole-4-carboxylic acid, the title compound was obtained as a white solid (24.0 mg, 54.0%). $^1$H NMR (400 MHz, DMSO) δ 9.33 (s, 1H), 8.24-8.16 (m, 2H), 7.54 (d, J=36.3, 2H), 7.50 (s, 1H), 7.31 (td, J=8.5, 2.4, 1H), 7.13 (d, J=5.3, 1H), 3.14 (d, J=11.0, 1H), 3.05-2.94 (m, 2H), 2.66 (dd, J=15.7, 6.4, 1H), 1.91 (dd, J=12.6, 3.7, 1H), 1.80 (dd, J=16.5, 12.9, 1H), 1.76 (s, 1H), 1.22 (td, J=14.1, 4.3, 1H); ESIMS m/z=431.1 (M+1).

Example 42

(S)-5-amino-N-(4-(3-aminopiperidin-1-yl)pyridin-3-yl)-2-(2,4-difluorophenyl)thiazole-4-carboxamide

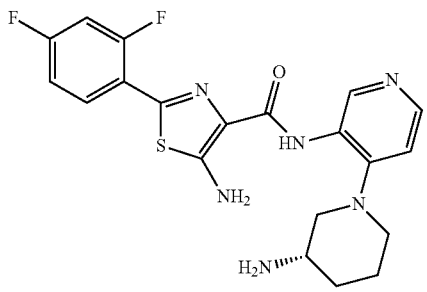 [SMILES: Nc1sc(-c2ccc(F)cc2F)nc1C(=O)Nc1cnccc1N1CCC[C@H](N)C1]

Following the procedures as described in EXAMPLE 1 and starting with 5-(tert-butoxycarbonylamino)-2-(2,4-difluorophenyl)thiazole-4-carboxylic acid, the title compound was obtained as a white solid (28.0 mg, 51.5%). $^1$H NMR (400 MHz, DMSO) δ 9.31 (s, 1H), 8.22 (d, J=5.3, 1H), 7.96 (ddd, J=9.2, 5.6, 3.3, 1H), 7.66 (s, 2H), 7.49-7.40 (m, 1H), 7.34-7.26 (m, 1H), 7.14 (d, J=5.3, 1H), 3.14 (d, J=11.2, 1H), 3.03 (dd, J=8.5, 4.2, 2H), 2.68 (dd, J=16.3, 6.1, 1H), 2.44 (dd, J=11.0, 9.2, 1H), 1.80 (ddd, J=34.8, 26.0, 13.5, 3H), 1.28-1.13 (m, 1H); ESIMS m/z=431.1 (M+1).

Example 43

(S)-5-amino-N-(4-(3-aminopiperidin-1-yl)pyridin-3-yl)-2-(2,3-difluorophenyl)thiazole-4-carboxamide

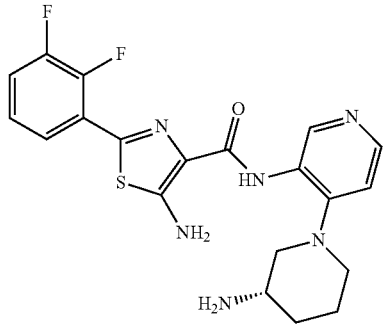 [SMILES: Nc1sc(-c2cccc(F)c2F)nc1C(=O)Nc1cnccc1N1CCC[C@H](N)C1]

Following the procedures as described in EXAMPLE 1 and starting with 5-(tert-butoxycarbonylamino)-2-(2,3-difluorophenyl)thiazole-4-carboxylic acid, the title compound was obtained as a white solid (70.6 mg, 41.0%). $^1$H NMR (400 MHz, DMSO) δ 9.33 (s, 1H), 8.22 (d, J=5.3, 1H), 7.94 (dd, J=8.0, 6.5, 1H), 7.68 (s, 2H), 7.50 (dd, J=16.8, 8.2, 1H), 7.35 (dd, J=12.6, 7.6, 1H), 7.14 (d, J=5.3, 1H), 3.13 (s, 1H), 3.08-2.96 (m, 2H), 2.69-2.62 (m, 1H), 2.46-2.41 (m, 1H), 1.93-1.69 (m, 3H), 1.28-1.15 (m, 1H); ESIMS m/z=431.1 (M+1).

Example 44

(S)-5-amino-N-(4-(3-aminopiperidin-1-yl)pyridin-3-yl)-2-(quinolin-7-yl)thiazole-4-carboxamide

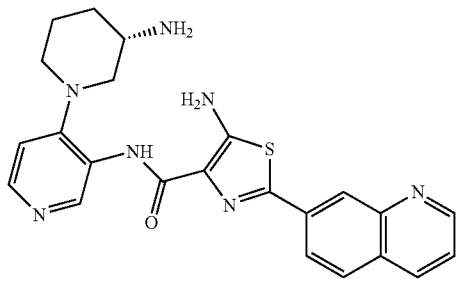 [SMILES: Nc1sc(-c2ccc3cccnc3c2)nc1C(=O)Nc1cnccc1N1CCC[C@H](N)C1]

Following the procedures as described in EXAMPLE 1 and starting with 5-(tert-butoxycarbonylamino)-2-(quinolin-6-yl)thiazole-4-carboxylic acid, the title compound was obtained as a white solid (10.6 mg, 11.9%). $^1$H NMR (400 MHz, DMSO) δ 9.34 (s, 1H), 8.97 (dd, J=4.2, 1.7, 1H), 8.40 (d, J=8.1, 1H), 8.33 (s, 1H), 8.24 (d, J=5.2, 1H), 8.12 (dt, J=16.6, 5.1, 2H), 7.74 (s, 2H), 7.57 (dd, J=8.2, 4.2, 1H), 7.16

(d, J=5.3, 1H), 3.05 (d, J=11.5, 1H), 2.76 (t, J=9.3, 1H), 2.61 (t, J=10.2, 1H), 2.00 (s, 1H), 1.89 (s, 2H), 1.37 (s, 1H); ESIMS m/z=446.1 (M+1).

Example 45

(S)-N-(4-(3-aminopiperidin-1-yl)pyridin-3-yl)-2-(2-fluorophenyl)thiazole-4-carboxamide

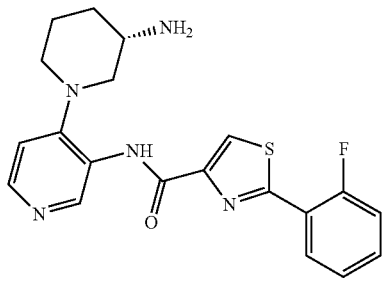 [SMILES: N[C@H]1CCCN(c2ccncc2NC(=O)c2csc(-c3ccccc3F)n2)C1]

Step 1: (S)-tert-butyl 1-(3-(2-bromothiazole-4-carboxamido)pyridin-4-yl)piperidin-3-ylcarbamate

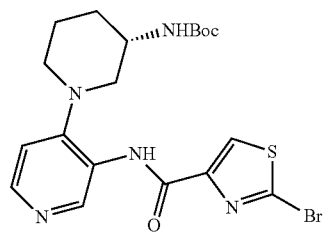 [SMILES: CC(C)(C)OC(=O)N[C@H]1CCCN(c2ccncc2NC(=O)c2csc(Br)n2)C1]

To a mixture of (S)-tert-butyl 1-(3-aminopyridin-4-yl)piperidin-3-ylcarbamate (1.04 g, 5.00 mmol) and 2-bromothiazole-4-carboxylic acid (1.46 g, 5.00 mmol) in Methylene chloride (10 mL, 200 mmol) was added N,N-Diisopropylethylamine (3.48 mL, 20.0 mmol) and N,N,N',N'-Tetramethyl-O-(7-azabenzotriazol-1-yl)uronium Hexafluorophosphate (2.28 g, 6.00 mmol). The reaction mixture was stirred at room temperature overnight. The reaction mixture was then concentrated and the residue was purified on silica eluting with 0 to 5% MeOH in DCM with 1% NH₄OH (2.41 g, 99.9%). ESIMS m/z=484.1 (M+1).

Step 2: (S)-tert-butyl 1-(3-(2-(2-fluorophenyl)thiazole-4-carboxamido)pyridin-4-yl)piperidin-3-ylcarbamate

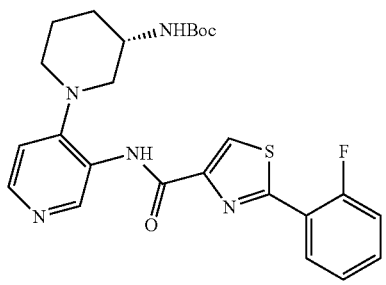 [SMILES: CC(C)(C)OC(=O)N[C@H]1CCCN(c2ccncc2NC(=O)c2csc(-c3ccccc3F)n2)C1]

In a microwave safe sealed tube was charged a mixture of ((S)-tert-butyl 1-(3-(2-bromothiazole-4-carboxamido)pyridin-4-yl)piperidin-3-ylcarbamate (96.5 mg, 0.2 mmol), 2-Fluorophenylboronic acid (33.6 mg, 0.24 mmol), 1,1'-Bis(diphenylphosphino)ferrocene palladium (II) chloride (81.7 mg, 0.1 mmol), 1.00 M of Potassium acetate in Water (0.3 mL, 0.3 mmol), 1.00 M of Sodium carbonate in Water (0.3 mL, 0.3 mmol) in acetonitrile (5 mL). The mixture was irradiated at 300 W 110° C. for 15 minutes. The reaction mixture was then concentrated and the residue was purified on silica eluting with 0 to 5% MeOH in DCM with 1% NH₄OH (90.0 mg, 90.4%). ESIMS m/z=498.2 (M+1).

Step 3: (S)-N-(4-(3-aminopiperidin-1-yl)pyridin-3-yl)-2-(2-fluorophenyl)thiazole-4-carboxamide

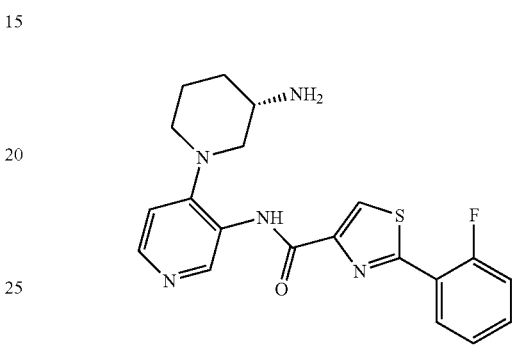

To a solution of (S)-tert-butyl 1-(3-(2-(2-fluorophenyl)thiazole-4-carboxamido)pyridin-4-yl)piperidin-3-ylcarbamate (100 mg, 0.2 mmol) in 1,4-Dioxane (6 mL) was added 4.0 M of Hydrogen chloride in 1,4-Dioxane (3 mL). The resulting mixture was stirred at room temperature overnight. The mixture was concentrated and the residue was purified by reverse phase HPLC. (10.7 mg, 10.0%). ¹H NMR (400 MHz, DMSO) δ 9.24 (s, 1H), 8.68 (s, 1H), 8.40 (t, J=7.1, 1H), 8.32-8.26 (m, 2H), 7.67-7.61 (m, 1H), 7.53-7.43 (m, 2H), 7.16 (d, J=5.3, 1H), 3.04 (s, 2H), 2.75 (t, J=9.5, 1H), 2.61-2.54 (m, 1H), 1.92-1.86 (m, 1H), 1.81 (d, J=4.2, 1H), 1.73 (d, J=9.9, 1H), 1.33-1.23 (m, 1H); ESIMS m/z=398.1 (M+1).

Example 46

(S)-N-(4-(3-aminopiperidin-1-yl)pyridin-3-yl)-2-(2,6-difluorophenyl)thiazole-4-carboxamide

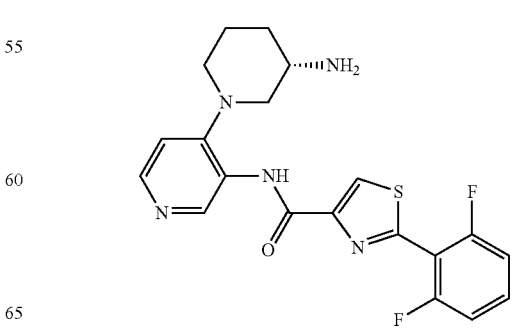

Step 1: (5)-tert-butyl 1-(3-(2-(2,6-difluorophenyl)thiazole-4-carboxamido)pyridin-4-yl)piperidin-3-ylcarbamate

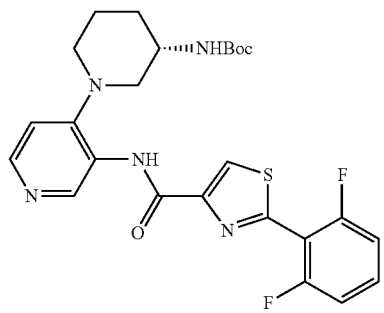 [SMILES: CC(C)(C)OC(=O)N[C@H]1CCCN(c2ccncc2NC(=O)c2csc(-c3c(F)cccc3F)n2)C1]

Following procedures described above in EXAMPLE 45 using 2-Fluorophenylboronic acid (94.7 mg, 0.60 mmol), the desired product (S)-tert-butyl 1-(3-(2-(2,6-difluorophenyl)thiazole-4-carboxamido)pyridin-4-yl)piperidin-3-ylcarbamate (15.7 mg, 15.2%) was obtained after silica gel purification. ESIMS m/z=516.2 (M+1).

Step 2: (S)-N-(4-(3-aminopiperidin-1-yl)pyridin-3-yl)-2-(2,6-difluorophenyl)thiazole-4-carboxamide

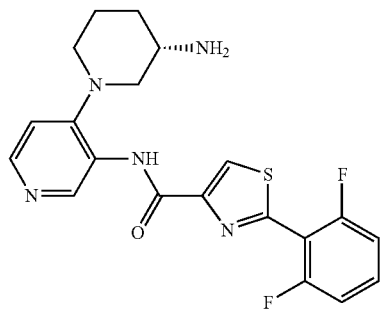 [SMILES: N[C@H]1CCCN(c2ccncc2NC(=O)c2csc(-c3c(F)cccc3F)n2)C1]

Following procedures described above in EXAMPLE 45 using (5)-tert-butyl 1-(3-(2-(2,6-difluorophenyl)thiazole-4-carboxamido)pyridin-4-yl)piperidin-3-ylcarbamate, the desired product (S)-N-(4-(3-aminopiperidin-1-yl)pyridin-3-yl)-2-(2,6-difluorophenyl)thiazole-4-carboxamide (0.7 mg, 6.0%) was obtained after reverse phase HPLC purification. $^1$H NMR (400 MHz, DMSO) δ 9.31 (s, 1H), 8.78 (d, J=8.5, 1H), 8.28 (d, J=5.3, 1H), 7.74-7.64 (m, 1H), 7.39 (t, J=8.8, 2H), 7.15 (d, J=5.3, 1H), 3.15 (d, J=7.6, 2H), 3.03 (d, J=11.8, 1H), 2.96 (dd, J=9.1, 4.5, 1H), 2.64 (dd, J=14.7, 5.8, 1H), 1.83 (dd, J=12.4, 4.0, 1H), 1.72 (dt, J=13.8, 6.9, 2H), 1.18 (dt, J=15.5, 10.0, 1H); ESIMS m/z=416.1 (M+1).

Example 47

(S)-N-(4-(3-aminopiperidin-1-yl)pyridin-3-yl)-2-(5-(dimethylcarbamoyl)-2-fluorophenyl)thiazole-4-carboxamide

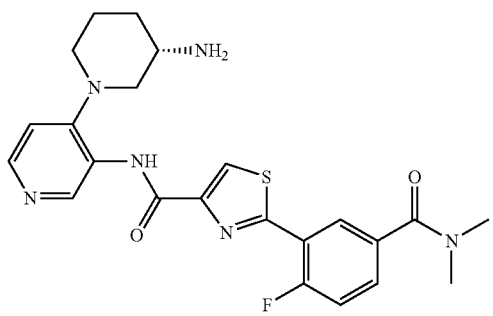 [SMILES: CN(C)C(=O)c1ccc(F)c(-c2nc(C(=O)Nc3cnccc3N3CCC[C@H](N)C3)cs2)c1]

Step 1: (5)-tert-butyl 1-(3-(2-(5-(dimethylcarbamoyl)-2-fluorophenyl)thiazole-4-carboxamido) pyridin-4-yl)piperidin-3-ylcarbamate

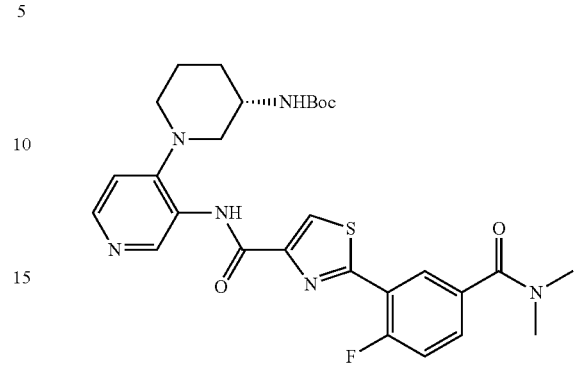

Following procedures described above in EXAMPLE 45 using 5-(dimethylcarbamoyl)-2-fluorophenylboronic acid (50.6 mg, 0.24 mmol), the desired product(S)-tert-butyl 1-(3-(2-(5-(dimethylcarbamoyl)-2-fluorophenyl)thiazole-4-carboxamido)pyridin-4-yl)piperidin-3-ylcarbamate (15.7 mg, 15.2%) was obtained after silica gel purification ESIMS m/z=569.3 (M+1).

Step 2: (S)-N-(4-(3-aminopiperidin-1-yl)pyridin-3-yl)-2-(5-(dimethylcarbamoyl)-2-fluorophenyl)thiazole-4-carboxamide

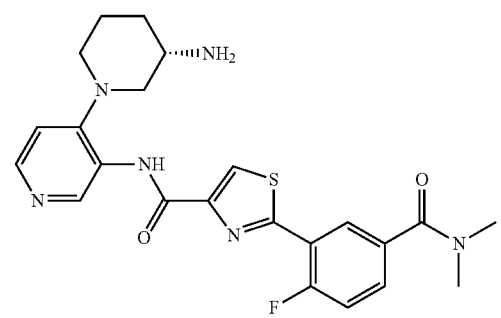 [SMILES: CN(C)C(=O)c1ccc(F)c(-c2nc(C(=O)Nc3cnccc3N3CCC[C@H](N)C3)cs2)c1]

Following procedures described above in EXAMPLE 45 using (5)-tert-butyl 1-(3-(2-(5-(dimethylcarbamoyl)-2-fluorophenyl)thiazole-4-carboxamido)pyridin-4-yl)piperidin-3-ylcarbamate, the desired product (S)-N-(4-(3-aminopiperidin-1-yl)pyridin-3-yl)-2-(5-(dimethylcarbamoyl)-2-fluorophenyl)thiazole-4-carboxamid (18.3 mg, 51.5.0%) was obtained after reverse phase HPLC purification. $^1$H NMR (400 MHz, DMSO) δ 9.28 (s, 1H), 8.70 (d, J=7.6, 1H), 8.42 (dd, J=7.2, 2.1, 1H), 8.28 (d, J=5.3, 1H), 7.70-7.63 (m, 1H), 7.58 (dd, J=11.1, 8.5, 1H), 7.17 (d, J=5.3, 1H), 3.18 (d, J=7.9, 2H), 3.05 (s, 3H), 2.95 (s, 3H), 2.73-2.65 (m, 1H), 2.43 (dd, J=11.0, 9.3, 1H), 1.90-1.75 (m, 2H), 1.73-1.61 (m, 1H), 1.23-1.10 (m, 1H); ESIMS m/z=469.1 (M+1).

Example 48

(S)-N-(4-(3-aminopiperidin-1-yl)pyridin-3-yl)-2-phenylthiazole-4-carboxamide

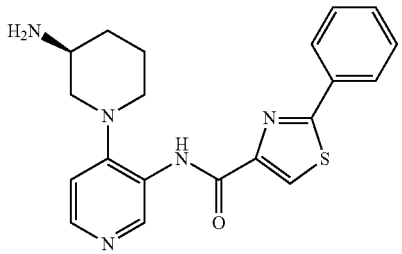 [SMILES: N[C@H]1CCCN(c2ccncc2NC(=O)c2csc(-c3ccccc3)n2)C1]

Following procedures described above in EXAMPLE 45, the desired product was obtained as a white powder (37.6 mg, 56%). $^1$H NMR (400 MHz, DMSO) δ 9.30 (s, 1H), 8.56 (s, 1H), 8.28 (d, J=8 Hz, 1H), 8.07 (m, 3H), 7.58 (m, 4H), 7.16 (d, J=4 Hz, 1H), 3.17 (m, 3H), 3.04 (m, 3H), 2.71 (m, 1H), 1.81 (m, 3H), 1.21 (m, 1H). ESIMS m/z=380.1 (M+1).

Example 49

(S)-5-amino-2-benzyl-N-(4-(3-(2,2,2-trifluoro acetamido)piperidin-1-yl)pyridin-3-yl)thiazole-4-carboxamide

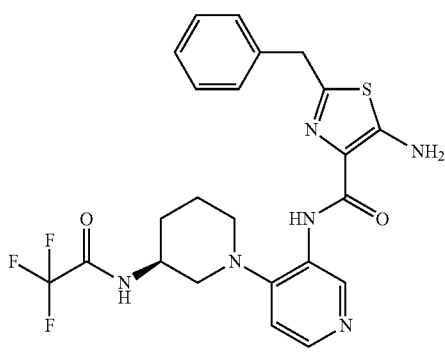 [SMILES: Nc1sc(Cc2ccccc2)nc1C(=O)Nc1cnccc1N1CCC[C@H](NC(=O)C(F)(F)F)C1]

The title compound was obtained as a by-product ((13 mg, 23%) during the synthesis of Example 38. $^1$H NMR (400 MHz, DMSO) δ 11.50 (s, 1H), 8.72 (s, 1H), 8.09 (d, J=5.4 Hz, 1H), 7.28 (dd, J=6.9, 6.0 Hz, 5H), 7.22-7.16 (m, 1H), 6.92 (d, J=5.5 Hz, 1H), 4.08 (d, J=6.5 Hz, 2H), 3.50 (d, J=10.9 Hz, 1H), 3.09 (s, 1H), 2.51 (d, J=11.0 Hz, 2H), 1.90 (d, J=11.9 Hz, 1H), 1.60 (d, J=14.4 Hz, 2H), 1.29 (d, J=7.3 Hz, 1H). MS (ESI) m/z: 505.1 [M+H$^+$].

Example 50

5-amino-2-(2,6-difluorophenyl)-N-(4-(piperazin-1-yl)pyridin-3-yl)thiazole-4-carboxamide

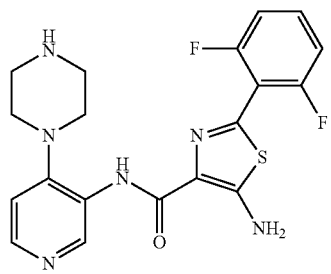 [SMILES: Nc1sc(-c2c(F)cccc2F)nc1C(=O)Nc1cnccc1N1CCNCC1]

Followed the procedure as described in EXAMPLE 1, starting with 5-(tert-butoxycarbonylamino)-2-(2,6-difluorophenyl)thiazole-4-carboxylic acid and tert-butyl 4-(3-aminopyridin-4-yl)piperazine-1-carboxylate. Obtained the desired product as a white solid (27.0 mg, 25%). prepared $^1$H NMR (400 MHz, DMSO) δ 9.29 (d, J=11.1, 1H), 8.86 (s, 1H), 8.31 (d, J=5.6, 1H), 7.71 (s, 2H), 7.64-7.52 (m, 1H), 7.30 (t, J=8.8, 3H), 3.26 (s, 8H). ESIMS m/z=417.4 (M+1).

Example 51

(S)-5-amino-N-(4-(3-aminopiperidin-1-yl)pyridin-3-yl)-2-(1H-pyrazol-3-yl)thiazole-4-carboxamide

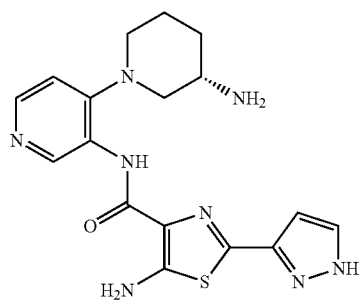 [SMILES: Nc1sc(-c2cc[nH]n2)nc1C(=O)Nc1cnccc1N1CCC[C@H](N)C1]

Followed the procedure as described in EXAMPLE 45, starting with (S)-tert-butyl 1-(3-(2-bromothiazole-4-carboxamido)pyridin-4-yl)piperidin-3-ylcarbamate and pyrazole-3-boronic acid. Obtained the desired product as a white solid (9.2 mg, 29%). $^1$H NMR (400 MHz, DMSO) δ 13.16 (s, 1H), 9.39 (d, J=19.6 Hz, 1H), 8.20 (d, J=5.2 Hz, 1H), 7.88 (d, J=2.3 Hz, 1H), 7.54 (d, J=23.5 Hz, 2H), 7.12 (d, J=5.3 Hz, 1H), 6.65 (d, J=2.3 Hz, 1H), 3.05 (ddd, J=27.3, 22.4, 11.5 Hz, 2H), 2.50 (m, J=3.6, 1.8 Hz, 2H), 1.83 (m, J=18.4, 8.5 Hz, 3H), 1.24 (s, 2H). ESIMS m/z=385.2 (M+1).

Example 52

(S)-5-amino-2-(2,6-difluorophenyl)-N-(4-(3-hydroxypiperidin-1-yl)pyridin-3-yl)thiazole-4-carboxamide

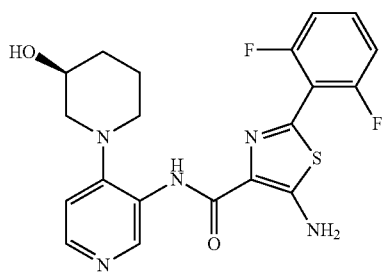

Followed the procedure as described in EXAMPLE 1, starting with 5-(tert-butoxycarbonylamino)-2-(2,6-bisfluorophenyl)thiazole-4-carboxylic acid and (S)-1-(3-aminopyridin-4-yl)piperidin-3-ol. Obtained the desired product as a white solid (111 mg, 100%). $^1$H NMR (400 MHz, DMSO) δ 9.37 (s, 1H), 9.30 (s, 1H), 8.21 (d, J=5.3 Hz, 1H), 7.67 (s, 2H), 7.59-7.47 (m, 1H), 7.29 (t, J=8.9 Hz, 2H), 7.14 (d, J=5.3 Hz, 1H), 4.81 (d, J=4.7 Hz, 2H), 3.81-3.63 (m, 3H), 3.19-3.07 (m, 1H), 2.99 (d, J=11.2 Hz, 1H), 2.61-2.33 (m, 2H), 1.90 (d, J=12.1 Hz, 1H), 1.71 (m, 3H), 1.30-1.09 (m, 2H). ESIMS m/z=432.2 (M+1).

Example 53

(R)-5-amino-N-(4-(3-aminopiperidin-1-yl)pyridin-3-yl)-2-(2-fluoro-5-(isopropylcarbamoyl)phenyl)thiazole-4-carboxamide

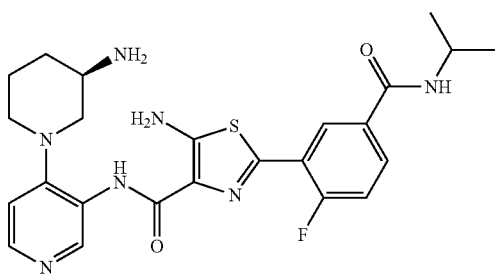 [SMILES: CC(C)NC(=O)c1ccc(F)c(-c2nc(C(=O)Nc3cnccc3N3CCC[C@@H](N)C3)c(N)s2)c1]

Followed the procedure as described in EXAMPLE 1, starting with 5-(tert-butoxycarbonylamino)-2-(2-fluoro-5-(isopropylcarbamoyl)phenyl)thiazole-4-carboxylic acid and (S)-tert-butyl 1-(3-aminopyridin-4-yl)piperidin-3-ylcarbamate. Obtained the desired product as a white solid (5 mg, 8%). $^1$H NMR (400 MHz, DMSO) δ 9.37 (s, 1H), 8.61 (dd, J=7.4, 2.2 Hz, 1H), 8.46 (d, J=7.6 Hz, 1H), 8.30 (s, 1H), 8.23 (d, J=5.3 Hz, 1H), 7.98-7.86 (m, 1H), 7.69 (s, 2H), 7.48 (dd, J=11.3, 8.7 Hz, 1H), 7.14 (d, J=5.3 Hz, 1H), 4.13 (td, J=13.5, 6.8 Hz, 1H), 3.20 (d, J=8.8 Hz, 9H), 3.01 (d, J=12.1 Hz, 2H), 2.70 (d, J=18.9 Hz, 1H), 1.89 (d, J=9.6 Hz, 1H), 1.78 (d, J=22.6 Hz, 2H), 1.40-1.23 (m, 1H), 1.19 (d, J=6.6 Hz, 6H). ESIMS m/z=498.2 (M+1).

Example 54

(S)-5-amino-N-(4-(3-aminopiperidin-1-yl)pyridin-3-yl)-2-(2,6-dimethylphenyl)thiazole-4-carboxamide

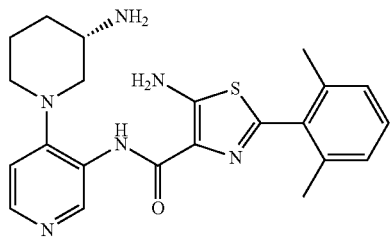 [SMILES: Cc1cccc(C)c1-c1nc(C(=O)Nc2cnccc2N2CCC[C@H](N)C2)c(N)s1]

Followed the procedure as described in EXAMPLE 1, starting with 5-(tert-butoxycarbonylamino)-2-(2,6-dimethylphenyl)thiazole-4-carboxylic acid and (S)-tert-butyl 1-(3-aminopyridin-4-yl)piperidin-3-ylcarbamate. Obtained the desired product as a white solid (8 mg, 13%). $^1$H NMR (400 MHz, DMSO) δ 9.22 (s, 1H), 8.18 (d, J=5.3 Hz, 1H), 7.48 (s, 2H), 7.35-7.26 (m, 1H), 7.17 (d, J=7.7 Hz, 2H), 7.04 (d, J=5.3 Hz, 1H), 3.06 (t, J=14.4 Hz, 1H), 2.99 (d, J=11.7 Hz, 1H), 2.83-2.66 (m, 1H), 2.64-2.48 (m, 1H), 2.45-2.31 (m, 1H), 2.21 (s, 6H), 1.64 (dd, J=17.0, 6.8 Hz, 2H), 1.57-1.41 (m, 1H), 1.17-0.95 (m, 1H). ESIMS m/z=423.2 (M+1).

Example 55

(S)-5-amino-N-(4-(3-aminopiperidin-1-yl)pyridin-3-yl)-2-(2-chloro-6-fluorophenyl)thiazole-4-carboxamide

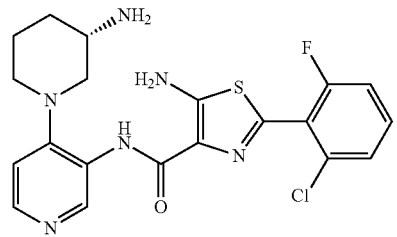 [SMILES: Nc1sc(-c2c(F)cccc2Cl)nc1C(=O)Nc1cnccc1N1CCC[C@H](N)C1]

Followed the procedure as described in EXAMPLE 45, starting with (S)-tert-butyl 1-(3-(2-bromothiazole-4-carboxamido)pyridin-4-yl)piperidin-3-ylcarbamate and 2-chloro-6-fluorophenylboronic acid. Obtained the desired product as a white solid (5 mg, 13%). ESIMS m/z=447.1 (M+1).

Example 56

(S)-5-amino-N-(4-(3-aminopiperidin-1-yl)pyridin-3-yl)-2-(1H-pyrazol-4-yl)thiazole-4-carboxamide

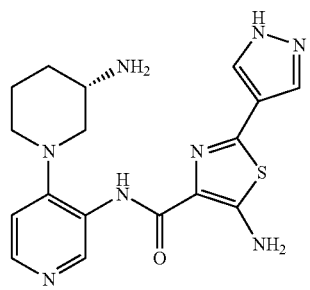 [SMILES: Nc1sc(-c2cn[nH]c2)nc1C(=O)Nc1cnccc1N1CCC[C@H](N)C1]

Followed the procedure as described in EXAMPLE 45, starting with (S)-tert-butyl 1-(3-(2-bromothiazole-4-carboxamido)pyridin-4-yl)piperidin-3-ylcarbamate and 4-(4,4,5,5-tetramethyl-1,3,2-dioxaborolan-2-yl)-1H-pyrazole. Obtained the desired product as a white solid (4 mg, 10%). ESIMS m/z=385.2 (M+1).

Example 57

(S)-5-amino-N-(4-(3-aminopiperidin-1-yl)pyridin-3-yl)-2-(imidazo[1,2-a]pyridin-3-yl)thiazole-4-carboxamide

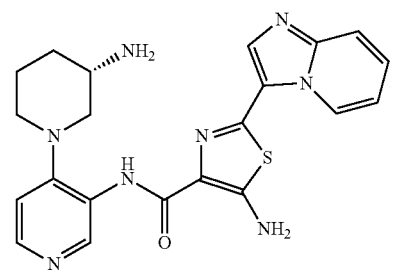 [SMILES: Nc1sc(-c2cnc3ccccn23)nc1C(=O)Nc1cnccc1N1CCC[C@H](N)C1]

Followed the procedure as described in EXAMPLE 45, starting with (S)-tert-butyl 1-(3-(2-bromothiazole-4-carboxamido)pyridin-4-yl)piperidin-3-ylcarbamate and 3-(4,4,5,5-tetramethyl-1,3,2-dioxaborolan-2-yl)imidazo[1,2-a]pyridine. Obtained the desired product as a white solid (12 mg, 26%). $^1$H NMR (500 MHz, DMSO) δ 9.53 (d, J=6.8 Hz, 1H), 9.18 (s, 1H), 8.22 (d, J=5.3 Hz, 1H), 8.11 (s, 1H), 7.76 (d, J=8.1 Hz, 1H), 7.66 (s, 2H), 7.53-7.41 (m, 1H), 7.12 (dd, J=12.0, 5.6 Hz, 2H), 3.20 (d, J=11.5 Hz, 1H), 3.08 (d, J=11.6 Hz, 1H), 2.93 (s, 1H), 2.76-2.59 (m, 1H), 2.48-2.39 (m, 1H), 1.73 (d, J=9.5 Hz, 1H), 1.65 (s, 1H), 1.13 (d, J=9.3 Hz, 1H). ESIMS m/z=435.2 (M+1).

Example 58

(S)-5-amino-N-(4-(3-aminopiperidin-1-yl)pyridin-3-yl)-2-(2,6-dichlorophenyl)thiazole-4-carboxamide

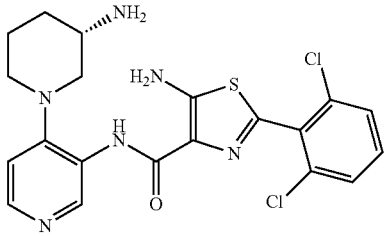 [SMILES: Nc1sc(-c2c(Cl)cccc2Cl)nc1C(=O)Nc1cnccc1N1CCC[C@H](N)C1]

Followed the procedure as described in EXAMPLE 1, starting with 5-(tert-butoxycarbonylamino)-2-(2,6-dichlorophenyl)thiazole-4-carboxylic acid and (S)-tert-butyl 1-(3-aminopyridin-4-yl)piperidin-3-ylcarbamate. Obtained the desired product as a white solid (9 mg). $^1$H NMR (500 MHz, DMSO) δ 9.21 (s, 1H), 8.18 (d, J=5.3 Hz, 1H), 7.69-7.60 (m, 2H), 7.56 (dd, J=8.9, 7.3 Hz, 3H), 7.04 (d, J=5.3 Hz, 1H), 3.08 (d, J=8.1 Hz, 1H), 2.97 (d, J=11.9 Hz, 1H), 2.79 (d, J=9.0 Hz, 1H), 2.56 (dd, J=21.5, 11.0 Hz, 1H), 2.48-2.41 (m, 1H), 1.66 (d, J=14.0 Hz, 2H), 1.54 (d, J=10.1 Hz, 1H), 1.11 (d, J=9.8 Hz, 1H). ESIMS m/z=463.1 (M+1).

Example 59

(S)-5-amino-N-(4-(3-aminopiperidin-1-yl)pyridin-3-yl)-2-(prop-1-en-2-yl)thiazole-4-carboxamide

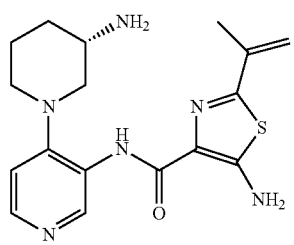 [SMILES: C=C(C)c1nc(C(=O)Nc2cnccc2N2CCC[C@H](N)C2)c(N)s1]

Followed the procedure as described in EXAMPLE 1, starting with 5-(tert-butoxycarbonylamino)-2-(prop-1-en-2-yl)thiazole-4-carboxylic acid and (S)-tert-butyl 1-(3-aminopyridin-4-yl)piperidin-3-ylcarbamate. Obtained the desired product as a white solid (9 mg). ESIMS m/z=359.3 (M+1).

Example 60

(S)-5-amino-N-(4-(3-aminopiperidin-1-yl)pyridin-3-yl)-2-cyclopentylthiazole-4-carboxamide

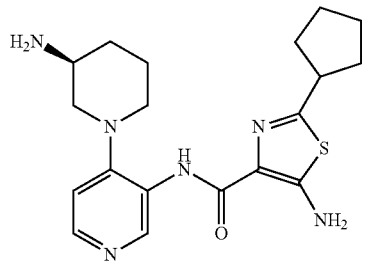

Followed the procedure as described in EXAMPLE 1, starting with 5-(tert-butoxycarbonylamino)-2-cyclopentylthiazole-4-carboxylic acid and (S)-tert-butyl 1-(3-aminopyridin-4-yl)piperidin-3-ylcarbamate. Obtained the desired product as a white solid (22 mg, 48%). $^1$H NMR (500 MHz, DMSO) δ 9.39 (s, 1H), 8.18 (d, J=5.2 Hz, 1H), 7.24 (s, 1H), 7.10 (d, J=5.3 Hz, 1H), 3.23 (m, 3H), 3.07 (d, J=10.5 Hz, 1H), 2.96 (d, J=9.7 Hz, 2H), 2.67-2.53 (m, 2H), 2.43-2.34 (m, 1H), 2.03 (d, J=8.1 Hz, 2H), 1.87 (d, J=12.5 Hz, 1H), 1.84-1.58 (m, 5H), 1.17 (d, J=13.3 Hz, 1H). ESIMS m/z=387.2 (M+1).

Example 61

(S)-5-amino-N-(4-(3-aminopiperidin-1-yl)pyridin-3-yl)-2-(imidazo[1,2-a]pyridin-6-yl)thiazole-4-carboxamide

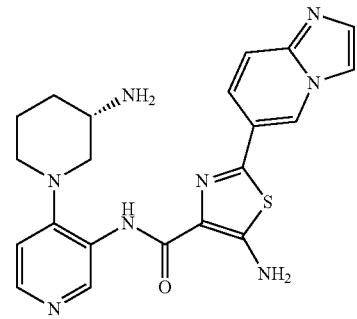 [SMILES: Nc1sc(-c2ccc3nccn3c2)nc1C(=O)Nc1cnccc1N1CCC[C@H](N)C1]

Followed the procedure as described in EXAMPLE 45, starting with (S)-tert-butyl 1-(3-(2-bromothiazole-4-carboxamido)pyridin-4-yl)piperidin-3-ylcarbamate and imidazo[1,2-a]pyridin-6-ylboronic acid. Obtained the desired product as a white solid (44 mg, 100%). $^1$H NMR (500 MHz, DMSO) δ 9.34 (s, 1H), 9.05 (s, 1H), 8.29 (s, 1H), 8.22 (d, J=5.2 Hz, 1H), 8.00 (s, 1H), 7.71 (m, 5H), 7.13 (d, J=5.2 Hz, 1H), 3.00 (d, J=11.5 Hz, 2H), 2.81-2.67 (m, 1H), 2.50 (dt, J=3.6, 1.8 Hz, 1H), 2.01-1.60 (m, 3H), 1.27 (d, J=35.4 Hz, 2H). ESIMS m/z=435.1 (M+1).

Example 62

5-amino-N-(4-((3S,5R)-3-amino-5-fluoropiperidin-1-yl)pyridin-3-yl)-2-(2-fluorophenyl)thiazole-4-carboxamide

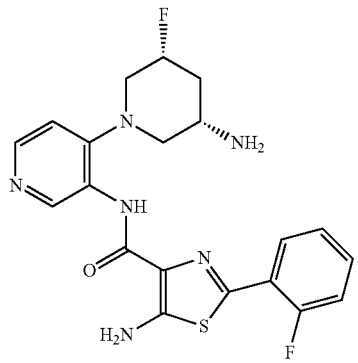 [SMILES: Nc1sc(-c2ccccc2F)nc1C(=O)Nc1cnccc1N1C[C@@H](N)C[C@@H](F)C1]

Followed the procedure as described in EXAMPLE 1, starting with tert-butyl (3S,5R)-1-(3-aminopyridin-4-yl)-5-fluoropiperidin-3-ylcarbamate and 5-(tert-butoxycarbonylamino)-2-(2-fluorophenyl)thiazole-4-carboxylic acid. Obtained the desired product as a white solid (50 mg). ESIMS m/z=431.1 (M+1).

Example 63

5-amino-N-(4-((3S,5R)-3-amino-5-fluoropiperidin-1-yl)pyridin-3-yl)-2-(2,6-difluorophenyl)thiazole-4-carboxamide

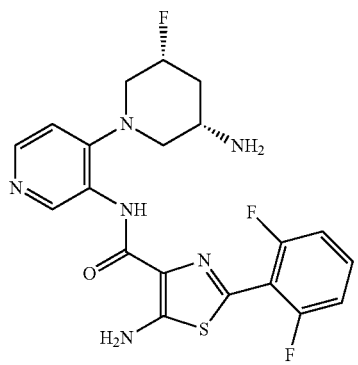 [SMILES: Nc1sc(-c2c(F)cccc2F)nc1C(=O)Nc1cnccc1N1C[C@@H](N)C[C@@H](F)C1]

Followed the procedure as described in EXAMPLE 1, starting with tert-butyl (3S,5R)-1-(3-aminopyridin-4-yl)-5-fluoropiperidin-3-ylcarbamate and 5-(tert-butoxycarbonylamino)-2-(2,6-bisfluorophenyl)thiazole-4-carboxylic acid. Obtained the desired product as a white solid (50 mg). $^1$H NMR (500 MHz, DMSO) δ 9.25 (s, 1H), 8.18 (t, J=20.9 Hz, 1H), 7.64 (s, 2H), 7.53 (ddd, J=14.8, 8.4, 6.4 Hz, 2H), 7.26 (t, J=8.7 Hz, 2H), 7.12 (d, J=5.3 Hz, 1H), 4.94 (d, J=46.1 Hz, 1H), 3.05 (dd, J=32.9, 12.7 Hz, 2H), 2.66-2.34 (m, 3H), 2.07 (s, 1H), 1.53 (dt, J=23.8, 11.5 Hz, 1H). ESIMS m/z=449.1 (M+1).

Example 64

5-amino-N-(4-(3-aminopiperidin-1-yl)pyridin-3-yl)-2-(pyrrolidin-3-yl)thiazole-4-carboxamide

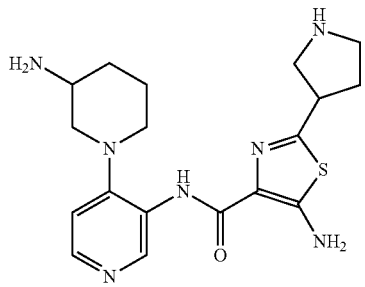

Followed the procedure as described in EXAMPLE 1, starting with tert-butyl 1-(3-aminopyridin-4-yl)piperidin-3-ylcarbamate and 2-(1-(tert-butoxycarbonyl)pyrrolidin-3-yl)-5-(tert-butoxycarbonylamino)thiazole-4-carboxylic acid. Obtained the desired product as a white solid (13.5 mg, 32%). $^1$H NMR (500 MHz, DMSO) δ 9.38 (s, 1H), 8.18 (d, J=5.2 Hz, 1H), 7.26 (s, 2H), 7.09 (d, J=5.2 Hz, 1H), 3.08 (d, J=10.9 Hz, 2H), 2.96 (d, J=11.4 Hz, 4H), 2.62 (d, J=17.6 Hz, 1H), 2.43-2.36 (m, 1H), 2.15 (s, 1H), 1.82 (dd, J=63.4, 20.3 Hz, 4H), 1.18 (d, J=11.6 Hz, 2H). ESIMS m/z=388.2 (M+1).

Example 65

5-amino-N-(4-(3-aminopiperidin-1-yl)pyridin-3-yl)-2-(piperidin-3-yl)thiazole-4-carboxamide

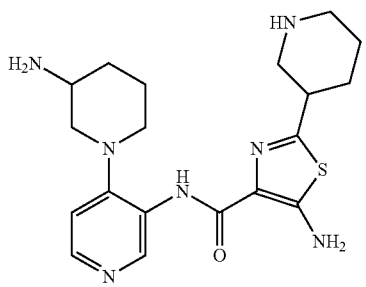 [SMILES: Nc1sc(C2CCCNC2)nc1C(=O)Nc1cnccc1N1CCCC(N)C1]

Followed the procedure as described in EXAMPLE 1, starting with tert-butyl 1-(3-aminopyridin-4-yl)piperidin-3-ylcarbamate and 2-(1-(tert-butoxycarbonyl)piperidin-3-yl)-5-(tert-butoxycarbonylamino)thiazole-4-carboxylic acid. Obtained the desired product as a white solid (6.4 mg, 51%). $^1$H NMR (500 MHz, DMSO) δ 9.38 (s, 1H), 8.37 (s, 1H), 8.19 (d, J=5.1 Hz, 1H), 7.28 (s, 2H), 7.11 (d, J=5.1 Hz, 1H), 3.14 (dd, J=28.4, 11.4 Hz, 2H), 2.94 (dd, J=51.3, 24.0 Hz, 4H), 2.65 (dd, J=27.1, 13.0 Hz, 2H), 2.50-2.40 (m, 1H), 2.05 (s, 1H), 1.97-1.56 (m, 5H), 1.47 (d, J=11.2 Hz, 1H), 1.24 (d, J=8.3 Hz, 2H). ESIMS m/z=402.1 (M+1).

Example 66

(S)-5-amino-N-(4-(3-aminopiperidin-1-yl)pyridin-3-yl)-2-(3-fluoropyridin-2-yl)thiazole-4-carboxamide

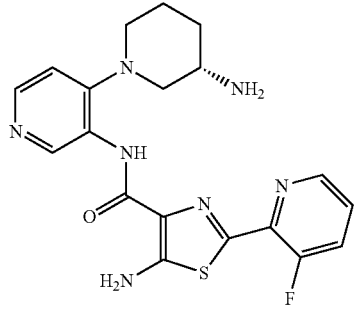 [SMILES: Nc1sc(-c2ncccc2F)nc1C(=O)Nc1cnccc1N1CCC[C@H](N)C1]

Followed the procedure as described in EXAMPLE 1, starting with (S)-tert-butyl 1-(3-aminopyridin-4-yl)piperidin-3-ylcarbamate and 5-(tert-butoxycarbonylamino)-2-(3-fluoropyridin-2-yl)thiazole-4-carboxylic acid. Obtained the desired product as a white solid (50 mg, 55%). $^1$H NMR (500 MHz, DMSO) δ 9.40 (s, 1H), 8.44 (d, J=4.6 Hz, 1H), 8.21 (d, J=5.2 Hz, 1H), 7.86 (dd, J=25.8, 14.5 Hz, 3H), 7.58-7.40 (m, 1H), 7.13 (d, J=5.2 Hz, 1H), 3.09 (d, J=9.1 Hz, 1H), 3.00 (d, J=12.6 Hz, 2H), 2.59 (dd, J=26.2, 15.4 Hz, 1H), 2.37 (t, J=10.1 Hz, 1H), 1.90 (s, 1H), 1.78 (d, J=15.8 Hz, 2H), 1.14 (d, J=8.7 Hz, 1H). ESIMS m/z=414.1 (M+1).

We claim:

1. A method for treating a hematopoietic malignancy in a patient, comprising administering to the patient a therapeutic combination comprising a therapeutically effective amount of a pharmaceutical composition comprising (S)-5-amino-N-(4-(3-aminopiperidin-1-yl)pyridin-3-yl)-2-(2,6-difluorophenyl)thiazole-4-carboxamide and a pharmaceutically acceptable carrier; and
a therapeutically effective amount of Formula A:

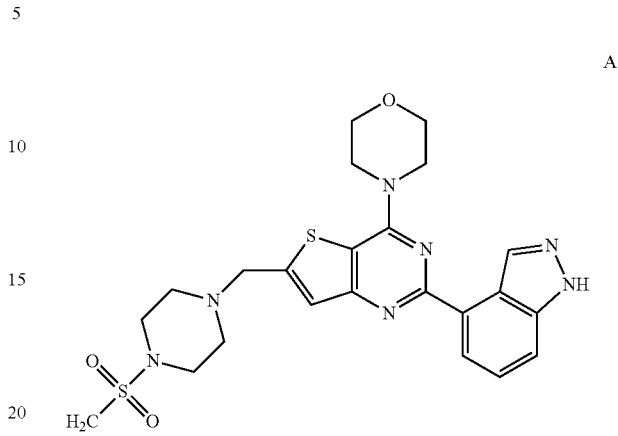

A wherein the hematopoietic malignancy is multiple myeloma.

2. The method of claim 1 wherein the therapeutically effective amount of the pharmaceutical composition comprising (S)-5-amino-N-(4-(3-aminopiperidin-1-yl)pyridin-3-yl)-2-(2,6-difluorophenyl)thiazole-4-carboxamide, and the therapeutically effective amount of Formula A are administered as a combined formulation.

3. The method of claim 1 wherein the therapeutically effective amount of the pharmaceutical composition comprising (S)-5-amino-N-(4-(3-aminopiperidin-1-yl)pyridin-3-yl)-2-(2,6-difluorophenyl)thiazole-4-carboxamide, and the therapeutically effective amount of Formula A are administered by alternation.

4. The method of claim 1 wherein administration of the therapeutic combination results in a synergistic effect.

* * * * *